(12) United States Patent
Martin

(10) Patent No.: US 8,492,370 B2
(45) Date of Patent: Jul. 23, 2013

(54) COMPOUNDS AND METHODS FOR THEIR PRODUCTION

(75) Inventor: Christine Martin, Essex (GB)

(73) Assignee: Bristol-Myers Squibb Company, Princeton, NJ (US)

( * ) Notice: Subject to any disclaimer, the term of this patent is extended or adjusted under 35 U.S.C. 154(b) by 589 days.

(21) Appl. No.: 12/513,967

(22) PCT Filed: Nov. 9, 2007

(86) PCT No.: PCT/GB2007/050679
§ 371 (c)(1),
(2), (4) Date: Oct. 12, 2010

(87) PCT Pub. No.: WO2008/056188
PCT Pub. Date: May 15, 2008

(65) Prior Publication Data
US 2011/0021481 A1    Jan. 27, 2011

(30) Foreign Application Priority Data

Nov. 9, 2006  (GB) .................................. 0622342.4
Oct. 24, 2007  (GB) .................................. 0720875.4

(51) Int. Cl.
*C07D 225/06*  (2006.01)
*A61K 31/395*  (2006.01)

(52) U.S. Cl.
USPC .......................................... 514/183; 540/461

(58) Field of Classification Search
USPC .......................................... 540/461; 514/183
See application file for complete search history.

(56) References Cited

U.S. PATENT DOCUMENTS 7,465,718 B2 * 12/2008 Zhang et al. .................. 514/183

FOREIGN PATENT DOCUMENTS

| CN | 101012196 | | 8/2007 |
|---|---|---|---|
| EP | 1 897 871 A1 | | 3/2008 |
| WO | WO 93/14215 | * | 7/1993 |
| WO | WO 03/066005 | | 8/2003 |
| WO | 2005/061461 | | 7/2005 |
| WO | WO 2005/061461 | | 7/2005 |
| WO | WO 2005/063714 | | 7/2005 |
| WO | WO 2006/098761 | | 9/2006 |
| WO | 2007/001049 | | 1/2007 |
| WO | WO 2007/001049 | | 4/2007 |
| WO | 2007/074347 | | 7/2007 |
| WO | WO 2008/094438 | | 8/2008 |

OTHER PUBLICATIONS

Carter et al. (Organic Letters (2004), 6(1), 55-57).*
Andrus et al. (Organic Letters (2002), 4(20), 3549-3552).*
Stead, P., et al. "Discovery of novel ansamycins possessing potent inhibitory activity in a cell-based oncostatin M signalling assay." J Antibiot (Tokyo). Jul. 2000;53(7):657-63.
Li, M., et al. "Isolation and Structure Eludcidation of Autolytimycin, A new Compound Produced by Streptomyces Autolyticus JX-47." Chinese Chem Lett. Jan. 1, 2001;12(10):903-906.
Takatsu, T., et al. "Reblastatin, a novel benzenoid ansamycin-type cell cycle inhibitor." J Antibiot (Tokyo). Nov. 2000;53(11):1310-2.
Schnur, R.C. et al., "Inhibition of the Oncogene Product p185$^{erbB-2}$ in Vitro and in Vivo by Geldanamycin and Dihydrogeldanamycin Derivatives," Journal of Medicinal Chemistry, vol. 38, pp. 3806-3812 (1995).
Tadtong, S. et al., "Geldanamycin derivatives and neuroprotective effect on cultured P19-derived neurons," Bioorganic & Medicinal Chemistry Letters, vol. 17, pp. 2939-2943 (May 15, 2007).
Ge, J. et al., "Design, Synthesis, and Biological Evaluation of Hydroquinone Derivatives of 17-Amino-17-demethoxygeldanamycin as Potent, Water-Soluble Inhibitors of Hsp90," Journal of Medicinal Chemistry, vol. 49, pp. 4606-4615 (Jun. 29, 2006).
Andrus, M.B. et al., "Total Synthesis of (+)-Geldanamycin and (−)-o-Quinogeldanamycin with Use of Asymmetric Anti-and Syn-Glycolate Aldol Reactions," Organic Letters, vol. 4, No. 20, pp. 3549-3552 (2002).
Nakata, M. et al., "The Total Synthesis of Herbimycin A," Bulletin of the Chemical Society of Japan, vol. 65, No. 1, pp. 2974-2991 (1992).
Japanese office action issued Jan. 29, 2013.

* cited by examiner

Primary Examiner — Bruck Kifle
(74) Attorney, Agent, or Firm — Elliott Korsen

(57) ABSTRACT

The present invention relates to ansamycin analogues that are useful, e.g. in the treatment of cancer, B-cell malignancies, malaria, fungal infection, diseases of the central nervous system and neurodegenerative diseases, diseases dependent on angiogenesis, autoimmune diseases or a prophylactic pre-treatment for cancer. The present invention also provides methods for the production of these compounds and their use in medicine.

13 Claims, 4 Drawing Sheets

COMPOUNDS AND METHODS FOR THEIR PRODUCTION

The present application is §371 application of PCT/GB2007/050679 filed Nov. 9, 2007, which claims priority to GB Application No. 0622342.4 filed Nov. 9, 2006 and GB Application No. 0720875.4 filed Oct. 24, 2007. The entire disclosure of each of the foregoing applications is incorporated by reference herein.

The present invention relates to ansamycin analogues that are useful, e.g. in the treatment of cancer, B-cell malignancies, malaria, fungal infection, diseases of the central nervous system and neurodegenerative diseases, diseases dependent on angiogenesis, autoimmune diseases or as a prophylactic pretreatment for cancer. The present invention also provides methods for the production of these compounds and their use in medicine.

BACKGROUND OF THE INVENTION

The development of highly specific anticancer drugs with low toxicity and favourable pharmacokinetic characteristics comprises a major challenge in anticancer therapy.

The 90 kDa heat shock protein (Hsp90) is an abundant molecular chaperone involved in the folding and assembly of proteins, many of which are involved in signal transduction pathways (for reviews see Neckers, 2002; Sreedhar et al., 2004a; Wegele et al., 2004 and references therein). So far nearly 50 of these so-called client proteins have been identified and include steroid receptors, non-receptor tyrosine kinases e.g. src family, cyclin-dependent kinases e.g. cdk4 and cdk6, the cystic transmembrane regulator, nitric oxide synthase and others (Donzé and Picard, 1999; McLaughlin et al., 2002; Chiosis et al., 2004; Wegele et al., 2004; http://www.picard.ch/downloads/Hsp90interactors.pdf). Furthermore, Hsp90 plays a key role in stress response and protection of the cell against the effects of mutation (Bagatell and Whitesell, 2004; Chiosis et al., 2004). The function of Hsp90 is complicated and it involves the formation of dynamic multienzyme complexes (Bohen, 1998; Liu et al., 1999; Young et al., 2001; Takahashi et al., 2003; Sreedhar et al., 2004; Wegele et al., 2004). Hsp90 is a target for inhibitors (Fang et al., 1998; Liu et al., 1999; Blagosklonny, 2002; Neckers, 2003; Takahashi et al., 2003; Beliakoff and Whitesell, 2004; Wegele et al., 2004) resulting in degradation of client proteins, cell cycle dysregulation/or normalisation and apoptosis. More recently, Hsp90 has been identified as an important extracellular mediator for tumour invasion (Eustace et al., 2004). Hsp90 was identified as a new major therapeutic target for cancer therapy which is mirrored in the intense and detailed research about Hsp90 function (Blagosklonny et al., 1996; Neckers, 2002; Workman and Kaye, 2002; Beliakoff and Whitesell, 2004; Harris et al., 2004; Jez et al., 2003; Lee et al., 2004) and the development of high-throughput screening assays (Carreras et al., 2003; Rowlands et al., 2004). Hsp90 inhibitors include compound classes such as ansamycins, macrolides, purines, pyrazoles, coumarin antibiotics and others (for review see Bagatell and Whitesell, 2004; Chiosis et al., 2004 and references therein).

The benzenoid ansamycins are a broad class of chemical structures characterised by an aliphatic ring of varying length joined either side of an aromatic ring structure. Naturally occurring ansamycins include: macbecin and 18,21-dihydromacbecin (also known as macbecin I and macbecin II respectively) (1 & 2; Tanida et al., 1980), geldanamycin (3; DeBoer et al., 1970; DeBoer and Dietz, 1976; WO 03/106653 and references therein), and the herbimycin family (4; 5; 6; Omura et al., 1979, Iwai et al., 1980 and Shibata et al, 1986a, WO 03/106653 and references therein).

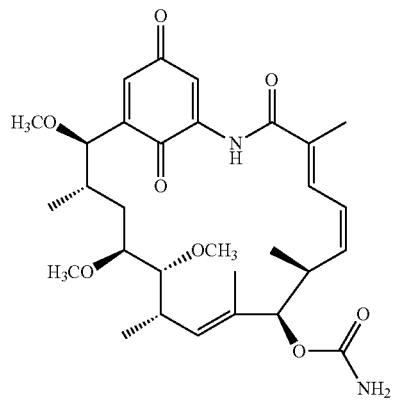

macbecin, 1

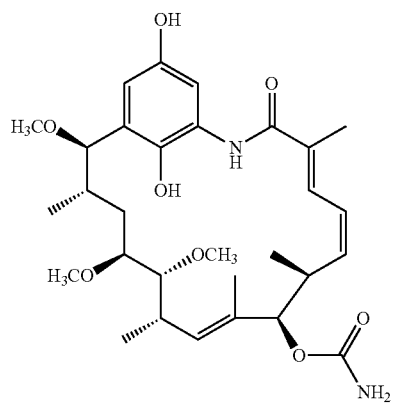

18,21-dihydromacbecin (macbecin II), 2

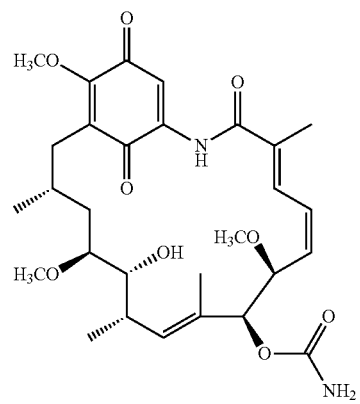

geldanamycin, 3

-continued

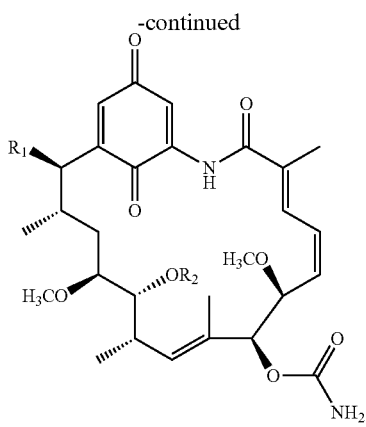

herbimycin A, 4 R₁ = OCH₃, R₂ = CH₃
herbimycin B, 5 R₁ = H, R₂ = H
herbimycin C, 6 R₁ = OCH₃, R₂ = H Ansamycins were originally identified for their antibacterial and antiviral activity, however, recently their potential utility as anticancer agents has become of greater interest (Beliakoff and Whitesell, 2004). Many Hsp90 inhibitors are currently being assessed in clinical trials (Csermely and Soti, 2003; Workman, 2003). In particular, geldanamycin has nanomolar potency and apparent specificity for aberrant protein kinase dependent tumour cells (Chiosis et al., 2003; Workman, 2003).

It has been shown that treatment with Hsp90 inhibitors enhances the induction of tumour cell death by radiation and increased cell killing abilities (e.g. breast cancer, chronic myeloid leukaemia and non-small cell lung cancer) by combination of Hsp90 inhibitors with cytotoxic agents has also been demonstrated (Neckers, 2002; Beliakoff and Whitesell, 2004). The potential for anti-angiogenic activity is also of interest: the Hsp90 client protein HIF-1α plays a key role in the progression of solid tumours (Hur et al., 2002; Workman and Kaye, 2002; Kaur et al., 2004).

Hsp90 inhibitors also function as immunosuppressants and are involved in the complement-induced lysis of several types of tumour cells after Hsp90 inhibition (Sreedhar et al., 2004). Treatment with Hsp90 inhibitors can also result in induced superoxide production (Sreedhar et al., 2004a) associated with immune cell-mediated lysis (Sreedhar et al., 2004). The use of Hsp90 inhibitors as potential anti-malaria drugs has also been discussed (Kumar et al., 2003). Furthermore, it has been shown that geldanamycin interferes with the formation of complex glycosylated mammalian prion protein PrP$^c$ (Winklhofer et al., 2003).

As described above, ansamycins are of interest as potential anticancer and anti-B-cell malignancy compounds, however the currently available ansamycins exhibit poor pharmacological or pharmaceutical properties, for example they show poor water solubility, poor metabolic stability, poor bioavailability or poor formulation ability (Goetz et al., 2003; Workman 2003; Chiosis 2004). Both herbimycin A and geldanamycin were identified as poor candidates for clinical trials due to their strong hepatotoxicity (review Workman, 2003) and geldanamycin was withdrawn from Phase I clinical trials due to hepatotoxicity (Supko et al., 1995; WO 03/106653).

Geldanamycin was isolated from culture filtrates of *Streptomyces hygroscopicus* and shows strong activity in vitro against protozoa and weak activity against bacteria and fungi. In 1994 the association of geldanamycin with Hsp90 was shown (Whitesell et al., 1994). The biosynthetic gene cluster for geldanamycin was cloned and sequenced (Allen and Ritchie, 1994; Rascher et al., 2003; WO 03/106653). The DNA sequence is available under the NCBI accession number AY179507. The isolation of genetically engineered geldanamycin producer strains derived from *S. hygroscopicus* subsp. *duamyceticus* JCM4427 and the isolation of 4,5-dihydro-7-O-descarbamoyl-7-hydroxygeldanamycin and 4,5-dihydro-7-O-descarbamoyl-7-hydroxy-17-O-demethylgeldanamycin were described recently (Hong et al., 2004). By feeding geldanamycin to the herbimycin producing strain *Streptomyces hygroscopicus* AM-3672 the compounds 15-hydroxygeldanamycin, the tricyclic geldanamycin analogue KOSN-1633 and methyl-geldanamycinate were isolated (Hu et al., 2004). The two compounds 17-formyl-17-demethoxy-18-O-21-O-dihydrogeldanamycin and 17-hydroxymethyl-17-demethoxygeldanamycin were isolated from *S. hygroscopicus* K279-78. *S. hygroscopicus* K279-78 is *S. hygroscopicus* NRRL 3602 containing cosmid pKOS279-78 which has a 44 kbp insert which contains various genes from the herbimycin producing strain *Streptomyces hygroscopicus* AM-3672 (Hu et al., 2004). Substitutions of acyltransferase domains have been made in four of the modules of the polyketide synthase of the geldanamycin biosynthetic cluster (Patel et al., 2004). AT substitutions were carried out in modules 1, 4 and 5 leading to the fully processed analogues 14-desmethyl-geldanamycin, 8-desmethyl-geldanamycin and 6-desmethoxy-geldanamycin and the not fully processed 4,5-dihydro-6-desmethoxy-geldanamycin. Substitution of the module 7 AT lead to production of three 2-desmethyl compounds, KOSN1619, KOSN1558 and KOSN1559, one of which (KOSN1559), a 2-demethyl-4,5-dihydro-17-demethoxy-21-deoxy derivative of geldanamycin, binds to Hsp90 with a 4-fold greater binding affinity than geldanamycin and an 8-fold greater binding affinity than 17-AAG. However this is not reflected in an improvement in the IC$_{50}$ measurement using SKBr3. Another analogue, a novel nonbenzoquinoid geldanamycin, designated KOS-1806 has a monophenolic structure (Rascher et al., 2005). No activity data was given for KOS-1806.

In 1979 the ansamycin antibiotic herbimycin A was isolated from the fermentation broth of *Streptomyces hygroscopicus* strain No. AM-3672 and named according to its potent herbicidal activity. The antitumour activity was established by using cells of a rat kidney line infected with a temperature sensitive mutant of Rous sarcoma virus (RSV) for screening for drugs that reverted the transformed morphology of the these cells (for review see Uehara, 2003). Herbimycin A was postulated as acting primarily through the binding to Hsp90 chaperone proteins but the direct binding to the conserved cysteine residues and subsequent inactivation of kinases was also discussed (Uehara, 2003).

Chemical derivatives have been isolated and compounds with altered substituents at C19 of the benzoquinone nucleus and halogenated compounds in the ansa chain showed less toxicity and higher antitumour activities than herbimycin A (Omura et al., 1984; Shibata et al., 1986b). The sequence of the herbimycin biosynthetic gene cluster was identified in WO 03/106653 and in a recent paper (Rascher et al., 2005).

The ansamycin compounds macbecin (1) and 18,21-dihydromacbecin (2) (C-14919E-1 and C-14919E-1), identified by their antifungal and antiprotozoal activity, were isolated from the culture supernatants of *Nocardia* sp No. C-14919 (*Actinosynnema pretiosum* subsp *pretiosum* ATCC 31280) (Tanida et al., 1980; Muroi et al., 1980; Muroi et al., 1981; U.S. Pat. No. 4,315,989 and U.S. Pat. No. 4,187,292). 18,21-Dihydromacbecin is characterized by containing the dihydroquinone form of the nucleus. Both macbecin and 18,21-dihydromacbecin were shown to possess similar antibacterial and antitumour activities against cancer cell lines such as the murine leukaemia P388 cell line (Ono et al., 1982). Reverse transcriptase and terminal deoxynucleotidyl transferase activities were not inhibited by macbecin (Ono et al., 1982). The Hsp90 inhibitory function of macbecin has been reported in the literature (Bohen, 1998; Liu et al., 1999). The conversion of macbecin and 18,21-dihydromacbecin after adding to a microbial culture broth into a compound with a hydroxy group instead of a methoxy group at a certain position or positions is described in U.S. Pat. No. 4,421,687 and U.S. Pat. No. 4,512,975.

During a screen of a large variety of soil microorganisms, the compounds TAN-420A to E were identified from producer strains belonging to the genus *Streptomyces* (7-11, EP 0 110 710).

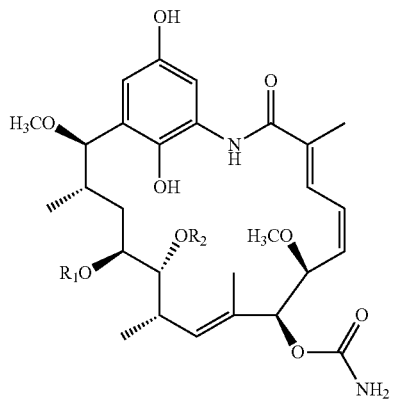

TAN-420A, 7 R$_1$ = H, R$_2$ = H
TAN-420C, 9 R$_1$ = H, R$_2$ = CH$_3$
TAN-420E, 11 R$_1$ = CH$_3$, R$_2$ = CH$_3$

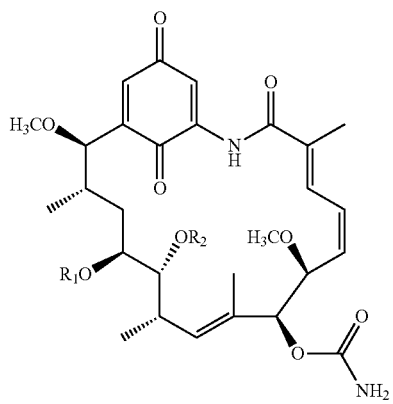

TAN-420B, 8 R$_1$ = H, R$_2$ = H
TAN-420D, 10 R$_1$ = H, R$_2$ = CH$_3$

In 2000, the isolation of the geldanamycin related, non-benzoquinone ansamycin metabolite reblastatin from cell cultures of *Streptomyces* sp. S6699 and its potential therapeutic value in the treatment of rheumatoid arthritis was described (Stead et al., 2000).

A further Hsp90 inhibitor, distinct from the chemically unrelated benzoquinone ansamycins is Radicicol (monorden) which was originally discovered for its antifungal activity from the fungus *Monosporium bonorden* (for review see Uehara, 2003) and the structure was found to be identical to the 14-membered macrolide isolated from *Nectria radicicola*. In addition to its antifungal, antibacterial, anti-protozoan and cytotoxic activity it was subsequently identified as an inhibitor of Hsp90 chaperone proteins (for review see Uehara, 2003; Schulte et al., 1999). The anti-angiogenic activity of radicicol (Hur et al., 2002) and semi-synthetic derivates thereof (Kurebayashi et al., 2001) has also been described.

Recent interest has focussed on 17-amino derivatives of geldanamycin as a new generation of ansamycin anticancer compounds (Bagatell and Whitesell, 2004), for example 17-(allylamino)-17-desmethoxy geldanamycin (17-AAG, 12) (Hostein et al., 2001; Neckers, 2002; Nimmanapalli et al., 2003; Vasilevskaya et al., 2003; Smith-Jones et al., 2004) and 17-desmethoxy-17-N,N-dimethylaminoethylamino-geldanamycin (17-DMAG, 13) (Egorin et al., 2002; Jez et al., 2003). More recently geldanamycin was derivatised on the 17-position to create 17-geldanamycin amides, carbamates, ureas and 17-arylgeldanamycin (Le Brazidec et al., 2003). A library of over sixty 17-alkylamino-17-demethoxygeldanamycin analogues has been reported and tested for their affinity for Hsp90 and water solubility (Tian et al., 2004). A further approach to reduce the toxicity of geldanamycin is the selective targeting and delivering of an active geldanamycin compound into malignant cells by conjugation to a tumour-targeting monoclonal antibody (Mandler et al., 2000).

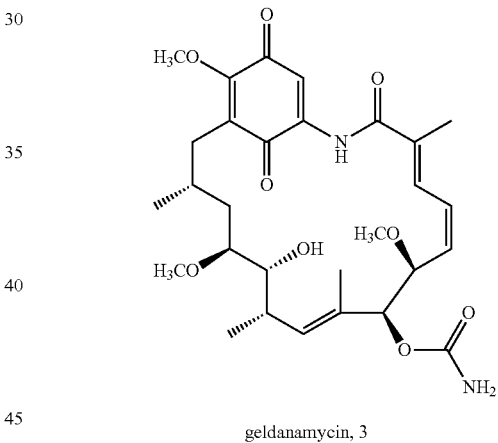

geldanamycin, 3

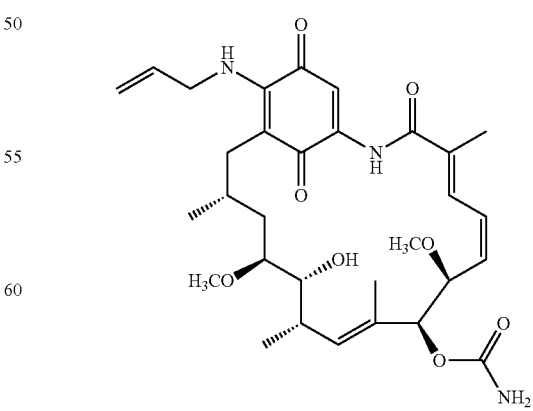

17-AAG, 12

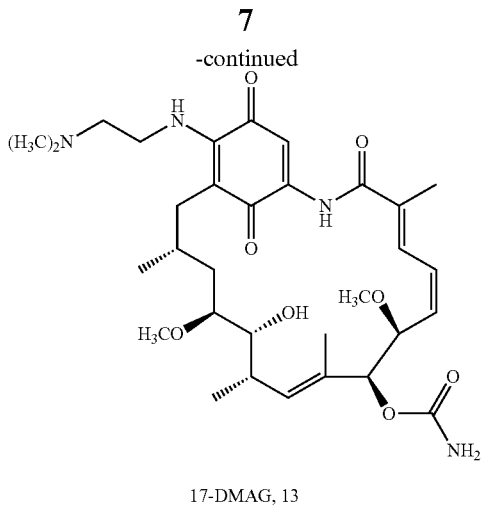

17-DMAG, 13

Whilst many of these derivatives exhibit reduced hepatotoxicity they still have only limited water solubility. For example 17-AAG requires the use of a solubilising carrier (e.g. Cremophore®, DMSO-egg lecithin), which itself may result in side-effects in some patients (Hu et al., 2004).

Most of the ansamycin class of Hsp90 inhibitors bear the common structural moiety: the benzoquinone which is a Michael acceptor that can readily form covalent bonds with nucleophiles such as proteins, glutithion, etc. The benzoquinone moiety also undergoes redox equilibrium with dihydroquinone, during which oxygen radicals are formed, which give rise to further unspecific toxicity (Dikalov et al., 2002).

Therefore, there remains a need to identify novel ansamycin derivatives, which may have utility in the treatment of cancer and/or B-cell malignancies, preferably such ansamycins have improved water solubility, an improved pharmacological profile and reduced side-effect profile for administration. The present invention discloses novel ansamycin analogues generated by biotransformation and optionally genetic engineering of the parent producer strain. In particular the present invention discloses novel 18,21-didesoxy-ansamycin analogues and other ansamycin analogues, which generally may have improved pharmaceutical properties compared with the presently available ansamycins; in particular they are expected show improvements in respect of one or more of the following properties: activity against different cancer sub-types, toxicity, water solubility, metabolic stability, bioavailability and formulation ability. Preferably the ansamycin analogues (such as 18,21-didesoxy-ansamycin analogues) show improved bioavailability.

SUMMARY OF THE INVENTION

In the present invention non-natural starter units have been fed to a geldanamycin producing strain, optionally in combination with targeted inactivation or deletion of the genes responsible for the post-PKS modifications of geldanamycin, and optionally with the introduction of appropriate post-PKS genes to effect post-PKS modifications in order to produce novel ansamycin analogues formed by incorporation of a non natural starter unit and, for example, which results in 18,21-didesoxy-ansamycin compounds which may optionally be substituted by fluorine or other substituents. Optionally the genes or regulators responsible for starter unit (starter acid) biosynthesis may be manipulated by targeted inactivation or deletion or modified by other means such as exposing cells to UV radiation and selection of the phenotype indicating that starter unit biosynthesis has been disrupted. The approach may be applied to other ansamycins such as herbimycin and reblastatin as well as autolytimycin. The optional targeting of the post-PKS genes may occur via a variety of mechanisms, e.g. by integration, targeted deletion of a region of the geldanamycin cluster including all or some of the post-PKS genes optionally followed by insertion of gene(s) or other methods of rendering the post-PKS genes or their encoded enzymes non-functional e.g. chemical inhibition, site-directed mutagenesis or mutagenesis of the cell for example by the use of UV radiation. Additionally, post-PKS genes from the geldanamycin cluster or another ansamycin cluster such as, but not limited to the macbecin, herbimycin, reblastatin or TAN clusters may be reintroduced to effect specific post-PKS modifications. As a result, the present invention provides ansamycin analogues such as 18,21-didesoxy-ansamycin analogues, methods for the preparation of these compounds, and methods for the use of these compounds in medicine or as intermediates in the production of further compounds.

Therefore, in a first aspect the present invention provides analogues of geldanamycin or other ansamycins which are lacking the usual starter unit, and which have instead incorporated a starter unit which, for example, results in 18,21-didesoxy-ansamycin compounds which may optionally be substituted by fluorine or other substituents.

Thus in one aspect of the invention there is provided a compound of formula (I) or a pharmaceutically acceptable salt thereof:

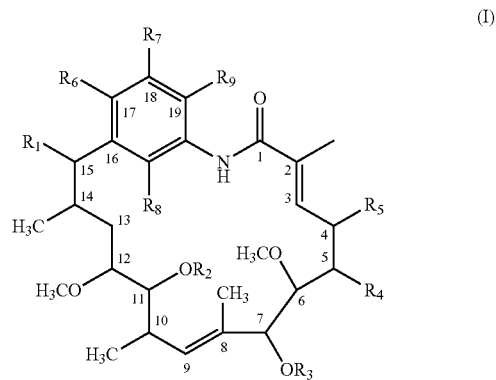

(I)

wherein:
$R_1$ represents H, OH, OMe;
$R_2$ represents H or Me;
$R_3$ represents H or $CONH_2$;
$R_4$ and $R_5$ either both represent H or together they represent a bond (i.e. C4 to C5 is a double bond);
$R_6$ represents H, F, OH, OMe, Br, Cl, $CF_3$, $CH_3$, SH, $CH_2CH_3$ or $NR_{10a}R_{11a}$;
$R_7$ represents H, F, OH, OMe, Br, Cl, $CF_3$, $CH_3$, SH, $CH_2CH_3$ or $NR_{10b}R_{11b}$;
$R_8$ represents H, F, OH, OMe, Br, Cl, $CF_3$, $CH_3$, SH, $CH_2CH_3$ or $NR_{10c}R_{11c}$;
$R_9$ represents H, F, OH, OMe, Br, Cl, $CF_3$, $CH_3$, SH, $CH_2CH_3$ or $NR_{10d}R_{11d}$;
$R_{10a}$, $R_{11a}$, $R_{10b}$, $R_{11b}$, $R_{10c}$, $R_{11c}$, $R_{10d}$, $R_{11d}$ independently represent H, $CH_3$ or $CH_2CH_3$;
provided however that:
(i) when $R_6$ represents H, $R_7$ represents OH and $R_8$ represents OH then $R_9$ does not represent H;
(ii) when $R_7$ represents OH, $R_8$ represents H and $R_9$ represent H, then $R_6$ does not represent H, OH or OMe; and (iii) when R₇ represents OMe, R₈ represent H and R₉ represents H, then R₆ does not represent OMe.

The compound of proviso (i) is 18,21-dihydrogeldanamycin, a known compound.

The compounds of provisos (ii) and (iii) are disclosed in WO2005/061461.

Suitably:
(iv) when $R_6$ represents H, OH, or OMe, $R_7$ represents H and $R_8$ represents H then $R_9$ does not represent OH, Cl or NH₂; and
(v) when $R_6$ represents H, OH, or OMe, $R_8$ represents H and $R_9$ represents H then $R_7$ does not represent NH₂.

Suitably
(vi) when $R_6$ represents H or OH, then $R_7$, $R_8$ and $R_9$ do not all represent H.

The compounds of proviso (vi) are disclosed in Kim et al ChemBioChem (2007) 8, 1491-1494. However they are also disclosed in an earlier patent application filed by the present inventors.

In a more specific aspect the present invention provides 18,21-didesoxy-ansamycin analogues according to the formula (IA) below, or a pharmaceutically acceptable salt thereof:

(IA)

wherein:
$R_1$ represents H, OH, OMe;
$R_2$ represents H or Me;
$R_3$ represents H or CONH₂;
$R_4$ and $R_5$ either both represent H or together they represent a bond (i.e. C4 to C5 is a double bond);
$R_6$ represents H, OH, OMe or F;
$R_7$ represents H or F;
$R_8$ represents H or F.

Ansamycin analogues such as 18,21-didesoxy-ansamycin analogues are also referred to herein as "compounds of the invention", such terms are used interchangeably herein.

The above structure shows a representative tautomer and the invention embraces all tautomers of the compounds of formula (I) for example keto compounds where enol compounds are illustrated and vice versa.

The invention embraces all stereoisomers of the compounds defined by structure (I) as shown above.

In a further aspect, the present invention provides ansamycin analogues such as compounds of formula (I) or a pharmaceutically acceptable salt thereof, for use as a pharmaceutical.

DEFINITIONS

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

The term "18,21-didesoxy-ansamycin analogue" as used in this application refers to compounds according to the formula (IA).

As used herein, the term "homologue(s)" refers a homologue of a gene or of a protein encoded by a gene disclosed herein from either an alternative macbecin biosynthetic cluster from a different macbecin producing strain or a homologue from an alternative ansamycin biosynthetic gene cluster e.g. from geldanamycin, herbimycin, autolytimycin or reblastatin. Such homologue(s) encode a protein that performs the same function of can itself perform the same function as said gene or protein in the synthesis of macbecin or a related ansamycin polyketide. Preferably, such homologue(s) have at least 40% sequence identity, preferably at least 60%, at least 70%, at least 80%, at least 90% or at least 95% sequence identity to the sequence of the particular gene disclosed herein (Table 3, SEQ ID NO: 11 which is a sequence of all the genes in the cluster, from which the sequences of particular genes may be deduced). Percentage identity may be calculated using any program known to a person of skill in the art such as BLASTn or BLASTp, available on the NCBI website.

As used herein, the term "cancer" refers to a benign or malignant new growth of cells in skin or in body organs, for example but without limitation, breast, prostate, lung, kidney, pancreas, brain, stomach or bowel. A cancer tends to infiltrate into adjacent tissue and spread (metastasize) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer and ovarian cancer.

As used herein the term "B-cell malignancies" includes a group of disorders that include chronic lymphocytic leukaemia (CLL), multiple myeloma, and non-Hodgkin's lymphoma (NHL). They are neoplastic diseases of the blood and blood forming organs. They cause bone marrow and immune system dysfunction, which renders the host highly susceptible to infection and bleeding.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described in Egorin et al. (2002).

The term "water solubility" as used in this application refers to solubility in aqueous media, e.g. phosphate buffered saline (PBS) at pH 7.3.

The term "ansamycin producing strain" as used in this application refers to strains, for example wild type strains as exemplified by a streptomycete such as geldanamycin producing strains, herbimycin producing strains, reblastatin producing strains and autolytimycin producing strains. Thus examples include *Streptomyces hygroscopicus* subsp. *geldanus* NRRL3602 or *Streptomyces* sp. DSM4137 or *Streptomyces violaceusniger* DSM40699 which produce ansamycins such as geldanamycin or herbimycins (e.g. herbimycin A, B or C) and *Streptomyces* sp. S6699 or *Streptomyces autolyticus* JX-47 which produce ansamycins such as or reblastatin or autolytimycin when cultured under suitable conditions, for example when fed the natural starter feed 3-amino-5-hydroxybenzoic acid.

Thus the term "geldanamycin producing strain" as used in this application refers to strains, for example wild type strains as exemplified by a streptomycete such as *Streptomyces hygroscopicus* subsp. *geldanus* NRRL3602 or *Streptomyces* sp. DSM4137 or *Streptomyces violaceusniger* DSM40699 which produce geldanamycin when cultured under suitable conditions, for example when fed the natural starter feed 3-amino-5-hydroxybenzoic acid.

The term "herbimycin producing strain" as used in this application refers to strains, for example wild type strains as exemplified by *Streptomyces hygroscopicus* AM-3672, which produce herbimycins e.g. herbimycin A, B or C when cultured under suitable conditions, for example when fed the natural starter feed 3-amino-5-hydroxybenzoic acid.

As used herein the term "post-PKS genes(s)" refers to the genes required for post-polyketide synthase modifications of the polyketide, for example but without limitation monooxygenases, O-methyltransferases and carbamoyltransferases. Specifically, in the macbecin system these modifying genes include mbcM, mbcN, mbcP, mbcMT1, mbcMT2 and mbcP450.

As used herein the term "starter unit biosynthesis gene(s)" refers to the genes required for the production of the starter unit naturally incorporated, 3-amino-5-hydroxybenzoic acid (AHBA). Specifically, in the macbecin system these starter unit biosynthesis genes include AHk (AHBA kinase), Adh (aDHQ dehydrogenase), AHs (AHBA synthase), OX (oxidoreductase), PH (Phosphatase). Specifically in the geldanamycin system the gene gdmO is proposed to to encode the amino dehydroquinate synthase needed for AHBA synthesis (Rascher et al., 2003) and in the herbimycin system hbmO has been identified (Rascher et al., 2005). Other strains that produce AHBA also contain AHBA biosynthesis genes.

The pharmaceutically acceptable salts of compounds of the invention such as the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both compounds of formula (I) and their pharmaceutically acceptable salts.

DESCRIPTION OF THE INVENTION

Figure 1:
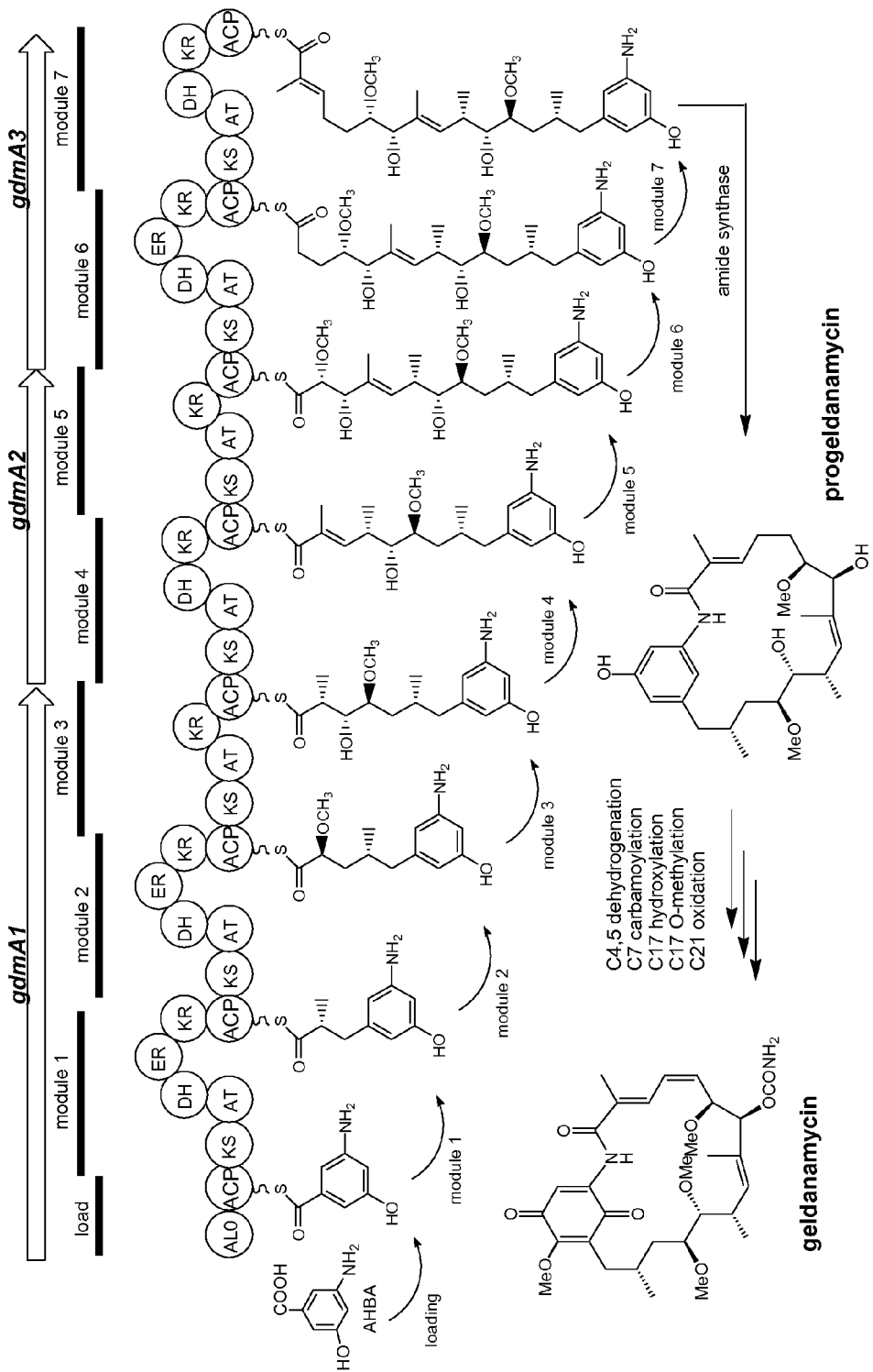
FIG. 1: Representation of the biosynthesis of geldanamycin showing the first putative enzyme free intermediate, progeldanamycin and the post-PKS processing to geldanamycin. The list of PKS processing steps in the figure is not intended to represent the order of events. The following abbreviations are used for particular genes in the cluster: AL0—AHBA loading domain; ACP—Acyl Carrier Protein; KS—β-ketosynthase; AT—acyl transferase; DH—dehydratase; ER—enoyl reductase; KR—β-ketoreductase.

The present invention provides ansamycin analogues, as set out above, methods for the preparation of these compounds, methods for the use of these compounds in medicine and the use of these compounds as intermediates or templates for further semi-synthetic derivatisation.

Suitably $R_1$ represents H or OH. In one embodiment $R_1$ represents H. In another embodiment $R_1$ represents OH.

Suitably $R_2$ represents H.

Suitably $R_3$ represents $CONH_2$.

In one embodiment suitably $R_4$ and $R_5$ together represent a bond

In another embodiment, suitably $R_4$ and $R_5$ each represent H.

In one embodiment, suitably $R_1$ represents H, $R_2$ represents H, $R_3$ represents $CONH_2$ and $R_4$ and $R_5$ each represent H.

In one embodiment, suitably $R_1$ represents OH, $R_2$ represents H, $R_3$ represents $CONH_2$ and $R_4$ and $R_5$ each represent H.

In one embodiment, suitably $R_1$ represents H, $R_2$ represents H, $R_3$ represents $CONH_2$, $R_4$ and $R_5$ each represent H and $R_6$ represents OH.

Suitably $R_6$ represents H, F, Me, Br, Cl, OH, OMe, $NH_2$, more suitably H, F, Me, Br, Cl, OH or OMe, yet more suitably H or F.

Alternatively suitably $R_6$ represents $CF_3$ or $CH_2CH_3$.

Suitably $R_7$ represents H, F, OH, OMe, Br, Cl or $NH_2$, more suitably H, F, OH, OMe, Br or Cl, yet more suitably H, F, OH or OMe, especially OH (or alternatively H or F).

Suitably $R_8$ represents H, F, Me, Cl, Br, OH or $NH_2$, more suitably H, F, Me, Cl, Br or OH, yet more suitably H or F.

Suitably $R_9$ represents H, F, Me, Cl, Br, OH or $NH_2$, more suitably H, F, Me, Cl, Br or OH, yet more suitably H or F especially H.

Suitably $R_{10a}$, $R_{11a}$, $R_{10b}$, $R_{11b}$, $R_{10c}$, $R_{11c}$, $R_{10d}$, $R_{11d}$ represent H.

Suitably when $R_7$ represents OH, then one or more of $R_6$, $R_8$ or $R_9$ represents F, Br, Me or $NH_2$, and the remainder represent H Suitably if $R_6$ represents Me, then $R_7$ represents OH, H or F, and $R_8$ and $R_9$ represent H Suitably if $R_6$ represents $CF_3$, then $R_7$ represents OH, H or F, and $R_8$ and $R_9$ represent H Suitably if $R_6$ represents $CH_2CH_3$, then $R_7$ represents OH, H or F, and $R_8$ and $R_9$ represent H In one suitable embodiment of the invention R₁ represents H, R₂ represents H, R₃ represents CONH₂, R₄, R₅, R₆, R₇ and R₈ each represent H, e.g. as represented by the following structure,

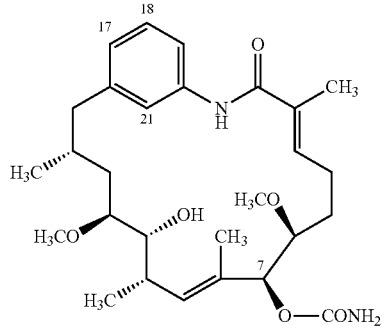 [SMILES: CO[C@H]1C[C@H](C)Cc2cccc(c2)NC(=O)/C(C)=C/CC[C@H](OC)[C@@H](OC(N)=O)/C(C)=C/[C@H](C)[C@H]1O]

In another suitable embodiment of the invention R₁ represents H, R₂ represents H, R₃ represents CONH₂, R₄ and R₅ each represent H, R₆ represents OH and R₇ and R₈ each represent H, e.g. as represented in the following structure,

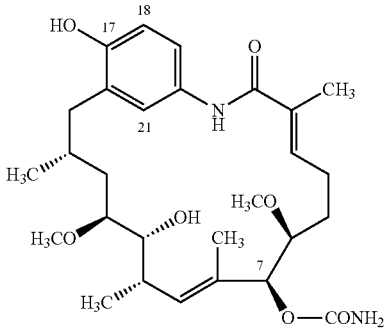

In another suitable embodiment of the invention R₁ represents H, R₂ represents H, R₃ represents CONH₂, R₄ and R₅ each represent H, R₆ represents F and R₇ and R₈ each represent H, e.g. as represented by the following structure,

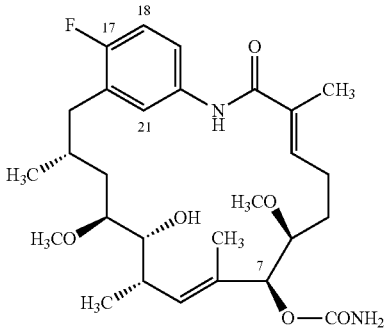 [SMILES: CO[C@H]1C[C@H](C)Cc2cc(ccc2F)NC(=O)/C(C)=C/CC[C@H](OC)[C@@H](OC(N)=O)/C(C)=C/[C@H](C)[C@H]1O]

In another suitable embodiment of the invention R₁ represents OH, R₂ represents H, R₃ represents CONH₂, R₄ and R₅ each represent H, R₆ represents F and R₇ and R₈ each represent H, e.g. as represented in the following structure,

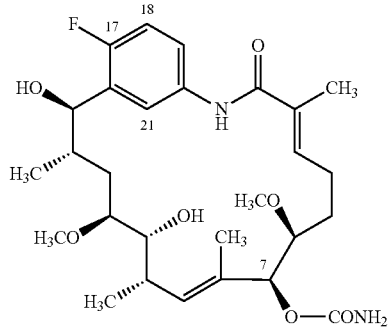

In another suitable embodiment of the invention R₁ represents H, R₂ represents H, R₃ represents CONH₂, R₄ and R₅ each represent H, R₆ represents H, R₇ represents F and R₈ represents H, e.g. as represented in the following structure,

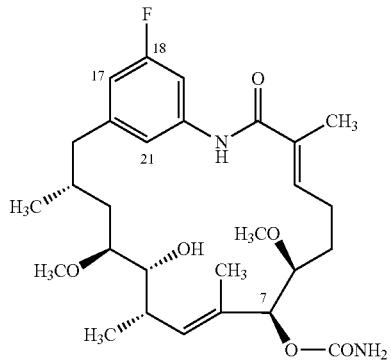 [SMILES: CO[C@H]1C[C@H](C)Cc2cc(F)cc(c2)NC(=O)/C(C)=C/CC[C@H](OC)[C@@H](OC(N)=O)/C(C)=C/[C@H](C)[C@H]1O]

In another suitable embodiment of the invention R₁ represents H, R₂ represents H, R₃ represents CONH₂, R₄ and R₅ each represent H, R₆ represents OH, R₇ represents F and R₈ represents H, e.g. as represented in the following structure,

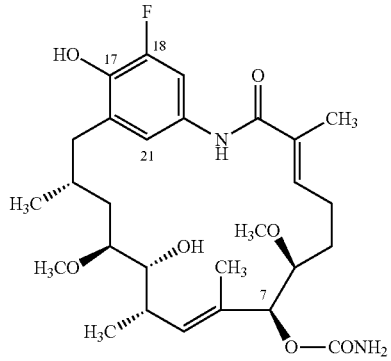 [SMILES: CO[C@H]1C[C@H](C)Cc2cc(cc(F)c2O)NC(=O)/C(C)=C/CC[C@H](OC)[C@@H](OC(N)=O)/C(C)=C/[C@H](C)[C@H]1O]

In another suitable embodiment of the invention $R_1$ represents OH, $R_2$ represents H, $R_3$ represents $CONH_2$, $R_4$ and $R_5$ each represent H, $R_6$ represents H, $R_7$ represents F and $R_8$ represents H e.g. as represented in the following structure,

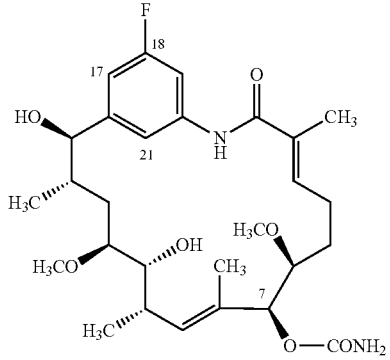 [SMILES: CO[C@H]1C[C@H](C)[C@@H](O)c2cc(F)cc(c2)NC(=O)/C(C)=C/CC[C@H](OC)[C@@H](OC(N)=O)/C(C)=C/[C@H](C)[C@H]1O]

In another suitable embodiment of the invention $R_1$ represents H, $R_2$ represents H, $R_3$ represents $CONH_2$, $R_4$ and $R_5$ each represent H, $R_6$ and $R_7$ each represent F and $R_8$ represents H, e.g. as represented in the following structure,

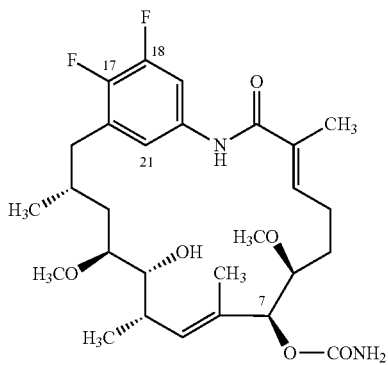 [SMILES: CO[C@H]1C[C@H](C)Cc2cc(cc(F)c2F)NC(=O)/C(C)=C/CC[C@H](OC)[C@@H](OC(N)=O)/C(C)=C/[C@H](C)[C@H]1O]

In another suitable embodiment of the invention $R_1$ represents OH, $R_2$ represents H, $R_3$ represents $CONH_2$, $R_4$ and $R_5$ each represent H, $R_6$ and $R_7$ each represent F and $R_8$ represents H e.g. as represented in the following structure,

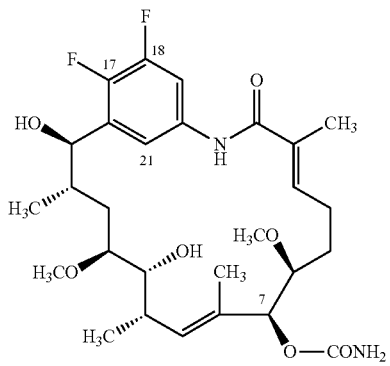 [SMILES: CO[C@H]1C[C@H](C)[C@@H](O)c2cc(cc(F)c2F)NC(=O)/C(C)=C/CC[C@H](OC)[C@@H](OC(N)=O)/C(C)=C/[C@H](C)[C@H]1O]

In another suitable embodiment of the invention $R_1$ represents H, $R_2$ represents H, $R_3$ represents $CONH_2$, $R_4$ and $R_5$ each represent H, $R_6$, $R_7$ and $R_8$ each represent F, e.g. as represented in the following structure,

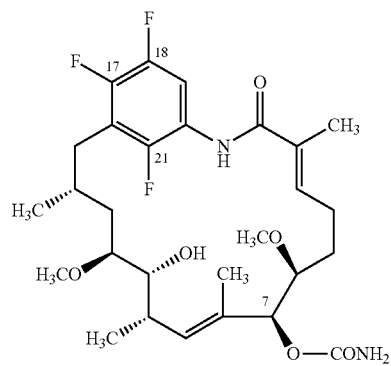 [SMILES: CO[C@H]1C[C@H](C)Cc2c(F)c(F)cc(c2F)NC(=O)/C(C)=C/CC[C@H](OC)[C@@H](OC(N)=O)/C(C)=C/[C@H](C)[C@H]1O]

In one embodiment of the invention $R_6$, $R_7$ and $R_8$ do not all represent H, and in particular at least one of $R_6$, $R_7$ and $R_8$ represents F.

In another suitable embodiment of the invention $R_1$ represents OH, $R_2$ represents H, $R_3$ represents $CONH_2$, $R_4$ and $R_5$ each represent H, $R_6$ represents F, $R_7$ represents OH and $R_8$ represents H e.g. as represented in the following structure,

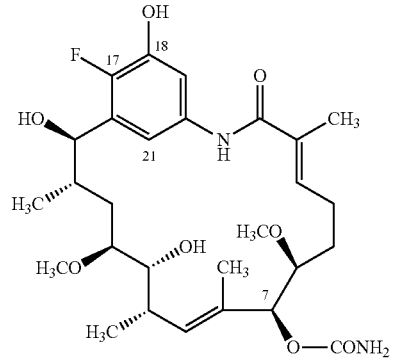 [SMILES: CO[C@H]1C[C@H](C)[C@@H](O)c2cc(cc(O)c2F)NC(=O)/C(C)=C/CC[C@H](OC)[C@@H](OC(N)=O)/C(C)=C/[C@H](C)[C@H]1O]

In another suitable embodiment of the invention $R_1$ represents OH, $R_2$ represents H, $R_3$ represents $CONH_2$, $R_4$ and $R_5$ each represent H, $R_6$ represents Me, $R_7$ represents OH and $R_8$ represents H e.g. as represented in the following structure,

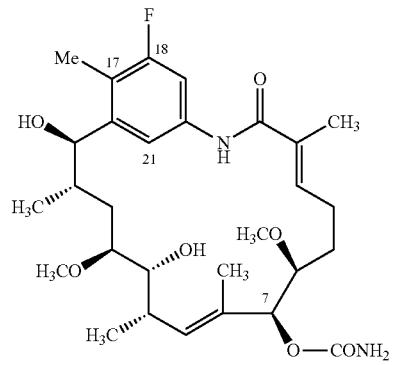 [SMILES: CO[C@H]1C[C@H](C)[C@@H](O)c2cc(cc(F)c2C)NC(=O)/C(C)=C/CC[C@H](OC)[C@@H](OC(N)=O)/C(C)=C/[C@H](C)[C@H]1O]

In another suitable embodiment of the invention R₁ represents OH, R₂ represents H, R₃ represents CONH₂, R₄ and R₅ each represent H, R₆ represents CF₃, R₇ represents OH and R₈ represents H e.g. as represented in the following structure,

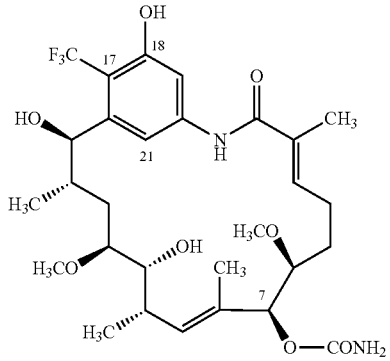 [SMILES: CO[C@H]1C[C@H](C)[C@@H](O)c2cc(cc(O)c2C(F)(F)F)NC(=O)/C(C)=C/CC[C@H](OC)[C@@H](OC(N)=O)/C(C)=C/[C@H](C)[C@H]1O]

In another suitable embodiment of the invention R₁ represents OH, R₂ represents H, R₃ represents CONH₂, R₄ and R₅ each represent H, R₆ represents CH₂CH₃, R₇ represents OH and R₈ represents H e.g. as represented in the following structure,

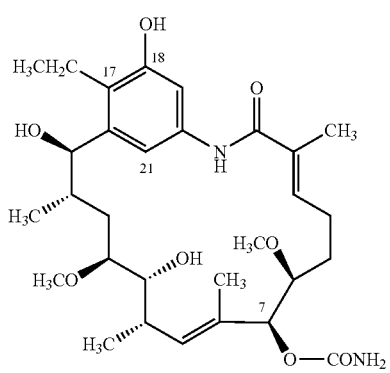

In another suitable embodiment of the invention R₁ represents H, R₂ represents H, R₃ represents CONH₂, R₄ and R₅ each represent H, R₆ represents F, R₇ represents OH and R₈ represents H e.g. as represented in the following structure,

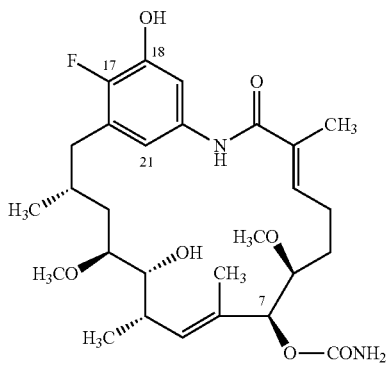 [SMILES: CO[C@H]1C[C@H](C)Cc2cc(cc(O)c2F)NC(=O)/C(C)=C/CC[C@H](OC)[C@@H](OC(N)=O)/C(C)=C/[C@H](C)[C@H]1O]

In another suitable embodiment of the invention R₁ represents H, R₂ represents H, R₃ represents CONH₂, R₄ and R₅ each represent H, R₆ represents Me, R₇ represents OH and R₈ represents H e.g. as represented in the following structure,

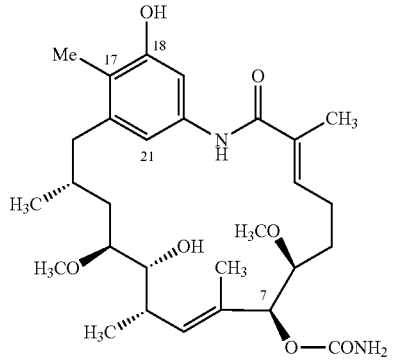 [SMILES: CO[C@H]1C[C@H](C)Cc2cc(cc(O)c2C)NC(=O)/C(C)=C/CC[C@H](OC)[C@@H](OC(N)=O)/C(C)=C/[C@H](C)[C@H]1O]

In another suitable embodiment of the invention R₁ represents H, R₂ represents H, R₃ represents CONH₂, R₄ and R₅ each represent H, R₆ represents CF₃, R₇ represents OH and R₈ represents H e.g. as represented in the following structure,

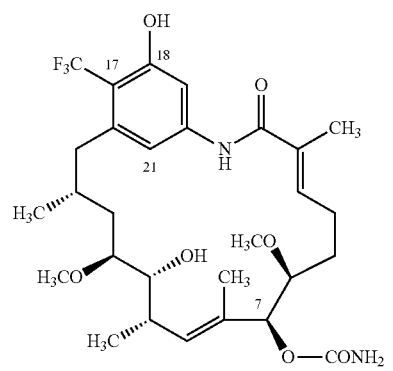 [SMILES: CO[C@H]1C[C@H](C)Cc2cc(cc(O)c2C(F)(F)F)NC(=O)/C(C)=C/CC[C@H](OC)[C@@H](OC(N)=O)/C(C)=C/[C@H](C)[C@H]1O]

In another suitable embodiment of the invention R₁ represents H, R₂ represents H, R₃ represents CONH₂, R₄ and R₅ each represent H, R₆ represents CH₂CH₃, R₇ represents OH and R₈ represents H e.g. as represented in the following structure,

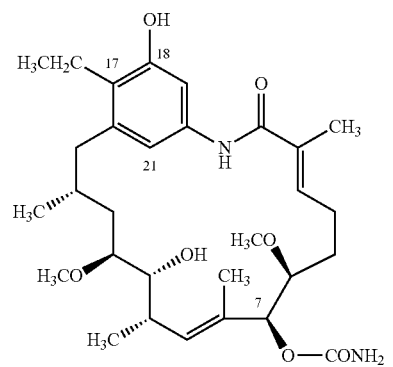

In another suitable embodiment of the invention $R_1$ represents H, $R_2$ represents H, $R_3$ represents $CONH_2$, $R_4$ and $R_5$ each represent H, $R_6$ represents OMe, $R_7$ represents H and $R_8$ represents OH e.g. as represented in the following structure,

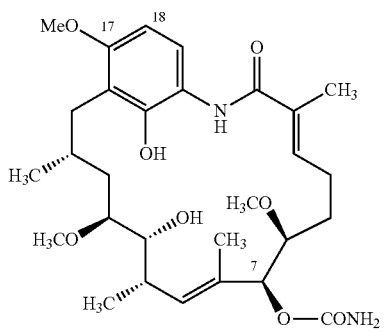

In another suitable embodiment of the invention $R_1$ represents H, $R_2$ represents H, $R_3$ represents $CONH_2$, $R_4$ and $R_5$ each represent H, $R_6$ represents OH, $R_7$ represents H and $R_8$ represents OH e.g. as represented in the following structure,

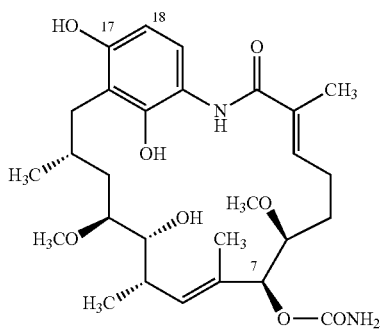

In another suitable embodiment of the invention $R_1$ represents H, $R_2$ represents H, $R_3$ represents $CONH_2$, $R_4$ and $R_5$ each represent H, $R_6$ represents H, $R_7$ represents H and $R_8$ represents OH e.g. as represented in the following structure,

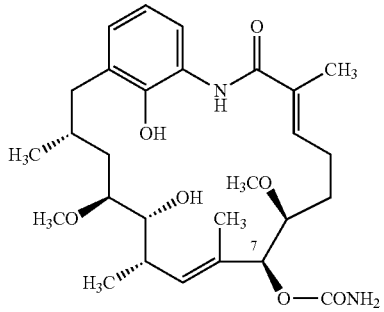 [SMILES: CO[C@H]1C[C@H](C)Cc2cccc(c2O)NC(=O)/C(C)=C/CC[C@H](OC)[C@@H](OC(N)=O)/C(C)=C/[C@H](C)[C@H]1O]

In another suitable embodiment of the invention $R_1$ represents H, $R_2$ represents H, $R_3$ represents $CONH_2$, $R_4$ and $R_5$ each represent H, $R_6$ represents H, $R_7$ represents F and $R_8$ represents OH e.g. as represented in the following structure,

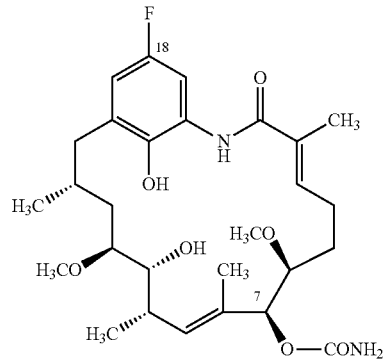 [SMILES: CO[C@H]1C[C@H](C)Cc2cc(Cl)cc(c2O)NC(=O)/C(C)=C/CC[C@H](OC)[C@@H](OC(N)=O)/C(C)=C/[C@H](C)[C@H]1O]

In another suitable embodiment of the invention $R_1$ represents H, $R_2$ represents H, $R_3$ represents $CONH_2$, $R_4$ and $R_5$ each represent H, $R_6$ represents H, $R_7$ represents Cl and $R_8$ represents OH e.g. as represented in the following structure,

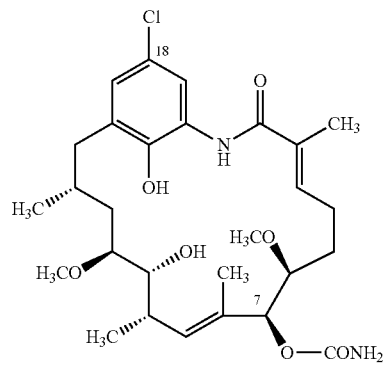

In another suitable embodiment of the invention $R_1$ represents H, $R_2$ represents H, $R_3$ represents $CONH_2$, $R_4$ and $R_5$ each represent H, $R_6$ represents H, $R_7$ represents OH and $R_8$ represents F e.g. as represented in the following structure,

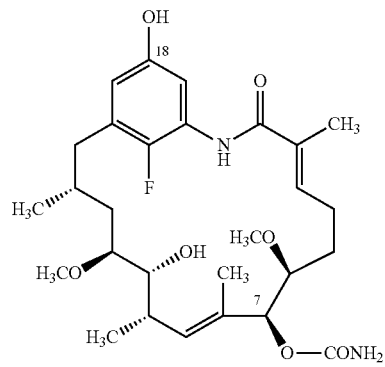 [SMILES: CO[C@H]1C[C@H](C)Cc2cc(O)cc(c2F)NC(=O)/C(C)=C/CC[C@H](OC)[C@@H](OC(N)=O)/C(C)=C/[C@H](C)[C@H]1O]

In another suitable embodiment of the invention $R_1$ represents H, $R_2$ represents H, $R_3$ represents $CONH_2$, $R_4$ and $R_5$ each represent H, $R_6$ represents H, $R_7$ represents OH and $R_8$ represents Cl e.g. as represented in the following structure,

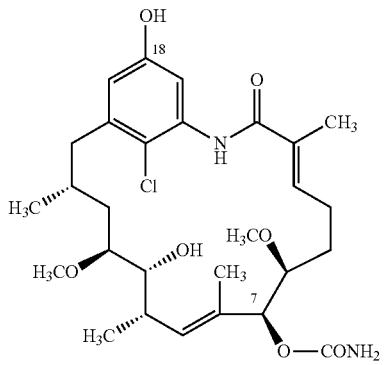 [SMILES: CO[C@H]1C[C@H](C)Cc2cc(O)cc(c2Cl)NC(=O)/C(C)=C/CC[C@H](OC)[C@@H](OC(N)=O)/C(C)=C/[C@H](C)[C@H]1O]

In another suitable embodiment of the invention $R_1$ represents H, $R_2$ represents H, $R_3$ represents $CONH_2$, $R_4$ and $R_5$ each represent H, $R_6$ represents OMe, $R_7$ represents F and $R_8$ represents OH e.g. as represented in the following structure,

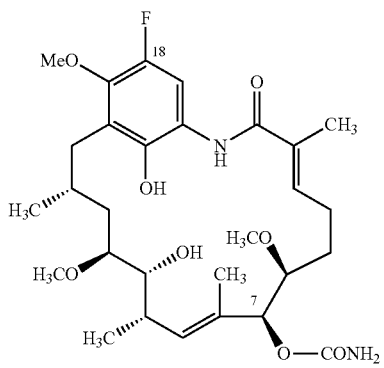 [SMILES: COc1c(F)cc2c(O)c1C[C@@H](C)C[C@H](OC)[C@H](O)[C@@H](C)/C=C(\C)[C@H](OC(N)=O)[C@@H](OC)CC/C=C(\C)C(=O)N2]

In another embodiment of the invention $R_6$, $R_7$ and $R_8$ all represent H.

In another embodiment $R_7$ and $R_8$ do not represent OH, $R_9$ represents H and one or more of $R_6$, $R_7$ and $R_8$ represent F.

In another embodiment of the invention when $R_1$ represents H, $R_2$ represents H, $R_3$ represents $CONH_2$, $R_4$ and $R_5$ represents H, $R_6$ represents H and $R_7$ represents H then $R_8$ does not represent H.

Figure 3:
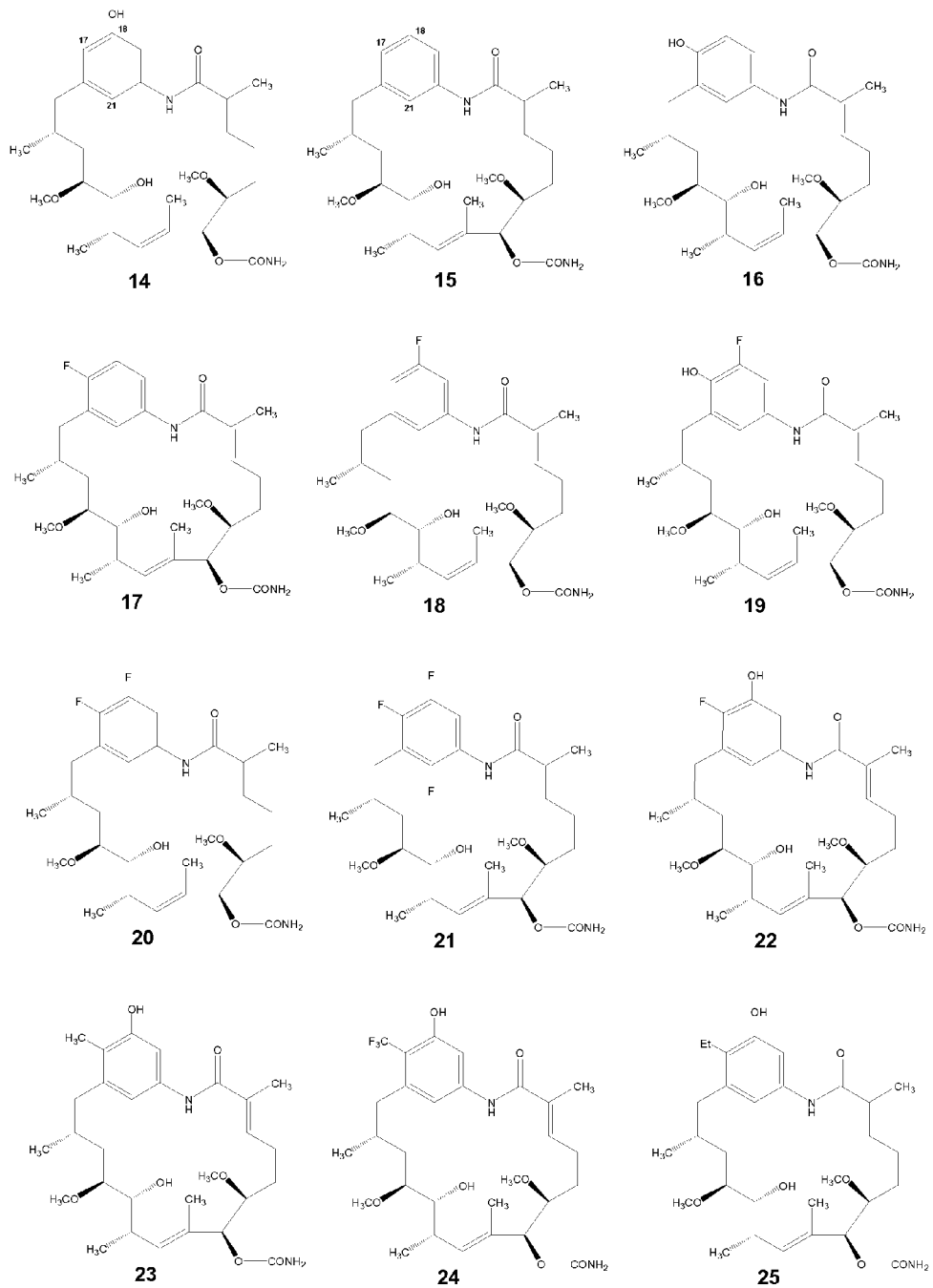
FIG. 3: Structures of the compounds (14-25) described in the Examples.
Figure 4:
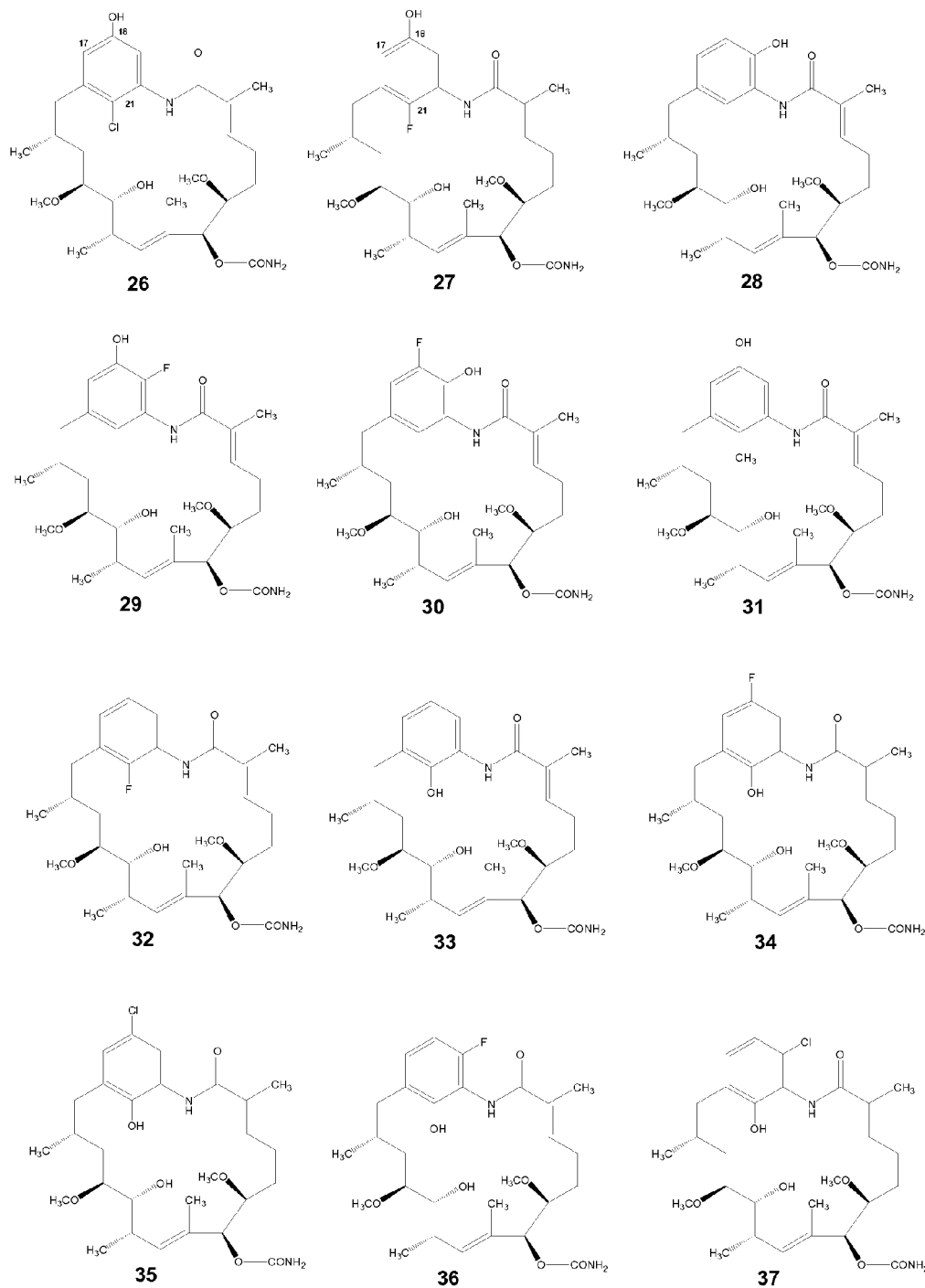
FIG. 4: Structures of the compounds (26-37) described in the Examples.

Further suitable embodiments are described in the Examples and illustrated in FIGS. 3 and 4.

Figure 2:
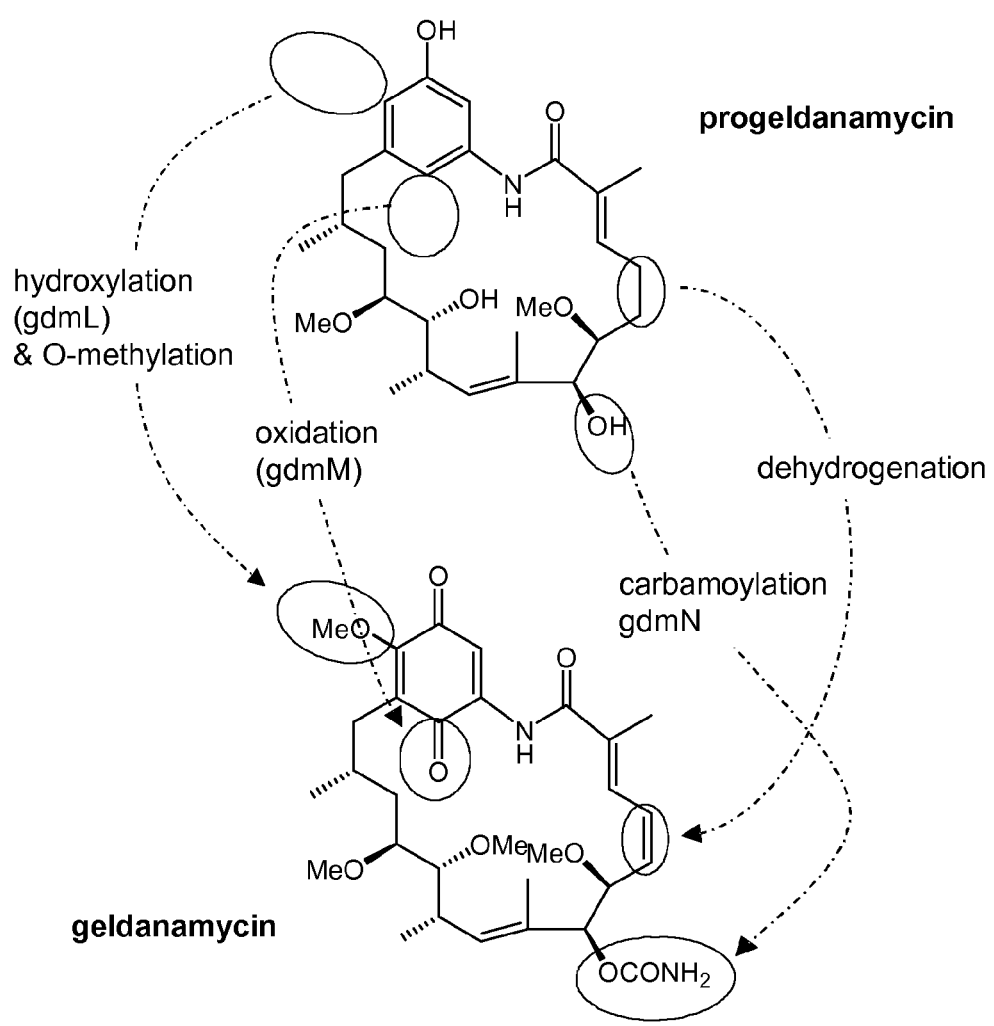
FIG. 2: Depiction of the sites of post-PKS processing of pro-geldanamycin to give geldanamycin.

The preferred stereochemistry of the non-hydrogen sidechains to the ansa ring is as shown in FIGS. 1 and 2 below (that is to say the preferred stereochemistry follows that of geldanamycin).

The present invention also provides for the use of an ansamycin analogue as a substrate for further modification either by biotransformation or by synthetic chemistry. In one aspect the present invention provides an ansamycin analogue for use as a medicament. In a specific embodiment the present invention provides an ansamycin analogue for use in the treatment of cancer, B-cell malignancies, malaria, fungal infection, diseases of the central nervous system and neurodegenerative diseases, diseases dependent on angiogenesis, autoimmune diseases and/or as a prophylactic pretreatment for cancer.

In another aspect the present invention provides for the use of an ansamycin analogue in the manufacture of a medicament. In a specific embodiment the present invention provides for the use of an ansamycin analogue in the manufacture of a medicament for the treatment of cancer, B-cell malignancies, malaria, fungal infection, diseases of the central nervous system and neurodegenerative diseases, diseases dependent on angiogenesis, autoimmune diseases and/or as a prophylactic pretreatment for cancer.

In a further embodiment the present invention provides a method of treatment of cancer, B-cell malignancies, malaria, fungal infection, diseases of the central nervous system and neurodegenerative diseases, diseases dependent on angiogenesis, autoimmune diseases or a prophylactic pretreatment for cancer, said method comprising administering to a patient in need thereof a therapeutically effective amount of an ansamycin analogue.

As noted above, compounds of the invention may be expected to be useful in the treatment of cancer and B-cell malignancies. Compounds of the invention and especially those which may have improved selectivity for Hsp90 and/or an improved toxicology profile and/or improved pharmacokinetics may also be effective in the treatment of other indications for example, but not limited to malaria, fungal infection, diseases of the central nervous system and neurodegenerative diseases, diseases dependent on angiogenesis, autoimmune diseases such as rheumatoid arthritis or as a prophylactic pretreatment for cancer.

Diseases of the central nervous system and neurodegenerative diseases include, but are not limited to, Alzheimer's disease, Parkinson's disease, Huntington's disease, prion diseases, spinal and bulbar muscular atrophy (SBMA) and amyotrophic lateral sclerosis (ALS).

Diseases dependent on angiogenesis include, but are not limited to, Age-related macular degeneration, diabetic retinopathy and various other ophthalmic disorders, atherosclerosis and rheumatoid arthritis.

Autoimmune diseases include, but are not limited to, rheumatoid arthritis, multiple sclerosis, type I diabetes, systemic lupus erythematosus and psoriasis, "Patient" embraces human and other animal (especially mammalian) subjects, preferably human subjects. Accordingly the methods and uses of the ansamycin analogues of the invention are of use in human and veterinary medicine, preferably human medicine.

The aforementioned compounds of the invention or a formulation thereof may be administered by any conventional method for example but without limitation they may be administered parenterally (including intravenous administration), orally, topically (including buccal, sublingual or transdermal), via a medical device (e.g. a stent), by inhalation, or via injection (subcutaneous or intramuscular). The treatment may consist of a single dose or a plurality of doses over a period of time.

Whilst it is possible for a compound of the invention to be administered alone, it is preferable to present it as a pharmaceutical formulation, together with one or more acceptable diluents or carriers. Thus there is provided a pharmaceutical composition comprising a compound of the invention together with one or more pharmaceutically acceptable diluents or carriers. The diluents(s) or carrier(s) must be "acceptable" in the sense of being compatible with the compound of the invention and not deleterious to the recipients thereof. Examples of suitable carriers are described in more detail below.

The compounds of the invention may be administered alone or in combination with other therapeutic agents. Coadministration of two (or more) agents may allow for significantly lower doses of each to be used, thereby reducing the side effects seen. There is also provided a pharmaceutical composition comprising a compound of the invention and a further therapeutic agent together with one or more pharmaceutically acceptable diluents or carriers.

In a further aspect, the present invention provides for the use of a compound of the invention in combination therapy with a second agent e.g. for the treatment of cancer or B-cell malignancies.

In one embodiment, a compound of the invention is co-administered with another therapeutic agent, for example a therapeutic agent for the treatment of cancer or B-cell malignancies. Preferred agents include, but are not limited to, the conventional chemotherapeutics such as bleomycin, capecitabine, cisplatin, cytarabine, cyclophosphamide, doxorubicin, 5-fluorouracil, gemcitabine, leucovorin, methotrexate, mitoxantone, the taxanes including paclitaxel and docetaxel, vincristine, vinblastine and vinorelbine; the hormonal therapies, anastrozole, goserelin, megestrol acetate, prenisone, tamoxifen and toremifene; the monoclonal antibody therapies such as trastuzumab (ani-Her2), cetuximab (ant-EGFR) and bevacizumab (anti-VEGF); and protein kinase inhibitors such as imatinib, dasatinib, gefitinib, erlotinib, lapatinib, temsirolimus; the proteasome inhibitors such as bortezomib; histone deacetylase (HDAC) inhibitors such as vorinostat; angiogenesis inhibitors such as sunitinib, sorafenib, lenalidomide. Additionally, a compound of the invention may be administered in combination with other therapies including, but not limited to, radiotherapy or surgery.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

The compounds of the invention may also be administered using medical devices known in the art. For example, in one embodiment, a pharmaceutical composition of the invention can be administered with a needleless hypodermic injection device, such as the devices disclosed in U.S. Pat. No. 5,399, 163; U.S. Pat. No. 5,383,851; U.S. Pat. No. 5,312,335; U.S. Pat. No. 5,064,413; U.S. Pat. No. 4,941,880; U.S. Pat. No. 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

In a further aspect the present invention provides methods for the production of ansamycin analogues.

Ansamycin polyketides for example geldanamycin and herbimycin are synthesised by polyketide biosynthetic clusters which are well known in the art. Geldanamycin can be considered to be biosynthesized in two stages. In the first stage the core-PKS genes assemble the macrolide core by the repeated assembly of simple carboxylic acid precursors to give a polyketide chain which is then cyclised to form the first enzyme-free intermediate "progeldanamycin", see FIG. 1. In the second stage a series of "post-PKS" tailoring enzymes (e.g. a cytochrome P450 monooxygenase, methyltransferases, FAD-dependent oxygenases and a carbamoyltransferase) act to add the various additional groups to the progeldanamycin template resulting in the final parent compound structure, see FIG. 2. The ansamycin analogues may be biosynthesized in a similar manner. This biosynthetic production may be exploited by biotransformation optionally combined with genetic engineering of suitable producer strains to result in the production of novel compounds.

Surprisingly the inventors have found that by feeding ansamycin producing strains with non-natural starter units (starter acids or analogues thereof such as esters), these starter units may be incorporated into ansamycin structures to produce novel ansamycin analogues.

Thus according to the invention there is provided a method for preparing an ansamycin analogue which comprises:
a) providing a strain that produces an ansamycin such as geldanamycin, a herbimycin (herbimycin A, B or C) or an analogue thereof when cultured under appropriate conditions
b) feeding a starter unit which is not AHBA to said strain such that the starter unit is incorporated into said ansamycin analogue;
c) culturing said strain under suitable conditions for the production of an ansamycin analogue; and
d) optionally isolating the compounds produced.

Suitably the strain of a) is characterised by being a strain which one or more AHBA biosynthesis genes have been deleted or inactivated. This may avoid competition for incorporation of a non-natural starter unit by AHBA which would decrease yield. Alternatively, the strain of a) may be mutated to lower the efficiency of AHBA biosynthesis. Suitably the conditions of step c) are such that the efficiency of AHBA biosynthesis is sub-optimal. Thus desirably AHBA is produced by the strain to a level which nevertheless allows incorporation of the fed non-natural starter unit. Typically the amount of incorporated fed non natural starter unit is >20%, preferably >50% of the total starter unit incorporation.

Suitably the starter unit is selected from

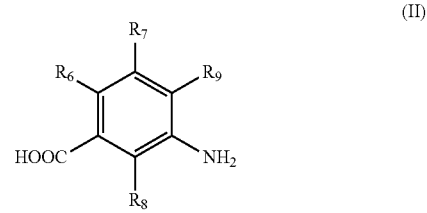

(II)

wherein $R_6$, $R_7$, $R_8$ and $R_9$ are as defined above.

or an analogue thereof in which the acid moiety is derivatised such as an ester (e.g. the methyl or ethyl ester).

Suitably the starter unit is not: 3,5-diamino benzoic acid, 3-amino-4-hydroxybenzoic acid or 3-amino-4-chlorobenzoic acid.

In one embodiment the starter unit is a compound of formula (II) in which $R_6$, $R_7$, $R_8$ and $R_9$ all represent H.

In another embodiment the starter unit is a compound of formula (II) in which $R_6$, $R_7$, $R_8$ and $R_9$ do not all represent H.

Further exemplary start units include, but are not limited to those compounds shown in the second columns of Tables 4 and 5 below, as well as appropriate derivatives thereof (such as salts and esters etc).

In one embodiment the strain is an ansamycin producing strain (e.g. a geldanamycin or herbimycin producing strain) and the starter unit is selected such that the strain produces a 18,21-didesoxy-ansamycin analogue.

In one embodiment the starter unit is selected such that the strain produces a 18,21-didesoxy-ansamycin analogue which is optionally substituted by fluorine.

In one embodiment the starter unit is selected such that the strain produces a 18,21-didesoxy-ansamycin analogue which is substituted by fluorine.

In another embodiment the strain is a macbecin producing strain and the starter unit is selected such that the strain produces a macbecin analogue which is not substituted at positions 18 or 21 of the benzene ring.

Suitably the method (i) further comprises the step of subjecting the product of step (d) to a process of chemical modification or biotransformation optionally followed by the step of isolating the resultant compounds or (ii) further comprises the step of subjecting the product of step (c) to a process of chemical modification or biotransformation prior to step (d).

According to another aspect of the invention there is provided a method for the generation of analogues such as 18,21-didesoxy-ansamycin analogues, said method comprising:

a) providing a first host strain that produces an ansamycin or an analogue thereof when cultured under appropriate conditions in which optionally one or more post-PKS genes have been deleted or inactivated and/or one or more starter unit biosynthesis genes have been deleted or inactivated;

b) feeding a non-natural starter unit to said strain c) culturing said modified host strain under suitable conditions for the production of ansamycin analogues such as 18,21-didesoxy-ansamycin analogues; and d) optionally isolating the compounds produced.

Suitably the fed starter unit is a starter acid.

In particular, the present invention provides a method of producing 18,21-didesoxy-ansamycin analogues said method comprising:

a) providing a first host strain that produces an ansamycin such as geldanamycin, herbimycins (e.g. herbimycin A, B or C) or an analogue thereof when cultured under appropriate conditions b) feeding a non-natural starter acid to said strain;

c) culturing said strain under suitable conditions for the production of 18,21-didesoxy-ansamycin analogues; and d) optionally isolating the compounds produced.

Suitably the method additionally comprises the steps of:

e) deleting or inactivating one or more of the starter unit biosynthesis genes, or a homologue thereof, said step usually occurring prior to step c).

Suitably the method additionally, or instead, comprises the step of:

f) deleting or inactivating one or more post-PKS genes, said step usually occurring prior to step c).

In step (a) by "a host strain that produces an ansamycin such as geldanamycin, herbimycins (e.g. herbimycin A, B or C) or an analogue thereof" includes a strain that produces an ansamycin such as geldanamycin, a herbimycin (e.g. herbimycin A, B or C) or the ansamycin compounds that are embraced by the definitions of $R_1$-$R_{11}$ when cultured under appropriate conditions. Appropriate conditions (and suitable conditions in step (c)) include the provision of a suitable starter feed and growth media of suitable composition (which will be known to a skilled person or may be determined by methods known per se).

For example the in step (a) the first host strain may produce geldanamycin or an analogue thereof when cultured under appropriate conditions.

Suitably the non-natural starter feed is a substituted benzoic acid (not being 3-amino-5-hydroxy-benzoic acid which is the natural starter acid), most suitably a 3-amino-benzoic acid optionally substituted further around the ring. Suitably the non-natural starter feed is 3-amino-benzoic acid substituted by none, one, two or three fluorine atoms.

In a suitable embodiment the non-natural starter acid feed is 3-amino benzoic acid.

In another suitable embodiment the non-natural starter acid feed is 5-amino-2-fluorobenzoic acid.

In another suitable embodiment the non-natural starter acid feed is 5-amino-3-fluorobenzoic acid.

In another suitable embodiment the non-natural starter acid feed is 5-amino-2,3-di-fluorobenzoic acid.

In another suitable embodiment the non-natural starter acid feed is 5-amino-2,3,6-tri-fluorobenzoic acid.

One skilled in the art will appreciate that there are alternative non-natural starter units that could be fed to the host strain to produce the same compound(s) for example, but not limited to, the methyl ester, the ethyl ester, the N-acetyl-cysteamine thioester of the substituted benzoic acid and the diketide analogue of the biosynthetic intermediate activated appropriately for incorporation for example as the N-acetyl-cysteamine thioester. Acid compounds may also be supplied as corresponding salt forms.

The host strain may, for example, be an ansamycin producing strain such as geldanamycin producing strain or a herbimycin producing strain. Alternatively, the host strain is an engineered strain based on an ansamycin producing strain such as a geldanamycin producing strain (or a herbimycin producing strain) in which one or more of the starter unit biosynthetic genes have been deleted or inactivated. In a further embodiment the host strain is an engineered strain based on an ansamycin producing strain in which one or more of the post-PKS genes have been deleted or inactivated In a further embodiment the host strain is an engineered strain based on an ansamycin producing strain in which gdmM has been deleted or inactivated.

In a further embodiment the host strain is an engineered strain based on an ansamycin producing strain in which the gdmM homologue and optionally further post-PKS genes have been deleted or inactivated.

In one embodiment of the invention the host strain is a geldanamycin producing strain.

In an alternative embodiment, the host strain is an engineered strain based on a geldanamycin producing strain in which one or more of the starter unit biosynthetic genes have been deleted or inactivated.

In a further embodiment the host strain is an engineered strain based on a geldanamycin producing strain in which one or more of the post-PKS genes have been deleted or inactivated In a further embodiment the host strain is an engineered strain based on a geldanamycin producing strain in which gdmM has been deleted or inactivated.

In a further embodiment the host strain is an engineered strain based on a geldanamycin producing strain in which gdmM and optionally further post-PKS genes have been deleted or inactivated.

In a further embodiment the host strain is an engineered strain based on a geldanamycin producing strain in which one or more of the post-PKS genes have been deleted or inactivated and then post-PKS genes are re-introduced to effect specific post-PKS modifications. Post-PKS genes from the geldanamycin cluster or another ansamycin clusters such as, but not limited to the macbecin or herbimycin clusters may be used.

In a further embodiment the host strain is a herbimycin (e.g. herbimycin A, B or C) producing strain.

In a further embodiment the host strain is a autolytimycin producing strain.

In a further embodiment the host strain is a reblastatin producing strain.

In a further embodiment the host strain is an engineered strain based on a herbimycin producing strain in which the gdmM homologue has been deleted or inactivated.

In a further embodiment the host strain is an engineered strain based on a herbimycin producing strain in which the gdmM homologue and optionally further post-PKS genes have been deleted or inactivated.

Starter unit biosynthetic genes that may be deleted or inactivated include, for example, genes known as ahba-3, ahba-1c, ahba-4, ahba-b, ahba-1a, ahba-1b of the ahba-B cluster in the geldanamycin producing strain, *S. hygroscopicus* AM 3602 (see Rascher et al 2005), or genes PH, OX, Ahs, Adh and AHk in the macbecin producing strain, *Actinosynnema pretiosum* ATCC 31280 (see table 3), as well as those homologues in other strains which have similar function. For example, all genes of the ahba-B cluster in the geldanamycin producing strain, *S. hygroscopicus* AM 3602 may be deleted or inactivated.

The aforementioned deletions may be combined e.g. the host strain may be an engineered strain based on a ansamycin producing strain (e.g. a geldanamycin or herbimycin producing strain) in which gdmM or a homologue thereof and one or more of the starter unit biosynthetic genes and optionally further post-PKS genes have been deleted or inactivated.

Suitably the one or more starter unit biosynthetic genes or post-PKS genes will be deleted or inactivated selectively.

In a further embodiment, one or more starter unit biosynthetic genes or post-PKS genes are inactivated in said engineered strain by integration of DNA into the gene(s) such that functional protein is not produced. In an alternative embodiment, one or more of said starter unit biosynthetic genes or post-PKS genes are deleted in said engineered strain by making a targeted deletion or deletions. In a further embodiment one or more starter unit biosynthetic genes or post-PKS genes are inactivated in said engineered strain by site-directed mutagenesis. In a further embodiment a geldanamycin producing host strain is subjected to mutagenesis, chemical or UV, and a modified strain is selected in which one or more of the starter unit biosynthetic enzymes or post-PKS enzymes are not functional. The present invention also encompasses mutations of the regulators controlling the expression of one or more of the post-PKS genes, a person of skill in the art will appreciate that deletion or inactivation of a regulator may have the same outcome as deletion or inactivation of the gene. The post-PKS genes may be introduced into said host cell under an appropriate promoter. In a preferred embodiment one or more of the deleted genes may be introduced into the chromosomal phage attachment site of the *Streptomyces* phage phiBT1 (Gregory et al., 2003). One skilled in the art will appreciate that complementation in trans is not limited to this phage attachment site, or indeed to the use of an attachment site. Therefore, complementation of deleted auxiliary genes can also be effected by, but not limited to, introduction of one or more auxiliary genes under an appropriate promoter into other phage attachment sites such as the attachment site for *Streptomyces* phage phiC31 for example by using a derivative of pSET152 (Bierman et al., 1992). One skilled in the art will recognise that there are further phages already known, and many more phages may be expected to contain integration functions that could be transferred to a delivery vector along with a suitable promoter to generate further systems that can be used to introduce genes into the host strain (Smovkina et al., 1990, Matsuura et al., 1996, Van Mellaert et al., 1998, Lee et al., 1991). As more phages are characterised one would expect there to be further available integrases that could be used similarly. Introduction of post-PKS genes under an appropriate promoter can also be effected by, without limitation, homologous recombination into a neutral position in the chromosome, homologous recombination into a non-neutral position in the chromosome (for example to disrupt a chosen gene). Self-replicating vectors can also be used for example, but not limited to, vectors containing the *Streptomyces* origin of replication from pSG5 (e.g. pKC1139 Bierman et al., 1992), pIJ101 (e.g. pIJ487, Kieser et al., 2000) and SCP2* (e.g. pIJ698, Kieser et al., 2000).

In a further embodiment an engineered strain in which one or more post-PKS genes have been deleted or inactivated as above, has re-introduced into it one or more of the same post PKS genes, or homologues thereof from an alternative geldanamycin producing strain.

In a further embodiment an engineered strain in which one or more genes has been deleted or inactivated is complemented by one or more of the post PKS genes from a heterologous PKS cluster including, but not limited to the clusters directing the biosynthesis of rifamycin, ansamitocin, macbecin or herbimycin.

A method of selectively deleting or inactivating a post PKS gene comprises:
(i) designing specific oligos based on the sequence of the gene of interest, isolating the internal fragment of the gene of interest from a suitable geldanamycin producing strain using PCR,
(ii) integrating a plasmid containing this fragment into either the same, or a different geldanamycin producing strain followed by homologous recombination, which results in the disruption of the targeted gene,
(iii) culturing the strain thus produced under conditions suitable for the production of the ansamycin analogues.

A person of skill in the art will appreciate that an equivalent strain may be achieved using alternative methods to that described above, e.g.:

Degenerate oligos based on homologue(s) of the gene of interest may be designed (e.g. from the rifamycin, macbecin or herbimycin biosynthetic clusters and/or other available sequences) and the internal fragment of the gene of interest may be isolated from a suitable geldanamycin producing strain using PCR. Different degenerate oligos may be designed which will successfully amplify an appropriate region of the post-PKS gene, or a homologue thereof, of a geldanamycin producer, or strain producing a homologue thereof.

The sequence of the gene of the *Streptomyces hygroscopicus* subsp. *geldanus* NRRL3602 strain may be used to generate the oligos which may be specific to the gene of *Streptomyces hygroscopicus* subsp. *geldanus* NRRL3602 and then the internal fragment may be amplified from any geldanamycin producing strain e.g. *Streptomyces hygroscopicus* subsp. *geldanus* NRRL3602 or *Streptomyces* sp. DSM4137 or *Streptomyces violaceusniger* DSM40699.

The sequence of the gene of the *Streptomyces hygroscopicus* subsp. *geldanus* NRRL3602 strain may be used along with the sequence of homologous genes (e.g. from the geldanamycin biosynthesis clusters of *Streptomyces* sp. DSM4137 or *Streptomyces violaceusniger* DSM40699) to generate degenerate oligos to the gene of *Streptomyces hygroscopicus* subsp. *geldanus* NRRL3602 and then the internal fragment may be amplified from any geldanamycin producing strain e.g. *Streptomyces hygroscopicus* subsp. *geldanus* NRRL3602 or *Streptomyces* sp. DSM4137 or *Streptomyces violaceusniger* DSM40699.

FIG. 2 shows the activity of the post-PKS genes in the geldanamycin biosynthetic cluster. A person of skill in the art would thus be able to identify which additional post-PKS genes would need to be deleted or inactivated in order to arrive at a strain that will produce the compound(s) of interest.

It may be observed in these systems that when a strain is generated in which one or more of the post-PKS genes does not function as a result of one of the methods described including inactivation or deletion, that more than one ansamycin analogue may be produced. There are a number of possible reasons for this which will be appreciated by those skilled in the art. For example there may be a preferred order of post-PKS steps and removing a single activity leads to all subsequent steps being carried out on substrates that are not natural to the enzymes involved. This can lead to intermediates building up in the culture broth due to a lowered efficiency towards the novel substrates presented to the post-PKS enzymes, or to shunt products which are no longer substrates for the remaining enzymes possibly because the order of steps has been altered.

A person of skill in the art will appreciate that the ratio of compounds observed in a mixture can be manipulated by using variations in the growth conditions.

One skilled in the art will appreciate that in a biosynthetic cluster some genes are organised in operons and disruption of one gene will often have an effect on expression of subsequent genes in the same operon.

When a mixture of compounds is observed these can be readily separated using standard techniques some of which are described in the following examples.

Ansamycin analogues may be screened by a number of methods, as described herein, and in the circumstance where a single compound shows a favourable profile a strain can be engineered to make this compound preferably. In the unusual circumstance when this is not possible, an intermediate can be generated which is then biotransformed to produce the desired compound.

The present invention provides novel ansamycin analogues generated by culturing a strain producing an ansamycin polyketide or an analogue thereof, for example geldanamycin or an analogue thereof, the strain optionally having selected deletion or inactivation of one or more post-PKS genes from the PKS gene cluster and providing an acid feed for incorporation as the starter unit. In particular, the present invention relates to novel ansamycin analogues produced by feeding a non-natural starter unit to a geldanamycin producing strain, optionally combined with the selected deletion or inactivation of one or more post-PKS genes, from the geldanamycin PKS gene cluster. Additionally, one or more post-PKS genes from an ansamycin biosynthetic cluster may be re-introduced.

A person of skill in the art will appreciate that a gene does not need to be completely deleted for the gene product to be rendered non-functional, consequentially the term "deleted or inactivated" as used herein encompasses any method by which the gene product is rendered non-functional including but not limited to: deletion of the gene in its entirety, deletion of part of the gene, inactivation by insertion into the target gene, site-directed mutagenesis which results in the gene either not being expressed or being expressed to produce inactive protein, mutagenesis of the host strain which results in the gene either not being expressed or being expressed to produce inactive protein (e.g. by radiation or exposure to mutagenic chemicals, protoplast fusion or transposon mutagenesis). Alternatively the function of an active gene product can be impaired chemically with inhibitors, for example metopyrone (alternative name 2-methyl-1,2-di(3-pyridyl-1-propanone), EP 0 627 009) and ancymidol are inhibitors of oxygenases and these compounds can be added to the production medium to generate analogues. Additionally, sinefungin is a methyl transferase inhibitor that can be used similarly but for the inhibition of methyl transferase activity in vivo (McCammon and Parks, 1981).

In an alternative embodiment, all of the post-PKS genes may be deleted or inactivated and then one or more of the genes may then be reintroduced by complementation (e.g. at an attachment site, on a self-replicating plasmid or by insertion into a homologous region of the chromosome). Therefore, in a particular embodiment the present invention relates to methods for the generation of ansamycin analogues (e.g. 18,21-didesoxyansamycin analogues), said method comprising:

a) providing a first host strain that produces geldanamycin when cultured under appropriate conditions
b) optionally selectively deleting or inactivating all the post-PKS genes,
c) feeding a non-natural starter unit to said strain
d) culturing said modified host strain under suitable conditions for the production of ansamycin analogues; and
e) optionally isolating the compounds produced.

In an alternative embodiment, one or more of the deleted post-PKS genes are reintroduced. In a further embodiment one or more post-PKS genes from the geldanamycin cluster from a different producing organism are reintroduced In a further embodiment, one or more of the post-PKS genes selected from the macbecin biosynthetic cluster are introduced, this group consisting of mbcM, mbcN, mbcP, mbcMT1, mbcMT2 and mbcP450 are reintroduced. In a further embodiment, 2 or more of the post-PKS genes selected from the group consisting of mbcM, mbcN, mbcP, mbcMT1, mbcMT2 and mbcP450 are reintroduced. In a further embodiment, 3 or more of the post-PKS genes selected from the group consisting of mbcM, mbcN, mbcP, mbcMT1, mbcMT2 and mbcP450 are reintroduced. In a further embodiment, 4 or more of the post-PKS genes selected from the group consisting of mbcM, mbcN, mbcP, mbcMT1, mbcMT2 and mbcP450 are reintroduced. In a further alternative embodiment, 5 or more of the post-PKS genes selected from the group consisting of mbcM, mbcN, mbcP, mbcMT1, mbcMT2 and mbcP450 are reintroduced.

Additionally, it will be apparent to a person of skill in the art that a subset of the post-PKS genes, could be deleted or inactivated and optionally a smaller subset of said post-PKS genes could be reintroduced to arrive at a strain that, when fed a non-natural starter unit, produces ansamycin analogues such as 18,21-didesoxy-ansamycin analogues.

Therefore, in a preferred embodiment the present invention relates to methods for the generation of ansamycin analogues (e.g. 18,21-didesoxy-ansamycin analogues), said method comprising:
  a) providing a first host strain that produces geldanamycin when cultured under appropriate conditions
  b) selectively deleting or inactivating gdmM,
  c) feeding a non-natural starter unit to said strain
  d) culturing said modified host strain under suitable conditions for the production of ansamycin analogues (e.g. 18,21-didesoxy-ansamycin analogues); and
  e) optionally isolating the compounds produced.

In a further preferred embodiment the present invention relates to methods for the generation of ansamycin analogues (e.g. 18,21-didesoxy-ansamycin analogues), said method comprising:
  a) providing a first host strain that produces geldanamycin when cultured under appropriate conditions
  b) selectively deleting or inactivating gdmM
  c) optionally selectively deleting or inactivating further post-PKS genes
  d) feeding a non-natural starter unit to said strain
  e) culturing said modified host strain under suitable conditions for the production of ansamycin analogues (e.g. 18,21-didesoxy-ansamycin analogues); and
  f) optionally isolating the compounds produced.

It is well known to those skilled in the art that polyketide gene clusters may be expressed in heterologous hosts (Pfeifer and Khosla, 2001). Accordingly, the present invention includes the transfer of the ansamycin polyketide biosynthetic cluster for example the geldanamycin biosynthetic gene cluster, with or without resistance and regulatory genes, either otherwise complete or containing deletions, into a heterologous host. Alternatively, the complete ansamycin polyketide biosynthetic cluster for example the complete geldanamycin biosynthetic cluster can be transferred into a heterologous host, with or without resistance and regulatory genes, and it can then be manipulated by the methods described herein to delete or inactivate one or more of the post-PKS genes or starter unit biosynthesis genes. Methods and vectors for the transfer as defined above of such large pieces of DNA are well known in the art (Rawlings, 2001; Staunton and Weissman, 2001) or are provided herein in the methods disclosed. In this context a preferred host cell strain is a prokaryote, more preferably an actinomycete or *Escherichia coli*, still more preferably include, but are not limited to *Actinosynnema mirum* (*A. mirum*), *Actinosynnema pretiosum* subsp. *pretiosum* (*A. pretiosum*), *S. hygroscopicus*, *S. hygroscopicus* sp., *S. hygroscopicus* var. *ascomyceticus*, *Streptomyces tsukubaensis*, *Streptomyces violaceusniger*, *Streptomyces coelicolor*, *Streptomyces lividans*, *Saccharopolyspora erythraea*, *Streptomyces fradiae*, *Streptomyces avermitilis*, *Streptomyces cinnamonensis*, *Streptomyces rimosus*, *Streptomyces albus*, *Streptomyces griseofuscus*, *Streptomyces longisporoflavus*, *Streptomyces venezuelae*, *Streptomyces albus*, *Micromonospora* sp., *Micromonospora griseorubida*, *Amycolatopsis mediterranei* or *Actinoplanes* sp. N902-109.

In one embodiment the entire biosynthetic cluster is transferred. In an alternative embodiment the entire PKS is transferred without any of the associated starter unit biosynthesis genes and/or post-PKS genes.

In a further embodiment the entire geldanamycin biosynthetic cluster is transferred and then manipulated according to the description herein.

In a further embodiment the entire PKS is transferred without any of the associated starter unit biosynthesis genes and/or post-PKS genes and selected post-PKS genes, for example but not limited to gdmN, mbcN, hbmN, gdmL, and/or mbcP450 are introduced into the new host.

In an alternative aspect of the invention, the ansamycin analogue(s) of the present invention may be further processed by biotransformation with an appropriate strain. The appropriate strain either being an available wild type strain for example, but without limitation *Actinosynnema mirum*, *Actinosynnema pretiosum* subsp. *pretiosum*, *S. hygroscopicus*, *S. hygroscopicus* sp. *Streptomyces violaceusniger*. Alternatively, an appropriate strain may be engineered to allow biotransformation with particular post-PKS enzymes for example, but without limitation, those encoded by mbcM, mbcN, mbcP, mbcMT2, mbcP450 (as defined herein), gdmN, gdmM, gdmL, gdmP, (Rascher et al., 2003) the geldanamycin O-methyl transferase, hbmN, hbmL, hbmP, (Rascher et al., 2005) herbimycin O-methyl transferases and further herbimycin mono-oxygenases, asm7, asm10, asm11, asm12, asm19 and asm21 (Cassady et al., 2004, Spiteller et al., 2003). Where genes have yet to be identified or the sequences are not in the public domain it is routine to those skilled in the art to acquire such sequences by standard methods. For example the sequence of the gene encoding the geldanamycin O-methyl transferase is not in the public domain, but one skilled in the art could generate a probe, either a heterologous probe using a similar O-methyl transferase, or a homologous probe by designing degenerate primers from available homologous genes to carry out Southern blots on a geldanamycin producing strain and thus acquire this gene to generate biotransformation systems.

In a particular embodiment the strain may have had one or more of its native polyketide clusters deleted, either entirely or in part, or otherwise inactivated, so as to prevent the production of the polyketide produced by said native polyketide cluster. Said engineered strain may be selected from the group including, for example but without limitation, Actinosynnema *mirum*, *Actinosynnema pretiosum* subsp. *pretiosum*, *S. hygroscopicus*, *S. hygroscopicus* sp., *S. hygroscopicus* var. *ascomyceticus*, *Streptomyces tsukubaensis*, *Streptomyces violaceusniger*, *Streptomyces coelicolor*, *Streptomyces lividans*, *Saccharopolyspora erythraea*, *Streptomyces fradiae*, *Streptomyces avermitilis*, *Streptomyces cinnamonensis*, *Streptomyces rimosus*, *Streptomyces albus*, *Streptomyces griseofuscus*, *Streptomyces longisporoflavus*, *Streptomyces venezuelae*, *Micromonospora* sp., *Micromonospora griseorubida*, *Amycolatopsis mediterranei* or *Actinoplanes* sp. N902-109.

A person skilled in the art will recognise that other ansamycin polyketide biosynthetic clusters for example the herbimycin, reblastatin or TAN clusters could equally be used to generate the compounds of the invention.

By using a herbimycin producing strain for example, but not limited to *Streptomyces hygroscopicus* AM3672 (Rascher et al., 2005) or a strain producing a herbimycin analogue for example, but not limited to an engineered *Streptomyces hygroscopicus* AM-3672 in which one or more of the post-PKS genes or starter unit biosynthesis genes have be inactivated or deleted optionally with one or more homologous or heterologous post-PKS genes reintroduced and fed with a starter acid as described herein. The sequence of the herbimycin PKS cluster is deposited in Gen Bank (accession number AY947889) (Rascher et al., 2005), Where genes not located in this sequence are required, they are located by the use of homologous or heterologous probes generated by designing degenerate oligos using homologous sequences as described herein.

A person skilled in the art will recognise that the reblastatin cluster could equally be used to generate the compounds of the invention, by using a reblastatin producing strain for example, but not limited to *Streptomyces* sp. S6699 (Stead et al., 2000) or a strain producing a reblastatin analogue for example, but not limited to an engineered *Streptomyces* sp. S6699 in which one or more of the post-PKS genes or starter unit biosynthesis genes have be inactivated or deleted optionally with one or more homologous or heterologous post-PKS genes reintroduced and fed with a starter acid as described herein.

A person skilled in the art will recognise that there will be multiple further strains that produce natural products which can be used to produce the compounds of this invention when the methods of this invention are applied.

Although the process for preparation of the ansamycin analogues of the invention as described above is substantially or entirely biosynthetic, it is not ruled out to produce or interconvert ansamycin analogues of the invention by a process which comprises standard synthetic chemical methods.

In order to allow for the genetic manipulation of the geldanamycin PKS gene cluster, the gene cluster sequence deposited in GenBank (accession number AY179507) was used (Rascher et al., 2003). Where genes not located in this sequence are required, they are located by the use of homologous or heterologous probes generated by designing degenerate oligos using homologous sequences as described herein.

In order to use the post-PKS genes of the macbecin cluster, the macbecin gene cluster was sequenced from *Actinosynnema pretiosum* subsp. *pretiosum* this is described in example 1. A person of skill in the art will appreciate that there are alternative strains which produce macbecin, for example but without limitation *Actinosynnema mirum*. The macbecin PKS gene cluster from these strains may be sequenced as described herein for *Actinosynnema pretiosum* subsp. *pretiosum*, and the information used to generate equivalent strains. Further aspects of the invention include:

- An engineered strain based on an ansamycin producing strain (e.g. a geldanamycin or a herbimycin (e.g. herbimycin A, B or C) producing strain in which the gdmM homologue and optionally further post-PKS genes have been deleted or inactivated, particularly such an engineered strain in which the gdmM homologue has been deleted or inactivated. Suitably the ansamycin producing strain is a strepromycete such as *Streptomyces hygroscopicus* subsp. *geldanus* NRRL3602 or *Streptomyces* sp. DSM4137 or *Streptomyces violaceusniger* DSM40699.
- An engineered strain based on an ansamycin producing strain in which one or more of the starter unit biosynthesis genes have been deleted or inactivated e.g. a geldanamycin producing strain, for example in which gdmO is deleted or inactivated or a herbimycin producing strain, for example in which hbmO is deleted or inactivated.
- An engineered strain based on a ansamycin producing strain (e.g. a geldanamycin or herbimycin producing strain) in which gdmM or a homologue thereof and one or more of the starter unit biosynthetic genes and optionally further post-PKS genes have been deleted or inactivated. For example, all genes of the ahba-B cluster in the geldanamycin producing strain, *S. hygroscopicus* AM 3602 (or homologue in other strains) may be deleted or inactivated. Alternatively some of the ahba-B cluster in the geldanamycin producing strain, *S. hygroscopicus* AM 3602 (or homologue in other strains) may be deleted or inactivated leading to a strain in which AHBA biosynthesis is reduced or eliminated which can be experimentally confirmed when feeding AHBA to such a strain restores good production of geldanamycin or other ansamycin.
- Use of such an engineered strain in the preparation of an ansamycin analogue (e.g. a 18,21-didesoxy-ansamycin analogue).
- Ansamycin analogues obtained or obtainable by any of the aforementioned methods.

Compounds of the invention are advantageous in that they may be expected to have one or more of the following properties: tight binding to Hsp90, fast on-rate of binding to Hsp90, good solubility, good stability, good formulation ability, good oral bioavailability, good pharmacokinetic properties including but not limited to low glucuronidation, good cell up-take, good brain pharmacokinetics, low binding to erythrocytes, good toxicology profile, good hepatotoxicity profile, good nephrotoxicity profile, low side effects and low cardiac side effects.

EXAMPLES

General Methods

Medium 1-MAM

In 1 L of distilled water

| | |
|---|---|
| Wheat starch | 10 g |
| Corn steep solids | 2.5 g |
| Yeast extract | 3 g |
| $CaCO_3$ | 3 g |
| Iron sulphate | 0.3 g |
| Agar | 20 g |

Sterilization by autoclaving at 121° C. for 20 minutes.

Medium 2-R6

To 700 mL of distilled water

| | |
|---|---|
| Sucrose | 200 g |
| Dextrin powder | 10 g |
| Casamino acids | 1 g |
| $MgSO_4 \cdot 7H_2O$ | 0.05 g |
| *Trace elements | 1 mL |
| $K_2SO_4$ | 0.1 g |
| Agar | 20 g |

*Trace elements 1 g/L of each of $FeSO_4 \cdot 7H_2O$, $MnCl_2 \cdot 4H_2O$ and $ZnSO_4 \cdot 7H_2O$.

Sterilization by autoclaving at 121° C. for 20 minutes.
Following sterilisation add the following sterile solutions (note glutamic acid is filter sterilised)

| | |
|---|---|
| L-Glutamic acid mono sodium salt (0.65M) | 100 mL |
| $CaCl_2 \cdot 2H_2O$ (0.48M) | 100 mL |
| MOPS (pH 7.2) (0.1M) | 100 mL |

Extraction of Culture Broths for LCMS Analysis

Culture broth (1 mL) and ethyl acetate (1 mL) were mixed vigorously for 15-30 min followed by centrifugation for 10 min. 0.5 mL of the organic layer was collected, evaporated to dryness and then re-dissolved in 0.25 mL of methanol.

LCMS Analysis Procedure

Analytical LCMS was performed using LCMS method 1 on an Agilent HP1100 HPLC system in combination with a Bruker Daltonics Esquire 3000+ electrospray mass spectrometer operating in positive and/or negative ion mode. LCMS method 1: chromatography was achieved over a Phenomenex Hyperclone column ($C_{18}$ BDS, 3 micron particle size, 150× 4.6 mm) eluting at a flow rate of 1 mL/min using the following gradient elution process; T=0, 10% B; T=2, 10% B; T=20, 100% B; T=22, 100% B; T=22.05, 10% B; T=25, 10% B. Mobile phase A=water+0.1% formic acid; mobile phase B=acetonitrile+0.1% formic acid. UV spectra were recorded between 190 and 400 nm, with extracted chromatograms taken at 210, 254 and 276 nm. Mass spectra were recorded between 100 and 1500 amu.

NMR Structure Elucidation Methods

NMR spectra were recorded on a Bruker Advance 500 spectrometer at 298 K operating at 500 MHz and 125 MHz for $^1$H and $^{13}$C respectively. Standard Bruker pulse sequences were used to acquire $^1$H-$^1$H COSY, APT, HMBC and HMQC spectra. NMR spectra were referenced to the residual proton or standard carbon resonances of the solvents in which they were run.

Assessment of Compound Purity

Purified compounds were analysed using LCMS method 2 described. LCMS method 2: chromatography was achieved over a Phenomenex HyperClone $C_{18}$-BDS column (4.6×150 mm, 3 micron particle size) eluting with a gradient of water+ 0.1% formic acid:acetonitrile+0.1% formic acid, (90:10) to (0:100), at 1 mL/min over 20 min. Purity was assessed by MS and at multiple wavelengths (210, 254 & 276 nm). All compounds were >95% pure at all wavelengths. Purity was finally confirmed by inspection of the $^1$H and $^{13}$C NMR spectra.

In Vitro Bioassay for Anticancer Activity

In vitro evaluation of compounds for anticancer activity in a panel of human tumour cell lines in a monolayer proliferation assay were carried out at the Oncotest Testing Facility, Institute for Experimental Oncology, Oncotest GmbH, Freiburg. The characteristics of the selected cell lines are summarized in Table 1.

TABLE 1

Test cell lines

| # | Cell line | Characteristics |
|---|---|---|
| 1 | CNXF 498NL | CNS |
| 2 | CXF HT29 | Colon |
| 3 | LXF 1121L | Lung, large cell ca |
| 4 | MCF-7 | Breast, NCI standard |
| 5 | MEXF 394NL | Melanoma |
| 6 | DU145 | Prostate - PTEN positive |

The Oncotest cell lines were established from human tumor xenografts as described by Roth et al., (1999). The origin of the donor xenografts is described by Fiebig et al., (1999). Other cell lines were either obtained from the NCI (DU145, MCF-7) or purchased from DSMZ, Braunschweig, Germany.

All cell lines, unless otherwise specified, were grown at 37° C. in a humidified atmosphere (95% air, 5% $CO_2$) in a 'ready-mix' medium containing RPMI 1640 medium, 10% fetal calf serum, and 0.1 mg/mL gentamicin (PAA, Cölbe, Germany).

A modified propidium iodide assay was used to assess the effects of the test compound(s) on the growth of human tumour cell lines (Dengler et al., (1995)).

Briefly, cells were harvested from exponential phase cultures by trypsinization, counted and plated in 96 well flat-bottomed microtitre plates at a cell density dependent on the cell line (5-10.000 viable cells/well). After 24 h recovery to allow the cells to resume exponential growth, 0.010 mL of culture medium (6 control wells per plate) or culture medium containing the ansamycin analogue was added to the wells. Each concentration was plated in triplicate. Compounds were be applied in five concentrations (100; 10; 1; 0.1 and 0.01 µM). Following 4 days of continuous exposure, cell culture medium with or without test compound was replaced by 0.2 mL of an aqueous propidium iodide (PI) solution (7 mg/L). To measure the proportion of living cells, cells may be permeabilized by freezing the plates. After thawing the plates, fluorescence was measured using the Cytofluor 4000 microplate reader (excitation 530 nm, emission 620 nm), giving a direct relationship to the total number of viable cells.

Growth inhibition may be expressed as treated/control× 100 (% T/C).

Example 1

Sequencing of the Macbecin PKS Gene Cluster

Genomic DNA was isolated from *Actinosynnema pretiosum* (ATCC 31280) and *Actinosynnema mirum* (DSM 43827, ATCC 29888) using standard protocols described in Kieser et al., (2000). DNA sequencing was carried out by the sequencing facility of the Biochemistry Department, University of Cambridge, Tennis Court Road, Cambridge CB2 1QW using standard procedures.

Primers BIOSG104 5'-GGTCTAGAGGTCAGTGC-CCCCGCGTACCGTCGT-3' (SEQ ID NO: 1) AND BIOSG105 5'-GGCATATGCTTGTGCTCGGGCTCAAC-3' (SEQ ID NO: 2) were employed to amplify the carbamoyl-transferase-encoding gene gdmN from the geldanamycin biosynthetic gene cluster of *Streptomyces hygroscopicus* NRRL 3602 (Accession number of sequence: AY179507) using standard techniques. Southern blot experiments were carried out using the DIG Reagents and Kits for Non-Radioactive Nucleic Acid Labelling and Detection according to the manufacturers' instructions (Roche). The DIG-labelled gdmN DNA fragment was used as a heterologous probe. Using the gdmN generated probe and genomic DNA isolated from *A. pretiosum* 2112 an approximately 8 kb EcoRI fragment was identified in Southern blot analysis. The fragment was cloned into Litmus 28 applying standard procedures and transformants were identified by colony hybridization. The clone p3 was isolated and the approximately 7.7 kb insert was sequenced. DNA isolated from clone p3 was digested with EcoRI and EcoRI/SacI and the bands at around 7.7 kb and at about 1.2 kb were isolated, respectively. Labelling reactions were carried out according to the manufacturers' protocols. Cosmid libraries of the two strains named above were created using the vector SuperCos 1 and the Gigapack III XL packaging kit (Stratagene) according to the manufacturers' instructions. These two libraries were screened using standard protocols and as a probe, the DIG-labelled fragments of the 7.7 kb EcoRI fragment derived from clone p3 were used. Cosmid 52 was identified from the cosmid library of *A. pretiosum* and submitted for sequencing to the sequencing facility of the Biochemistry Department of the University of Cambridge. Similarly, cosmid 43 and cosmid 46 were identified from the cosmid library of *A. mirum*. All three cosmids contain the 7.7 kb EcoRI fragment as shown by Southern Blot analysis.

An around 0.7 kbp fragment of the PKS region of cosmid 43 was amplified using primers BIOSG124 5'-CCCGC-CCGCGCGAGCGGCGCGTGGCCGCCCGAGGGC-3' (SEQ ID NO: 3) and BIOSG125 5'-GCGTCCTCGCG-CAGCCACGCCACCAGCAGCTCCAGC-3' (SEQ ID NO: 4) applying standard protocols, cloned and used as a probe for screening the *A. pretiosum* cosmid library for overlapping clones. The sequence information of cosmid 52 was also used to create probes derived from DNA fragments amplified by primers BIOSG130 5'-CCAACCCCGCCGCGTCCCCG-GCCGCGCCGAACACG-3' (SEQ ID NO: 5) and BIOSG131 5'-GTCGTCGGCTACGGGCCG-GTGGGGCAGCTGCTGT-5' (SEQ ID NO: 6) as well as BIOSG132 5'-GTCGGTGGACTGCCCTGCGCCT-GATCGCCCTGCGC-3' (SEQ ID NO: 7) and BIOSG133 5'-GGCCGGTGGTGCTGCCCGAGGACGGG-GAGCTGCGG-3' (SEQ ID NO: 8) which were used for screening the cosmid library of *A. pretiosum*. Cosmids 311 and 352 were isolated and cosmid 352 was sent for sequencing. Cosmid 352 contains an overlap of approximately 2.7 kb with cosmid 52. To screen for further cosmids, an approximately 0.6 kb PCR fragment was amplified using primers BIOSG136 5'-CACCGCTCGCGGGGGTGGCGCGGCG-CACGACGTGG CTGC-3' (SEQ ID NO: 9) and BIOSG 137 5'-CCTCCTCGGACAGCGCGATCAGCGCCGCGC ACAGCGAG-3' (SEQ ID NO: 10) and cosmid 311 as template applying standard protocols. The cosmid library of *A. pretiosum* was screened and cosmid 410 was isolated. It overlaps approximately 17 kb with cosmid 352 and was sent for sequencing. The sequence of the three overlapping cosmids (cosmid 52, cosmid 352 and cosmid 410) was assembled. The sequenced region spans about 100 kbp and 23 open reading frames were identified potentially constituting the macbecin biosynthetic gene cluster. The location of each of the open reading frames within SEQ ID NO: 11 is shown in Table 3

TABLE 2

Summary of the cosmids

| Cosmid | Strain |
|---|---|
| Cosmid 43 | *Actinosynnema mirum* ATCC 29888 |
| Cosmid 46 | *Actinosynnema mirum* ATCC 29888 |
| Cosmid 52 | *Actinosynnema pretiosum* ATCC 31280 |
| Cosmid 311 | *Actinosynnema pretiosum* ATCC 31280 |
| Cosmid 352 | *Actinosynnema pretiosum* ATCC 31280 |
| Cosmid 410 | *Actinosynnema pretiosum* ATCC 31280 |

TABLE 3 location of each of the open reading frames for the post-PKS genes and the starter unit biosynthesis genes

| Nucleotide position in SEQ ID NO: 11 | Gene Name | Function of the encoded protein |
|---|---|---|
| 14925-17909* | mbcRII | transcriptional regulator |
| 18025-19074c | mbcO | aminohydroquinate synthase |
| 19263-20066c* | mbc? | unknown, AHBA biosynthesis |
| 20330-40657 | mbcAI | PKS |
| 40654-50859 | mbcAII | PKS |
| 50867-62491* | mbcAIII | PKS |
| 62500-63276* | mbcF | amide synthase |
| 63281-64852* | mbcM | C21 monooxygenase |
| 64899-65696c* | PH | phosphatase |

TABLE 3-continued location of each of the open reading frames for the post-PKS genes and the starter unit biosynthesis genes

| Nucleotide position in SEQ ID NO: 11 | Gene Name | Function of the encoded protein |
|---|---|---|
| 65693-66853c* | OX | oxidoreductase |
| 66891-68057c* | Ahs | AHBA synthase |
| 68301-68732* | Adh | ADHQ dehydratase |
| 68690-69661c* | AHk | AHBA kinase |
| 70185-72194c* | mbcN | carbamoyltransferase |
| 72248-73339c | mbcH | methoxymalonyl ACP pathway |
| 73336-74493c | mbcI | methoxymalonyl ACP pathway |
| 74490-74765c | mbcJ | methoxymalonyl ACP pathway |
| 74762-75628c* | mbcK | methoxymalonyl ACP pathway |
| 75881-76537 | mbcG | methoxymalonyl ACP pathway |
| 76534-77802* | mbcP | C4,5 monooxygenase |
| 77831-79054* | mbcP450 | P450 |
| 79119-79934* | mbcMT1 | O-methyltransferase |
| 79931-80716* | mbcMT2 | O-methyltransferase |

[Note 1:
c indicates that the gene is encoded by the complement DNA strand;
Note 2:
it is sometimes the case that more than one potential candidate start codon can been identified. One skilled in the art will recognise this and be able to identify alternative possible start codons. We have indicated those genes which have more than one possible start codon with a '*' symbol. Throughout we have indicated what we believe to be the start codon, however, a person of skill in the art will appreciate that it may be possible to generate active protein using an alternative start codon.]

Example 2

Generation of a gdmM Inactivated Strain

An in-frame deletion of gdmM is carried out as follows.
2.1 Cloning of DNA Homologous to the Upstream Flanking Region of gdmM.

Oligos gdm1for (SEQ ID NO: 12) and gdm1rev (SEQ ID NO: 13) are used to amplify a 2268 bp region of DNA from *Streptomyces hygroscopicus* subsp. *geldanus* (NRRL 3602) in a standard PCR reaction using genomic as the template and Pfu DNA polymerase. A 5' extension in each oligo introduces restriction sites to aid cloning of the amplified fragment. The PCR product (PCRgdm1) covers a region of homology upstream of gdmM up to an including the first 2 amino acids of gdmM. This 2268 bp fragment is cloned into pUC18 that is linearised with SmaI and dephosphorylated, to give pUC18gdm1.

```
gdm1for
                                        (SEQ ID NO: 12)
TTAAGCTTGGACCGGCGCGAACTCGCGGACACCCACCT
  HindIII gdm1rev
                                        (SEQ ID NO: 13)
TTTCTAGAGGTCATGCGCCCGCCAGGATCAGGTCGACC
  XbaI
```

Plasmid pUC18gdm1 is identified by restriction enzyme digestion with NdeI and SmaI which gives the three fragments of 439 bp, 1687 bp and 2828 bp.
2.2 Cloning of DNA Homologous to the Downstream Flanking Region of gdmM.

Oligos gdm2for (SEQ ID NO: 14) and gdm2rev (SEQ ID NO: 15) are used to amplify a 2267 bp region of DNA from *Streptomyces hygroscopicus* subsp. *geldanus* (NRRL 3602) in a standard PCR reaction using genomic as the template and Pfu DNA polymerase. A 5' extension is designed in each oligo to introduce restriction sites to aid cloning of the amplified fragment. The amplified PCR product (PCRgdm2) covers a region from the last 2 amino acids of gdmM, the stop codon and a region of homology downstream of gdmM. This 2267 bp fragment is cloned into pUC18 that is linearised with SmaI, resulting in plasmid pUC18gdm2.

```
gdm2for
                                       (SEQ ID NO: 14)
TTTCTAGACCTTCGTAAGGCTCCCCTGCCTGGGCATGG
    XbaI gdm2rev
                                       (SEQ ID NO: 15)
TTGAATTCTCTGCTCGGCTACGGCTTCGGCGACGAGTA
    EcoRI
```

Plasmid pUC18gdm2 is identified by restriction enzyme digestion with NdeI and SmaI which gives the three fragments of 440 bp, 1594 bp and 2919 bp.

2.3 Generation of a Plasmid for Effecting an In-Frame Deletion of gdmM

The products PCRgdm1 and PCRgdm2 are cloned into pKC1139 in one step as follows. pKC1139 is digested with HindIII and EcoRI and the backbone fragment generated is ligated with PCRgdm1 on a HindIII/XbaI fragment and PCRgdm2 on an XbaI/EcoRI fragment in a single three part ligation. Restriction enzyme digestion is used to confirm the final plasmid, pKC1139gdm1gdm2.

2.4 Transformation of *Streptomyces hygroscopicus* subsp. *geldanus* (NRRL 3602) and Selection of a gdmM Deletion Mutant

*Escherichia coli* ET12567, harbouring the plasmid pUZ8002 is transformed with pKC1139gdm1gdm2 by electroporation to generate the *E. coli* donor strain for conjugation. This strain is used to transform *Streptomyces hygroscopicus* subsp. *geldanus* (NRRL 3602) by conjugation using standard methods (Kieser et al, (2000) Practical *Streptomyces* Genetics). Exconjugants are plated on medium 2 and incubated at 28° C. Plates are overlayed after 24 h with 50 mg/L apramycin and 25 mg/L nalidixic acid. pKC1139-based vectors self-replicate at 28° C., so transformants are anticipated to contain pKC1139gdm1gdm2 as a self-replicating plasmid. After 4-7 days colonies are patched onto medium 2 plates containing apramycin (50 mg/L) and nalidixic acid (25 mg/L). The plates are then incubated at 37° C. for 3-4 days— the increase in temperature stops replication of the pKC1139 based free plasmid, the replicon of which does not function at 37° C. and therefore continued selection with apramycin selects for integration into the chromosome via one of the regions of homology. The colonies are then re-patched onto medium 2 plates containing apramycin and nalidixic acid and incubated at 37° C. for 3-4 days to ensure that no *E. coli* cells are passaged further.

Sub-Culturing for Secondary Recombinants

After further 3-4 days of incubation, sub-culturing steps are carried out using medium 2 plates without antibiotic. To do this, material from each patch is scraped off and plated on a medium 2 agar plate and incubated at 37° C. until good growth is visible, typically on day three. A second third and fourth sub-culturing step is performed using the same technique. The fourth sub-culturing step is incubated at 28° C. to allow sporulation. When sporulation is visible after several days (typically 7-10 days), spore suspensions are isolated and dilution series carried out using standard techniques. Aliquots of the dilution series are spread on medium 1 plates and incubated at 28° C. until colonies were visible. Single colonies are picked and patched in parallel on medium 1 plates with and without apramycin.

Patches that grow on the no antibiotic plate but do not grow on the apramycin plate are re-patched onto +/−apramycin plates to confirm loss of the antibiotic marker. The mutant strain encodes an inactive GdmM protein with an in-frame deletion of 543 amino acids.

gdmM deletion mutants are patched onto Medium 1 and grown at 28° C. for four days. A 6 mm circular plug from each patch is used to inoculate individual 50 mL falcon tubes containing 10 mL seed medium (per liter; glucose 40 g, beet molasses 10 g, yeast extract 2.5 g, peptone 2.5 g, tryptone 2.5 g, oatmeal 5 g). These seed cultures are incubated for 36-72 h at 28° C., 300 rpm with a 1 inch throw. These are then used to inoculate (0.5 mL into 10 mL) production medium (same as seed medium) and are grown at 28° C. for 6 days. Secondary metabolites are extracted and analysed by LCMS for production of geldanamycin analogues as described in the General Methods. One mutant is designated *S. hygroscopicus* gdmM⁻ that should produce compound, 1, which is expected to be indistinguishable from KOS-1806 (Rascher et al., 2005). One skilled in the art can readily design alternative gdmM inactivation strategies for example by integration or by generating a disruption mutant by insertion of a resistance gene as published by Rascher (2005).

Example 3

Generation of Novel Geldanamycin Analogues by Feeding AHBA Analogues to the gdmM Knockout Strain *S. hygroscopicus* gdmM⁻

3.1 Biotransformation Using *S. hygroscopicus* gdmM⁻

*S. hygroscopicus* gdmM⁻, generation of which is described in example 2 above, is patched onto MAM plates (medium 1) and grown at 28° C. for three days. A 6 mm circular plug is used to inoculate individual 50 mL falcon tubes containing 10 mL seed medium (per liter; glucose 40 g, beet molasses 10 g, yeast extract 2.5 g, peptone 2.5 g, tryptone 2.5 g, oatmeal 5 g). These seed cultures are incubated for 36-72 h at 28° C., 300 rpm with a 1 inch throw. These are then used to inoculate (0.5 mL into 10 mL) production medium (same as seed medium) and are grown at 28° C. for 24 h. 0.1 mL of a 200 mM feed stock solution (in methanol—see list in table 4) is added to each falcon tube to give a final feed concentration of 2 mM. Tubes are incubated for a further 6 days at 28° C.

3.2 Identification of Novel Geldanamycin Analogues by LCMS in Culture Extracts

Extracts of the fermentation described in example 3.1 are generated and assayed by LCMS as described in General Methods. In all cases, the major ansamycins expected to be observed are described in table 4. The table describes the substituted benzoic acid analogue which is fed to the strain, the major LCMS masses, and the mass of the major compounds. FIGS. 3 and 4 shows the structures of the compounds expected to be produced.

TABLE 4

| | | compounds identified by LCMS | | | |
|---|---|---|---|---|---|
| Experiment number | AHBA analogue fed | Compound produced | [M + Na]+ | [M − H]− | Mass |
| 3A | 3-amino benzoic acid (HO₂C, NH₂ meta) | 14<br>15 | 541<br>525 | 517<br>501 | 518.3<br>502 |
| 3B | 2-hydroxy-5-amino benzoic acid | 14<br>16 | 541<br>541 | 517<br>517 | 518.3<br>518 |
| 3C | 2-fluoro-5-amino benzoic acid | 14<br>17 | 541<br>543 | 517<br>519 | 518.3<br>520 |
| 3D | 3-fluoro-5-amino benzoic acid | 14<br>18 | 541<br>543 | 517<br>519 | 518.3<br>520 |
| 3E | 3-fluoro-2-hydroxy-5-amino benzoic acid | 14<br>19 | 541<br>559 | 517<br>535 | 518.3<br>536 |
| 3F | 2,3-difluoro-5-amino benzoic acid | 14<br>20 | 541<br>561 | 517<br>537 | 518.3<br>538 |
| 3G | 2,3,6-trifluoro-5-amino benzoic acid | 14<br>21 | 541<br>579 | 517<br>555 | 518.3<br>556 |
| 3H | 2-fluoro-3-hydroxy-5-amino benzoic acid | 14<br>22 | 541<br>559 | 517<br>535 | 518.3<br>536 |
| 3I | 2-methyl-3-hydroxy-5-amino benzoic acid | 14<br>23 | 541<br>555 | 517<br>531 | 518.3<br>532 |

TABLE 4-continued compounds identified by LCMS

| Experiment number | AHBA analogue fed | Compound produced | [M + Na]+ | [M − H]− | Mass |
|---|---|---|---|---|---|
| 3J | 2-CF3, 3-OH, 5-NH2, 1-CO2H benzene | 14 | 541 | 517 | 518.3 |
|  |  | 24 | 609 | 585 | 586 |
| 3K | 2-Et, 3-OH, 5-NH2, 1-CO2H benzene | 14 | 541 | 517 | 518.3 |
|  |  | 25 | 569 | 545 | 546 |
| 3L | 2-Cl, 3-NH2, 5-OH, 1-CO2H benzene | 14 | 541 | 517 | 518.3 |
|  |  | 26 | 575 | 551 | 552 |
| 3M | 2-F, 3-NH2, 5-OH, 1-CO2H benzene | 14 | 541 | 517 | 518.3 |
|  |  | 27 | 559 | 535 | 536 |
| 3N | 3-NH2, 4-OH, 1-CO2H benzene | 14 | 541 | 517 | 518.3 |
|  |  | 28 | 541 | 517 | 518 |
| 3O | 3-NH2, 4-F, 5-OH, 1-CO2H benzene | 14 | 541 | 517 | 518.3 |
|  |  | 29 | 559 | 535 | 536 |
| 3P | 3-F, 4-OH, 5-NH2, 1-CO2H benzene | 14 | 541 | 517 | 518.3 |
|  |  | 30 | 559 | 535 | 536 |
| 3Q | 2-CH3, 3-NH2, 5-OH, 1-CO2H benzene | 14 | 541 | 517 | 518.3 |
|  |  | 31 | 555 | 531 | 532 |
| 3R | 2-F, 3-NH2, 1-CO2H benzene | 14 | 541 | 517 | 518.3 |
|  |  | 32 | 543 | 519 | 520 |

TABLE 4-continued compounds identified by LCMS

| Experiment number | AHBA analogue fed | Compound produced | [M + Na]+ | [M − H]− | Mass |
|---|---|---|---|---|---|
| 3S | 3-amino-2-hydroxybenzoic acid (HO₂C, NH₂, OH substituents) | 14<br>33 | 541<br>541 | 517<br>517 | 518.3<br>518 |
| 3T | 5-fluoro-3-amino-2-hydroxybenzoic acid (F, HO₂C, NH₂, OH) | 14<br>34 | 541<br>559 | 517<br>535 | 518.3<br>536 |
| 3U | 5-chloro-3-amino-2-hydroxybenzoic acid (Cl, HO₂C, NH₂, OH) | 14<br>35 | 541<br>575 | 517<br>551 | 518.3<br>552 |
| 3V | 4-fluoro-3-amino-2-hydroxybenzoic acid (F, HO₂C, NH₂, OH) | 14<br>36 | 541<br>559 | 517<br>535 | 518.3<br>536 |
| 3W | 4-chloro-3-amino-2-hydroxybenzoic acid (Cl, HO₂C, NH₂, OH) | 14<br>37 | 541<br>575 | 517<br>551 | 518.3<br>552 |

Example 4

Generation of a Strain with Inactivation of AHBA Biosynthesis

An advantage of producing a strain with gene/s involved in AHBA synthesis inactivated is that there is less competition from natural AHBA within the strain. Feeding with substituted benzoic acid analogues can therefore be more efficient, also leading to simpler purification. The method below is adapted from Rascher et a 2005.

4.1 Construction of the Plasmid pKC1139AHBAdel

Oligos LHSfor (SEQ ID NO: 16) and LHSrev (SEQ ID NO: 17) are used to amplify a ~1.65 kbp region of DNA from *Streptomyces hygroscopicus* subsp. *geldanus* (NRRL 3602) in a standard PCR reaction using genomic DNA as the template and KOD DNA polymerase. A 5' extension is designed in each oligo to introduce restriction sites to aid cloning of the amplified fragment. The amplified PCR product (PCR LHS) covers a region of the left hand side of the AHBA 'B' cluster associated with the production of AHBA. This ~1.65 kbp fragment is cloned into pUC18 which has previously been digested with SmaI and dephosphorylated, giving pUC18LHS

```
LHSfor
                                    (SEQ ID NO: 16)
CGCAAGCTTAGACCTCGACCACCGGTGTCTGGA
    HindIII LHSrev
                                    (SEQ ID NO: 17)
CCGTCTAGACACGATTTCCAGCGCATGGCCCA
    XbaI
```

Oligos RHSfor (SEQ ID NO: 18) and RHSrev (SEQ ID NO: 19) are used to amplify a ~0.98 kbp region of DNA from *Streptomyces hygroscopicus* subsp. *geldanus* (NRRL 3602) in a standard PCR reaction using genomic DNA as the template and KOD DNA polymerase. A 5' extension is designed in each oligo to introduce restriction sites to aid cloning of the amplified fragment. The amplified PCR product (PCR LHS) covers a region of the right hand side of the AHBA 'B' cluster associated with the production of AHBA. This ~0.98 kbp fragment is cloned into pUC18 which has previously been digested with SmaI and dephosphorylated, giving pUC18RHS.

```
RHSfor
                                    (SEQ ID NO: 18)
TGCTCTAGACTCACCCGCTCGCCTTCGTCA
    XbaI RHSrev
                                    (SEQ ID NO: 19)
TGCGAATTCTGAGCCACCACGGCGTGTGACA
    EcoRI
```

The products PCRLHS and PCRRHS are cloned into pKC1139 in one step as follows. pKC1139 is digested with HindIII and EcoRI and the backbone fragment generated is ligated with PCRLHS on a HindIII/XbaI fragment and PCRRHS on an XbaI/EcoRI fragment, each PCR fragment taken from the pUC18 clone, in a single three part ligation. Restriction enzyme digestion is used to confirm the final plasmid which is designated pKC1139AHBAdel.

4.2 Transformation of *Streptomyces hygroscopicus* subsp. *geldanus* (NRRL 3602) and Selection of an AHBA 'B' Deletion Mutant

*Escherichia coli* ET12567, harbouring the plasmid pUZ8002 was transformed with pKC1139AHBAdel by electroporation to generate the *E. coli* donor strain for conjugation. This strain is used to transform *Streptomyces hygroscopicus* subsp. *geldanus* (NRRL 3602) by conjugation (Kieser et al, (2000) Practical *Streptomyces* Genetics). Exconjugants are plated on medium 2 and incubated at 28° C. Plates are overlayed after 24 h with 50 mg/L apramycin and 25 mg/L nalidixic acid. pKC1139-based vectors self-replicate at 28° C., so transformants are anticipated to contain pKC1139AHBAdel as a self-replicating plasmid. After 4-7 days colonies are patched onto medium 2 plates containing apramycin (50 mg/L) and nalidixic acid (25 mg/L). The plates are then incubated at 37° C. for 3-4 days. Integration of the plasmid into the chromosome then occurs by homologous recombination. The colonies are then re-patched onto medium 2 plates containing apramycin and nalidixic acid and incubated at 37° C. for 3-4 days to ensure that no *E. coli* cells are passaged further.

Sub-Culturing for Secondary Recombinants

After further 3-4 days of incubation, sub-culturing steps are carried out using medium 1 plates without antibiotic. To do this, material from each patch is scraped off and plated on a medium 1 agar plate and incubated at 37° C. until good growth is visible, typically on day three. A second third and fourth sub-culturing step is performed using the same technique. The fourth sub-culturing step is incubated at 28° C. to allow sporulation. When sporulation is visible after several days (typically 7-10 days), spore suspensions are isolated and dilution series carried out using standard techniques. Aliquots of the dilution series are spread on medium 1 plates and incubated at 28° C. until colonies were visible. Single colonies are picked and patched in parallel on medium 1 plates with and without apramycin.

Patches that grow on the no antibiotic plate but do not grow on the apramycin plate are re-patched onto +/−apramycin plates to confirm loss of the antibiotic marker. The mutant strain contains a large deletion in the AHBA 'B' biosynthetic region.

Deletion mutants are patched onto Medium 1 and grown at 28° C. for four days. A 6 mm circular plug from each patch is used to inoculate individual 50 mL falcon tubes containing 10 mL seed medium (per liter; glucose 40 g, beet molasses 10 g, yeast extract 2.5 g, peptone 2.5 g, tryptone 2.5 g, oatmeal 5 g). These seed cultures are incubated for 36-72 h at 28° C., 300 rpm with a 1 inch throw. These are then used to inoculate (0.5 mL into 10 mL) production medium (same as seed medium) and are grown at 28° C. for 6 days. Secondary metabolites are extracted and analysed by LCMS for production of geldanamycin analogues as described in the General Methods. One mutant is designated *S. hygroscopicus* AHBA and is characterised by the lack of production of geldanamycin. Further, geldanamycin production should be restored by feeding AHBA at 24 hours into production.

Example 5

Generation of a Strain with Both gdmM and AHBA Synthesis Inactivated by Transformation of *Streptomyces hygroscopicus* gdmM⁻ with pKC1139AHBAdel The success of feeding to *Streptomyces hygroscopicus* gdmM⁻ can be improved by removing competition by AHBA. Therefore using exactly the same procedure as for example 4 an AHBA 'B' deletion is carried out in *Streptomyces hygroscopicus* gdmM⁻ to generate a superior strain for the production of compounds of the invention.

*Escherichia coli* ET12567, harbouring the plasmid pUZ8002 was transformed with pKC1139AHBAdel by electroporation to generate the *E. coli* donor strain for conjugation. This strain is used to transform *Streptomyces hygroscopicus* subsp. *geldanus* (NRRL 3602) by conjugation using standard methods (Kieser et al, (2000) Practical *Streptomyces* Genetics). Exconjugants were selected as described above (example 4) and secondary recombinants selected as described above.

The final double deletion strain is designated *Streptomyces hygroscopicus* gdmM⁻ AHBAB⁻ and is characterised by its lack of production of geldanamycin or geldanamycin analogues. When production cultures are supplemented with AHBA, KOS-1806 production is restored (Rascher et al. 2005).

Example 6

Generation of Novel Geldanamycin Analogues by Feeding to a Strain with Both gdmM and AHBA Synthesis Inactivated

*Streptomyces hygroscopicus* gdmM⁻ AHBAB⁻

16.1 Biotransformation Using *Streptomyces hygroscopicus* gdmM⁻ AHBAB⁻

*Streptomyces hygroscopicus* gdmM⁻ AHBAB⁻, generation of which is described in example 5 above, is patched onto MAM plates (medium 1) and grown at 28° C. for three days. A 6 mm circular plug is used to inoculate individual 50 mL falcon tubes containing 10 mL seed medium (per liter; glucose 40 g, beet molasses 10 g, yeast extract 2.5 g, peptone 2.5 g, tryptone 2.5 g, oatmeal 5 g). These seed cultures are incubated for 36-72 h at 28° C., 300 rpm with a 1 inch throw. These are then used to inoculate (0.5 mL into 10 mL) production medium (same as seed medium) and are grown at 28° C. for 24 h. 0.1 mL of a 200 mM feed stock solution (in methanol—see list in table 5) is added to each falcon tube to give a final feed concentration of 2 mM. Tubes are incubated for a further 6 days at 28° C.

16.2 Identification of Novel Geldanamycin Analogues by LCMS in Culture Extracts

Extracts of the fermentation described in example 16.1 are generated and assayed by LCMS as described in General Methods. In all cases, the major ansamycin expected to be observed is described in table 5, and these ansamycins should not be seen in extracts of fermentations which are unfed. The table describes the substituted benzoic acid analogue which is fed to the strain, the LCMS masses, and the mass of the compound. FIGS. 3 and 4 show the structures of the compounds expected to be produced

TABLE 5 compounds identified by LCMS

| Experiment number | AHBA analogue fed | Compound produced | $[M + Na]^+$ | $[M - H]^-$ | Mass |
|---|---|---|---|---|---|
| 6A | 3-amino benzoic acid | 15 | 525 | 501 | 502 |
| 6B | 4-amino-2-hydroxy benzoic acid | 16 | 541 | 517 | 518 |
| 6C | 4-amino-2-fluoro benzoic acid | 17 | 543 | 519 | 520 |
| 6D | 3-amino-5-fluoro benzoic acid | 18 | 543 | 519 | 520 |
| 6E | 5-amino-3-fluoro-2-hydroxy benzoic acid | 19 | 559 | 535 | 536 |
| 6F | 4,5-difluoro-3-amino benzoic acid | 20 | 561 | 537 | 538 |
| 6G | 3-amino-2,4,5-trifluoro benzoic acid | 21 | 579 | 555 | 556 |
| 6H | 5-amino-2-fluoro-3-hydroxy benzoic acid | 22 | 559 | 535 | 536 |
| 6I | 5-amino-3-hydroxy-2-methyl benzoic acid | 23 | 555 | 531 | 532 |

TABLE 5-continued
compounds identified by LCMS
| Experiment number | AHBA analogue fed | Compound produced | [M + Na]+ | [M − H]− | Mass |
|---|---|---|---|---|---|
| 6J | 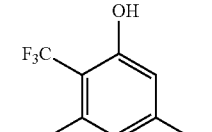 | 24 | 609 | 585 | 586 |
| 6K | 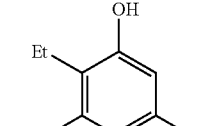 | 25 | 569 | 545 | 546 |
| 6L | 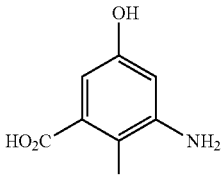 | 26 | 575 | 551 | 552 |
| 6M | 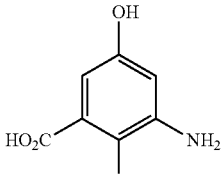 | 27 | 559 | 535 | 536 |
| 6N | 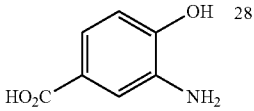 | 28 | 541 | 517 | 518 |
| 6O | 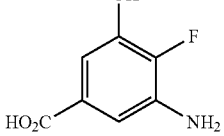 | 29 | 559 | 535 | 536 |
| 6P | 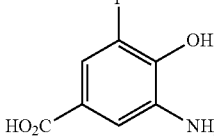 | 30 | 559 | 535 | 536 |
| 6Q | 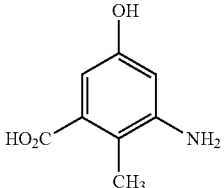 [SMILES: Nc1cc(O)cc(C(=O)O)c1Cl] | 31 | 555 | 531 | 532 |
| 6R | 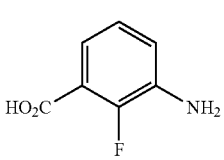 [SMILES: Nc1cccc(C(=O)O)c1F] | 32 | 543 | 519 | 520 |

TABLE 5-continued compounds identified by LCMS

| Experiment number | AHBA analogue fed | Compound produced | [M + Na]⁺ | [M – H]⁻ | Mass |
|---|---|---|---|---|---|
| 6S | 3-amino-2-hydroxy benzoic acid | 33 | 541 | 517 | 518 |
| 6T | 5-fluoro-3-amino-2-hydroxy benzoic acid | 34 | 559 | 535 | 536 |
| 6U | 5-chloro-3-amino-2-hydroxy benzoic acid | 35 | 575 | 551 | 552 |
| 6V | 4-fluoro-3-amino-2-hydroxy benzoic acid | 36 | 559 | 535 | 536 |
| 6W | 4-chloro-3-amino-2-hydroxy benzoic acid | 37 | 575 | 551 | 552 |

All references including patent and patent applications referred to in this application are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

REFERENCES

Allen, I. W. and Ritchie, D. A. (1994) Cloning and analysis of DNA sequences from *Streptomyces hygroscopicus* encoding geldanamycin biosynthesis. Mol. Gen. Genet. 243: 593-599.

Bagatell, R. and Whitesell, L. (2004) Altered Hsp90 function in cancer: A unique therapeutic opportunity. Molecular Cancer Therapeutics 3: 1021-1030.

Beliakoff, J. and Whitesell, L. (2004) Hsp90: an emerging target for breast cancer therapy. Anti-Cancer Drugs 15:651-662.

Bierman, M., Logan, R., O'Brien, K., Seno, E T., Nagaraja Rao, R. and Schoner, B E. (1992) "Plasmid cloning vectors for the conjugal transfer of DNA from *Escherichia coli* to *Streptomyces* spp." Gene 116: 43-49.

Blagosklonny, M. V. (2002) Hsp-90-associated oncoproteins: multiple targets of geldanamycin and its analogues. Leukemia 16:455-462.

Blagosklonny, M. V., Toretsky, J., Bohen, S, and Neckers, L. (1996) Mutant conformation of p53 translated in vitro or in vivo requires functional HSP90. Proc. Natl. Acad. Sci. USA 93:8379-8383.

Bohen, S. P. (1998) Genetic and biochemical analysis of p23 and ansamycin antibiotics in the function of Hsp90-dependent signaling proteins. Mol Cell Biol 18:3330-3339.

Carreras, C. W., Schirmer, A., Zhong, Z. and Santi D. V. (2003) Filter binding assay for the geldanamycin-heat shock protein 90 interaction. Analytical Biochemistry 317: 40-46.

Cassady, J. M., Chan, K. K., Floss, H. G. and Leistner E. (2004) Recent developments in the maytansinoid antitumour agents. Chem. Pharm. Bull. 52(1) 1-26.

Chiosis, G., Huezo, H., Rosen, N., Mimnaugh, E., Whitesell, J. and Neckers, L. (2003) 17AAG: Low target binding affinity and potent cell activity—finding an explanation. Molecular Cancer Therapeutics 2:123-129.

Chiosis, G., Vilenchik, M., Kim, J. and Solit, D. (2004) Hsp90: the vulnerable chaperone. Drug Discovery Today 9:881-888.

Csermely, P. and Soti, C. (2003) Inhibition of Hsp90 as a special way to inhibit protein kinases. Cell. Mol. Biol. Lett. 8:514-515.

DeBoer, C. and Dietz, A. (1976) The description and antibiotic production of *Streptomyces hygroscopicus* var. *geldanus*. J. Antibiot. 29:1182-1188.

DeBoer, C., Meulman, P. A., Wnuk, R. J., and Peterson, D. H. (1970) Geldanamycin, a new antibiotic. J. Antibiot. 23:442-447.

Dengler W. A., Schulte J., Berger D. P., Mertelsmann R. and Fiebig H H. (1995) Development of a propidium iodide fluorescence assay for proliferation and cytotoxicity assay. Anti-Cancer Drugs, 6:522-532.

Dikalov, s., Landmesser, U., Harrison, D G., 2002, Geldanamycin Leads to Superoxide Formation by Enzymatic and Non-enzymatic Redox Cycling, The Journal of Biological Chemistry, 277(28), pp 25480-25485

Donzé O. and Picard, D. (1999) Hsp90 binds and regulates the ligand-inducible α subunit of eukaryotic translation initiation factor kinase Gcn2. Mol Cell Biol 19:8422-8432.

Egorin M J, Lagattuta T F, Hamburger D R, Covey J M, White K D, Musser S M, Eiseman J L. (2002) "Pharmacokinetics, tissue distribution, and metabolism of 17-(dimethylaminoethylamino)-17-demethoxygeldanamycin (NSC 707545) in CD2F1 mice and Fischer 344 rats." Cancer Chemother Pharmacol, 49(1), pp 7-19.

Eustace, B. K., Sakurai, T., Stewart, J. K., et al. (2004) Functional proteomic screens reveal an essential extracellular role for hsp90α in cancer cell invasiveness. Nature Cell Biology 6:507-514.

Fang, Y., Fliss, A. E., Rao, J. and Caplan A. J. (1998) SBA1 encodes a yeast Hsp90 cochaperone that is homologous to vertebrate p23 proteins. Mol Cell Biol 18:3727-3734.

Fiebig, H. H., Dengler W. A. and Roth T. Human tumor xenografts: Predictivity, characterization, and discovery of new anticancer agents. In: Fiebig H H, Burger A M (eds). Relevance of Tumor Models for Anticancer Drug Development. *Contrib. Oncol.* 1999, 54: 29-50.

Gregory, M. A., Till R, and Smith M. C. M. (2003) Integration site for *Streptomyces* phage φBT1 and the development of site-specific integrating vectors. *Journal of Bacteriology* 185: 5320-5323.

Goetz, M. P., Toft, D. O., Ames, M. M. and Ehrlich, C. (2003) The Hsp90 chaperone complex as a novel target for cancer therapy. Annals of Oncology 14:1169-1176.

Harris, S. F., Shiau A. K. and Agard D. A. (2004) The crystal structure of the carboxy-terminal dimerization domain of htpG, the *Escherichia coli* Hsp90, reveals a potential substrate bingeing site. Structure 12: 1087-1097.

Hong, Y.-S., Lee, D., Kim, W., Jeong, J.-K. et al. (2004) Inactivation of the carbamoyltransferase gene refines postpolyketide synthase modification steps in the biosynthesis of the antitumor agent geldanamycin. J. Am. Chem. Soc. 126:11142-11143.

Hostein, I., Robertson, D., DiStefano, F., Workman, P. and Clarke, P. A. (2001) Inhibition of signal transduction by the Hsp90 inhibitor 17-allylamino-17-demethoxygeldanamycin results in cytostasis and apoptosis. Cancer Research 61:4003-4009.

Hu, Z., Liu, Y., Tian, Z.-Q., Ma, W., Starks, C. M. et al. (2004) Isolation and characterization of novel geldanamycin analogues. J. Antibiot. 57:421-428.

Hur, E., Kim, H.-H., Choi, S. M., et al. (2002) Reduction of hypoxia-induced transcription through the repression of hypoxia-inducible factor-1α/aryl hydrocarbon receptor nuclear translocator DNA binding by the 90-kDa heat-shock protein inhibitor radicicol. Molecular Pharmacology 62:975-982.

Iwai Y, Nakagawa, A., Sadakane, N., Omura, S., Oiwa, H., Matsumoto, S., Takahashi, M., Ikai, T., Ochiai, Y. (1980) Herbimycin B, a new benzoquinoid ansamycin with anti-TMV and herbicidal activities. The Journal of Antibiotics, 33(10), pp 1114-1119.

Jez, J. M., Chen, J. C.-H., Rastelli, G., Stroud, R. M. and Santi, D. V. (2003) Crystal structure and molecular modeling of 17-DMAG in complex with human Hsp90. Chemistry and Biology 10:361-368.

Kaur, G., Belotti, D, Burger, A. M., Fisher-Nielson, K., Borsotti, P. et al. (2004) Antiangiogenic properties of 17-(Dimethylaminoethylamino)-17-Demethoxygeldanamycin: an orally bioavailable heat shock protein 90 modulator. Clinical Cancer Research 10:4813-4821.

Kieser, T., Bibb, M. J., Buttner, M. J., Chater, K. F., and Hopwood, D. A. (2000) Practical *Streptomyces* Genetics, John Innes Foundation, Norwich Kumar, R., Musiyenko, A. and Bank S. (2003) The heat shock protein 90 of *Plasmodium falciparum* and antimalarial activity of its inhibitor, geldanamycin. J Malar 2:30.

Kurebayashi, J., Otsuke, T., Kurosumi, M., Soga, S., Akinaga, S, and Sonoo, H. (2001) A radicicol derivative, KF58333, inhibits expression of hypoxia-inducible factor-1α and vascular endothelial growth factor, angiogenesis and growth of human breast cancer xenografts. Jpn. J. Cancer Res. 92:1342-1351.

Le Brazidec, J.-Y., Kamal, A., Busch, D., Thao, L., Zhang, L. et al. (2003) Synthesis and biological evaluation of a new class of geldanamycin derivatives as potent inhibitors of Hsp90. J. Med. Chem. 47: 3865-3873.

Lee M H, Pascopella L, Jacobs W R Jr, Hatfull G F. (1991), Site-specific integration of mycobacteriophage L5: integration-proficient vectors for *Mycobacterium smegmatis*, *Mycobacterium tuberculosis*, and bacille Calmette-Guerin. Proc Natl Acad Sci USA.; 88:3111-5.

Lee, Y.-S., Marcu, M. G. and Neckers, L. (2004) Quantum chemical calculations and mutational analysis suggest heat shock protein 90 catalyzes trans-cis isomeration of geldanamycin. Chem. Biol. 11:991-998.

Liu, X.-D., Morano, K. A. and Thiele D. J. (1999); The yeast Hsp110 family member, Sse1, is an Hsp90 cochaperone. J Biol Chem 274:26654-26660.

Mandler, R., Wu, C., Sausville, E. A., Roettinger, A. J., Newman, D. J., Ho, D. K., King, R., Yang, D., Lippman, M. E., Landolfi, N. F., Dadachova, E., Brechbiel, M. W. and Waldman, T. A. (2000) Immunoconjugates of geldanamycin and anti-HER2 monoclonal antibodies: antiproliferative activity on human breast carcinoma cell lines. Journal of the National Cancer Institute 92:1573-1581.

Matsushima, P., M. C. Broughton, et al. (1994). Conjugal transfer of cosmid DNA from *Escherichia coli* to *Saccharopolyspora spinosa*: effects of chromosomal insertions on macrolide A83543 production. Gene 146(1): 39-45.

Matsuura, M., Noguchi, T., Yamaguchi, D., Aida, T., Asayama, M., Takahashi, H. and Shirai, M. (1996). The sre gene (ORF469) encodes a site-specific recombinase responsible for integration of the R4 phage genome. *J Bact.* 178(11):3374-3376.

McLaughlin S. H., Smith, H. W. and Jackson S. E. (2002) Stimulation of the weak ATPase activity of human Hsp90 by a client protein. J. Mol. Biol. 315: 787-798.

McCammon, M. T. and L. W. Parks (1981). Inhibition of sterol transmethylation by S-adenosylhomocysteine analogs. J Bacteriol 145(1): 106-12.

Muroi M, Izawa M, Kosai Y, Asai M. (1981) "The structures of macbecin I and II" Tetrahedron, 37, pp 1123-1130.

Muroi, M., Izawa M., Kosai, Y., and Asai, M. (1980) Macbecins I and II, New Antitumor antibiotics. II. Isolation and characterization. J Antibiotics 33:205-212.

Neckers, L (2003) Development of small molecule Hsp90 inhibitors: utilizing both forward and reverse chemical genomics for drug identification. Current Medicinal Chemistry 9:733-739.

Neckers, L. (2002) Hsp90 inhibitors as novel cancer chemotherapeutic agents. Trends in Molecular Medicine 8:S55-S61.

Nimmanapalli, R., O'Bryan, E., Kuhn, D., Yamaguchi, H., Wang, H.-G. and Bhalla, K. N. (2003) Regulation of 17-AAG-induced apoptosis: role of Bcl-2, Bcl-$x_L$, and Bax downstream of 17-AAG-mediated down-regulation of Akt, Raf-1, and Src kinases. Neoplasia 102:269-275.

Omura, S., Iwai, Y., Takahashi, Y., Sadakane, N., Nakagawa, A., Oiwa, H., Hasegawa, Y., Ikai, T., (1979), Herbimycin, a new antibiotic produced by a strain of *Streptomyces*. The Journal of Antibiotics, 32(4), pp 255-261.

Omura, S., Miyano, K., Nakagawa, A., Sano, H., Komiyama, K., Umezawa, I., Shibata, K, Satsumabayashi, S., (1984), "Chemical modification and antitumor activity of Herbimycin A. 8,9-epoxide, 7,9-carbamate, and 17 or 19-amino derivatives". The Journal of Antibiotics, 37(10), pp 1264-1267.

Ono, Y., Kozai, Y. and Ootsu, K. (1982) Antitumor and cytocidal activities of a newly isolated benzenoid ansamycin, Macbecin I. Gann. 73:938-44.

Patel, K., M. Piagentini, Rascher, A., Tian, Z. Q., Buchanan, G. O., Regentin, R., Hu, Z., Hutchinson, C. R. And McDaniel, R. (2004). "Engineered biosynthesis of geldanamycin analogs for hsp90 inhibition." Chem Biol 11(12): 1625-33.

Pfeifer, B. A. and C. Khosla (2001). "Biosynthesis of polyketides in heterologous hosts." Microbiology and Molecular Biology Reviews 65(1): 106-118.

Rascher, A., Hu, Z., Viswanathan, N., Schirmer, A. et al. (2003) Cloning and characterization of a gene cluster for geldanamycin production in *Streptomyces hygroscopicus* NRRL 3602. FEMS Microbiology Letters 218:223-230.

Rascher, A., Z. Hu, Buchanan, G. O., Reid, R. and Hutchinson, C. R. (2005). Insights into the biosynthesis of the benzoquinone ansamycins geldanamycin and herbimycin, obtained by gene sequencing and disruption. Appl Environ Microbiol 71(8): 4862-71.

Rawlings, B. J. (2001). "Type I polyketide biosynthesis in bacteria (Part B)." Natural Product Reports 18(3): 231-281.

Roth T., Burger A. M., Dengler W., Willmann H. and Fiebig H. H. Human tumor cell lines demonstrating the characteristics of patient tumors as useful models for anticancer drug screening. In: Fiebig H H, Burger A M (eds). Relevance of Tumor Models for Anticancer Drug Development. *Contrib. Oncol.* 1999, 54: 145-156.

Rowlands, M. G., Newbatt, Y. M., Prodromou, C., Pearl, L. H., Workman, P. and Aherne, W. (2004) High-throughput screening assay for inhibitors of heat-shock protein 90 ATPase activity. Analytical Biochemistry 327:176-183

Schulte, T. W., Akinaga, S., Murakata, T., Agatsuma, T. et al. (1999) Interaction of radicicol with members of the heat shock protein 90 family of molecular chaperones. Molecular Endocrinology 13:1435-1488.

Shibata, K., Satsumabayashi, S., Nakagawa, A., Omura, S. (1986a) The structure and cytocidal activity of herbimycin C. The Journal of Antibiotics, 39(11), pp 1630-1633.

Shibata, K., Satsumabayashi, S., Sano, H., Komiyama, K., Nakagawa, A., Omura, S. (1986b) Chemical modification of Herbimycin A: synthesis and in vivo antitumor activities of halogenated and other related derivatives of herbimycin A. The Journal of Antibiotics, 39(3), pp 415-423.

Shirling, E. B. and Gottlieb, D. (1966) International Journal of Systematic Bacteriology 16:313-340

Smith-Jones, P. M., Solit, D. B., Akhurst, T., Afroze, F., Rosen, N. and Larson, S. M. (2004) Imaging the pharmacodynamics of HER2 degradation in response to Hsp90 inhibitors. Nature Biotechnology 22:701-706.

Smovkina, T., Mazodier, P., Boccard, F., Thompson, C. J. and Guerineau, M. (1990) Construction of a series of pSAM2-based integrative vectors for use in actinomycetes. *Gene* 94: 53-59.

Spiteller, P., Bai, L., Shang, G., Carroll, B. J., Yu, T.-W. and Floss, H. G. (2003). The post-polyketide synthase modification steps in the biosynthesis of the antitumor agent ansamitocin by *Actinosynnema pretiosum*. J Am Chem Soc 125(47): 14236-7

Sreedhar A. S., Nardai, G. and Csermely, P. (2004) Enhancement of complement-induced cell lysis: a novel mechanism for the anticancer effects of Hsp90 inhibitors. Immunology letters 92:157-161.

Sreedhar, A. S., Soti, C. and Csermely, P. (2004a) Inhibition of Hsp90: a new strategy for inhibiting protein kinases. Biochimica Biophysica Acta 1697:233-242.

Staunton, J. and K. J. Weissman (2001). "Polyketide biosynthesis: a millennium review." Natural Product Reports 18(4): 380-416.

Stead, P., Latif, S., Blackaby, A. P. et al. (2000) Discovery of novel ansamycins possessing potent inhibitory activity in a cell-based oncostatin M signalling assay. J Antibiotics 53:657-663.

Supko, J. G., Hickman, R. L., Greyer, M. R. and Malspeis, L (1995) Preclinical pharmacologic evaluation of geldanamycin as an antitumor agent. Cancer Chemother. Pharmacol. 36:305-315.

Takahashi, A., Casais, C., Ichimura K. and Shirasu, K. (2003) HSP90 interacts with RAR1 and SGT1 and is essential for RPS2-mediated disease resistance in *Arabidopsis*. Proc. Natl. Acad. Sci. USA 20:11777-11782.

Tanida, S., Hasegawa, T. and Higashide E. (1980) Macbecins I and II, New Antitumor antibiotics. I. Producing organism, fermentation and antimicrobial activities. J Antibiotics 33:199-204.

Tian, Z.-Q., Liu, Y., Zhang, D., Wang, Z. et al. (2004) Synthesis and biological activities of novel 17-aminogeldanamycin derivatives. Bioorganic and Medicinal Chemistry 12:5317-5329.

Uehara, Y. (2003) Natural product origins of Hsp90 inhibitors. Current Cancer Drug Targets 3:325-330.

Van Mellaert, L., Mei, L., Lammertyn, E., Schacht, S., and Anne, J. (1998) Site-specific integration of bacteriophage VWB genome into *Streptomyces venezuelae* and construction of a VWB-based integrative vector. *Microbiology* 144: 3351-3358.

Vasilevskaya, I. A., Rakitina, T. V. and O'Dwyer, P. J. (2003) Geldanamycin and its 17-Allylamino-17-Demethoxy analogue antagonize the action of cisplatin in human colon adenocarcinoma cells: differential caspase activation as a basis of interaction. Cancer Research 63: 3241-3246.

Watanabe, K., Okuda, T., Yokose, K., Furumai, T. and Maruyama, H. H. (1982) *Actinosynnema mirum*, a new producer of nocardicin antibiotics. J. Antibiot. 3:321-324.

Weber, J. M., Losick, R. (1988) The use of a chromosome integration vector to a map erythromycin resistance and production genes in *Sacharopolyspora erythraea* (*Streptomyces erythraeus*) Gene 68(2), 173-180

Wegele, H., Müller, L. and Buchner, J. (2004) Hsp70 and Hsp90-a relay team for protein folding. Rev Physiol Biochem Pharmacol 151:1-44.

Wenzel, S. C., Gross, F, Zhang, Y., Fu, J., Stewart, A. F. and Müller, R (2005) Heterologous expression of a myxobacterial natural products assembly line in Pseudomonads via Red/ET recombineering. Chemistry & Biology 12: 249-356.

Whitesell, L., Mimnaugh, E. G., De Costa, B., Myers, C. E. and Neckers, L. M. (1994) Inhibition of heat shock protein HSP90-pp $60^{v-src}$ heteroprotein complex formation by benzoquinone ansamycins: Essential role for stress proteins in oncogenic transformation. Proc. Natl. Acad. Sci. USA 91: 8324-8328.

Winklhofer, K. F., Heller, U., Reintjes, A. and Tatzelt J. (2003) Inhibition of complex glycosylation increases the formation of $PrP^{sc}$. Traffic 4:313-322.

Workman P. (2003) Auditing the pharmacological accounts for Hsp90 molecular chaperone inhibitors: unfolding the relationship between pharmacokinetics and pharmacodynamics. Molecular Cancer Therapeutics 2:131-138.

Workman, P. and Kaye, S. B. (2002) Translating basic cancer research into new cancer therapeutics. Trends in Molecular Medicine 8:S1-S9.

Young, J. C.; Moarefi, I. and Hartl, U. (2001) Hsp90: a specialized but essential protein folding tool. J. Cell. Biol. 154:267-273.

---

The invention claimed is:

1. A compound of formula (I) or a pharmaceutically acceptable salt thereof:

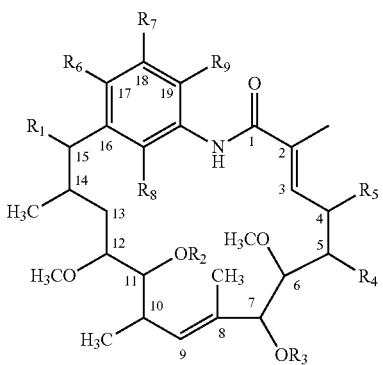

(I)

wherein:
- $R_1$ represents H, OH, or OMe;
- $R_2$ represents H or Me;
- $R_3$ represents H or $CONH_2$;
- $R_4$ and $R_5$ both represent H;
- $R_6$ represents H, F, OH, OMe, Br, Cl, $CF_3$, $CH_3$, SH, $CH_2CH_3$ or $NR_{10a}R_{11a}$;
- $R_7$ represents H, F, OH, OMe, Br, Cl, $CF_3$, $CH_3$, SH, $CH_2CH_3$ or $NR_{10b}R_{11b}$;
- $R_8$ represents H, F, Br, Cl, $CF_3$, $CH_3$, SH, $CH_2CH_3$ or $NR_{10c}R_{11c}$;
- $R_9$ represents H, F, OH, OMe, Br, Cl, $CF_3$, $CH_3$, SH, $CH_2CH_3$ or $NR_{10d}R_{11d}$;
- $R_{10a}$, $R_{11a}$, $R_{10b}$, $R_{11b}$, $R_{10c}$, $R_{11c}$, $R_{10d}$, $R_{11d}$ independently represent H, $CH_3$ or $CH_2CH_3$;

provided however that:
(i) when $R_7$ represents OH, $R_8$ represents H and $R_9$ represent H, then $R_6$ does not represent H, OH or OMe;
(ii) when $R_7$ represents OMe, $R_8$ represent H and $R_9$ represents H, then $R_6$ does not represent OMe;
(iii) when $R_6$ represents H, OH, or OMe, $R_7$ represents H and $R_8$ represents H, then $R_9$ does not represent OH, Cl or $NH_2$;
(iv) when $R_6$ represents H, OH, or OMe, $R_8$ represents H and $R_9$ represents H, then $R_7$ does not represent $NH_2$; and
(v) when $R_6$ represents H or OH, then $R_7$, $R_8$ and $R_9$ do not all represent H.

2. A compound according to claim 1 which is a compound of formula (IA) or a pharmaceutically acceptable salt thereof

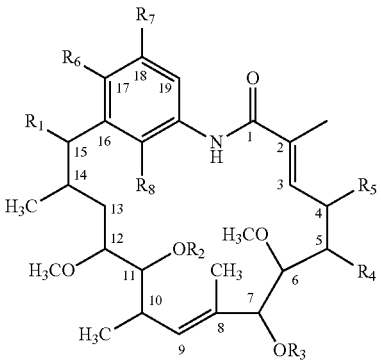

(IA)

wherein:
- $R_1$ represents H, OH, or OMe;
- $R_2$ represents H or Me;
- $R_3$ represents H or $CONH_2$;
- $R_4$ and $R_5$ both represent H;
- $R_6$ represents H, OH, OMe or F;
- $R_7$ represents H or F; and
- $R_8$ represents H or F.

3. A compound according to claim 2, wherein $R_1$ represents H, $R_2$ represents H, $R_3$ represents $CONH_2$, $R_4$ and $R_5$ each represent H, $R_6$ represents OH, $R_7$ represents F and $R_8$ represents H.
4. A compound according to claim 2 which is selected from the group consisting of:
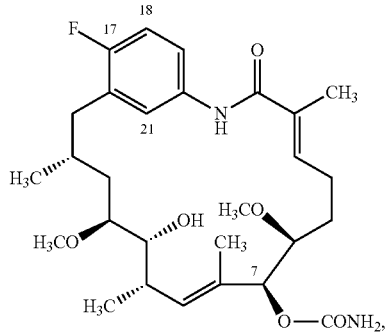
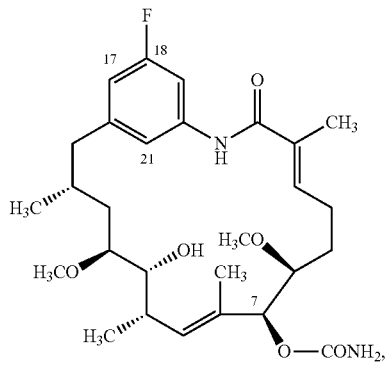
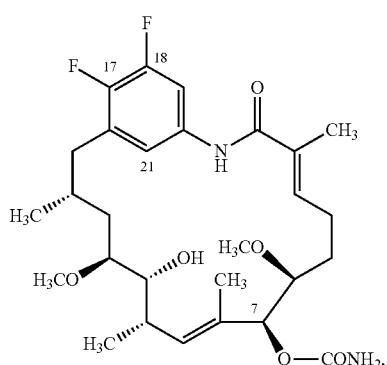
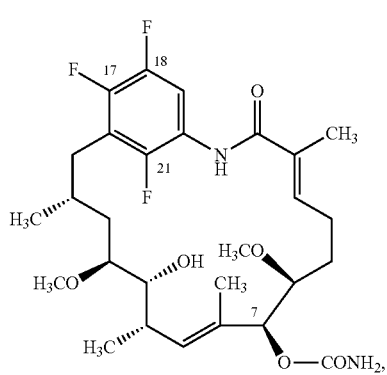
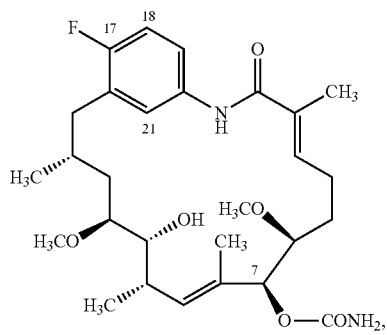
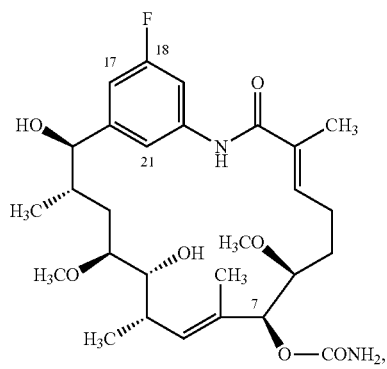
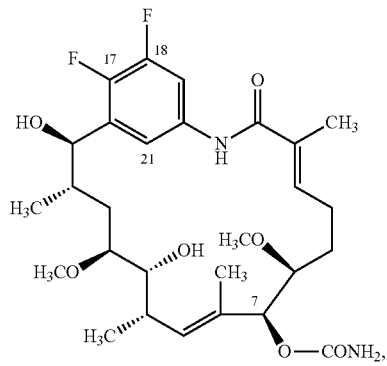
or
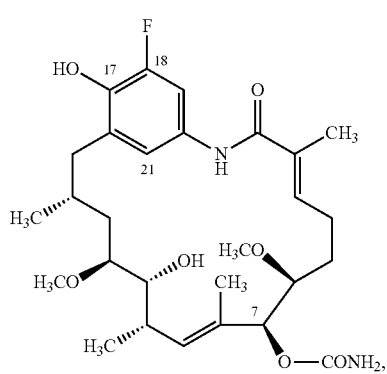
and pharmaceutically acceptable salts of any one thereof.

5. A compound according to claim 1 selected from the group consisting of:
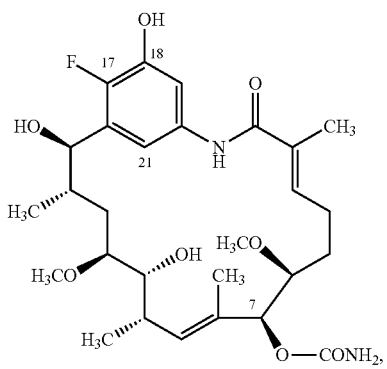
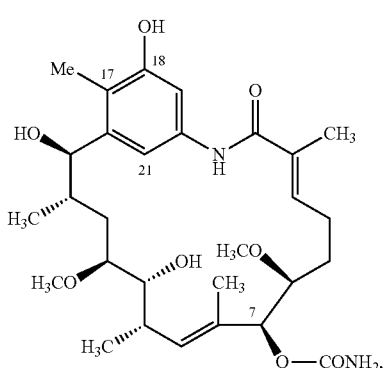
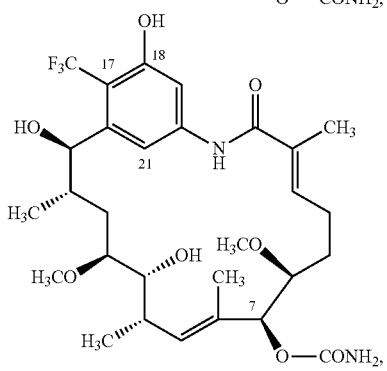
or
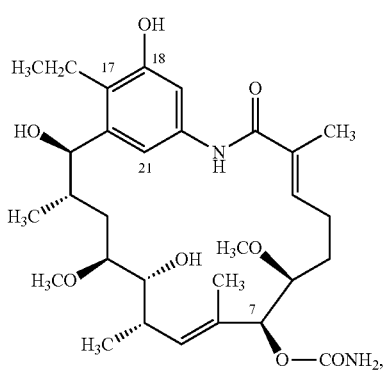
and pharmaceutically acceptable salts of any one thereof.
6. A compound according to claim 1 selected from the group consisting of:
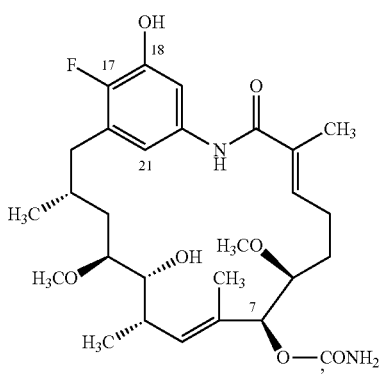
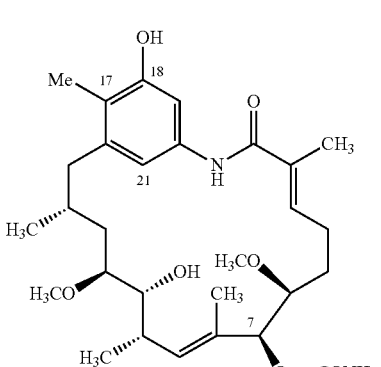
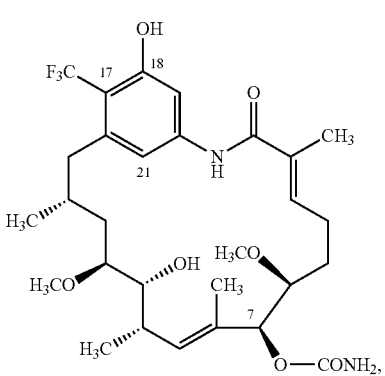
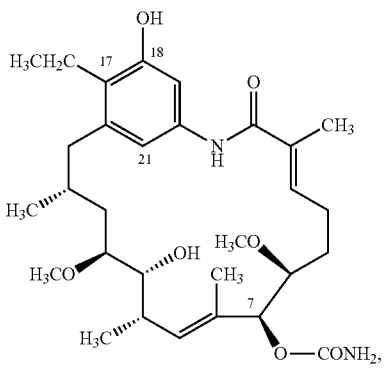

and pharmaceutically acceptable salts of any one thereof.

7. A compound according to claim 1 selected from compounds 28, 29, 30, 31, and 32, which have the following formulae:

and pharmaceutically acceptable salts of any one thereof.

8. A method for preparing a compound as defined in claim 1 which comprises:
 a) providing a strain that produces an ansamycin or an analogue thereof when cultured under appropriate conditions;
 b) feeding a starter unit which is not AHBA to said strain such that the starter unit is incorporated into said compound as defined in claim 1;
 c) culturing said strain under suitable conditions for the production of said compound; and
 d) optionally isolating the compounds produced.

9. A method according to claim 8 wherein the strain is an ansamycin producing strain and the starter unit is selected such that the strain produces a 18,21-didesoxyansamycin analogue.

10. A method according to claim 9 wherein the starter unit is selected such that the strain produces a 18,21-didesoxyansamycin analogue which is optionally substituted by fluorine.

11. A pharmaceutical composition comprising a compound as defined in claim 1 or a pharmaceutically acceptable salt thereof, together with one or more pharmaceutically acceptable diluents or carriers.

12. A method for the production of an 18,21-didesoxy-ansamycin analogue or a pharmaceutically acceptable salt thereof according to claim 1 (hereinafter "said compound(s)"), said method comprising:
   a) providing a first host strain that produces said compound when cultured under appropriate conditions;
   b) feeding a non-natural starter unit to said strain;
   c) culturing said host strain under suitable conditions for the production of said 18,21-didesoxy-ansamycin analogues; and
   d) optionally isolating the compounds produced.

13. A pharmaceutical composition comprising a compound or a pharmaceutically acceptable salt thereof according to claim 2, together with one or more pharmaceutically acceptable diluents or carriers.

* * * * *

SEQUENCE LISTING

```
<160> NUMBER OF SEQ ID NOS: 19

<210> SEQ ID NO 1
<211> LENGTH: 33
<212> TYPE: DNA
<213> ORGANISM: Artificial sequence
<220> FEATURE:
<223> OTHER INFORMATION: Primer

<400> SEQUENCE: 1
ggtctagagg tcagtgcccc cgcgtaccgt cgt                                 33

<210> SEQ ID NO 2
<211> LENGTH: 26
<212> TYPE: DNA
<213> ORGANISM: Artificial sequence
<220> FEATURE:
<223> OTHER INFORMATION: Primer

<400> SEQUENCE: 2
ggcatatgct tgtgctcggg ctcaac                                         26

<210> SEQ ID NO 3
<211> LENGTH: 36
<212> TYPE: DNA
<213> ORGANISM: Artificial sequence
<220> FEATURE:
<223> OTHER INFORMATION: Primer

<400> SEQUENCE: 3
cccgcccgcg cgagcggcgc gtggccgccc gagggc                              36

<210> SEQ ID NO 4
<211> LENGTH: 36
<212> TYPE: DNA
<213> ORGANISM: Artificial sequence
<220> FEATURE:
<223> OTHER INFORMATION: Primer

<400> SEQUENCE: 4
gcgtcctcgc gcagccacgc caccagcagc tccagc                              36

<210> SEQ ID NO 5
<211> LENGTH: 35
<212> TYPE: DNA
<213> ORGANISM: Artificial sequence
<220> FEATURE:
```

```
<223> OTHER INFORMATION: Primer

<400> SEQUENCE: 5
ccaaccccgc cgcgtccccg gccgcgccga acacg                              35

<210> SEQ ID NO 6
<211> LENGTH: 34
<212> TYPE: DNA
<213> ORGANISM: Artificial sequence
<220> FEATURE:
<223> OTHER INFORMATION: Primer

<400> SEQUENCE: 6
gtcgtcggct acgggccggt ggggcagctg ctgt                               34

<210> SEQ ID NO 7
<211> LENGTH: 35
<212> TYPE: DNA
<213> ORGANISM: Artificial sequence
<220> FEATURE:
<223> OTHER INFORMATION: Primer

<400> SEQUENCE: 7
gtcggtggac tgccctgcgc ctgatcgccc tgcgc                              35

<210> SEQ ID NO 8
<211> LENGTH: 35
<212> TYPE: DNA
<213> ORGANISM: Artificial sequence
<220> FEATURE:
<223> OTHER INFORMATION: Primer

<400> SEQUENCE: 8
ggccggtggt gctgcccgag gacggggagc tgcgg                              35

<210> SEQ ID NO 9
<211> LENGTH: 39
<212> TYPE: DNA
<213> ORGANISM: Artificial sequence
<220> FEATURE:
<223> OTHER INFORMATION: Primer

<400> SEQUENCE: 9
caccgctcgc gggggtggcg cggcgcacga cgtggctgc                          39

<210> SEQ ID NO 10
<211> LENGTH: 38
<212> TYPE: DNA
<213> ORGANISM: Artificial sequence
<220> FEATURE:
<223> OTHER INFORMATION: Primer

<400> SEQUENCE: 10
cctcctcgga cagcgcgatc agcgccgcgc acagcgag                           38

<210> SEQ ID NO 11
<211> LENGTH: 100588
<212> TYPE: DNA
<213> ORGANISM: Actinosynnema pretiosum
<220> FEATURE:
<221> NAME/KEY: misc_feature
<222> LOCATION: (1)..(100588)
<223> OTHER INFORMATION: macbecin biosynthetic gene cluster
<220> FEATURE:
<221> NAME/KEY: gene
<222> LOCATION: (14925)..(17909)
<223> OTHER INFORMATION: mbcRII encoding transcriptional regulator
<220> FEATURE:
```

```
<221> NAME/KEY: gene
<222> LOCATION: (18025)..(19074)
<223> OTHER INFORMATION: mbcO encoding aminohydroquinate synthase (gene
      encoded by complement DNA strand)
<220> FEATURE:
<221> NAME/KEY: gene
<222> LOCATION: (19263)..(20066)
<223> OTHER INFORMATION: mbc? encoding unknown protein function, AHBA
      biosynthesis (gene is encoded by the complement DNA strand)
<220> FEATURE:
<221> NAME/KEY: gene
<222> LOCATION: (20330)..(40657)
<223> OTHER INFORMATION: mbcAI encoding PKS
<220> FEATURE:
<221> NAME/KEY: gene
<222> LOCATION: (40654)..(50859)
<223> OTHER INFORMATION: mbcAII encoding PKS
<220> FEATURE:
<221> NAME/KEY: gene
<222> LOCATION: (50867)..(62491)
<223> OTHER INFORMATION: mbcAIII encoding PKS
<220> FEATURE:
<221> NAME/KEY: gene
<222> LOCATION: (62500)..(63276)
<223> OTHER INFORMATION: mbcF encoding amide synthase function
<220> FEATURE:
<221> NAME/KEY: gene
<222> LOCATION: (63281)..(64852)
<223> OTHER INFORMATION: mbcM encoding C21 monooxygenase function
<220> FEATURE:
<221> NAME/KEY: gene
<222> LOCATION: (64899)..(65696)
<223> OTHER INFORMATION: PH encoding phosphatase (the gene is encoded by
      the complement DNA strand)
<220> FEATURE:
<221> NAME/KEY: gene
<222> LOCATION: (65693)..(66853)
<223> OTHER INFORMATION: OX encoding oxidoreductase (the gene is encoded
      by the complement DNA strand)
<220> FEATURE:
<221> NAME/KEY: gene
<222> LOCATION: (66891)..(68057)
<223> OTHER INFORMATION: Ahs encoding AHBA synthase (the gene is encoded
      by the complement DNA strand)
<220> FEATURE:
<221> NAME/KEY: gene
<222> LOCATION: (68301)..(68732)
<223> OTHER INFORMATION: Adh encoding ADHQ dehydratase
<220> FEATURE:
<221> NAME/KEY: gene
<222> LOCATION: (68690)..(69661)
<223> OTHER INFORMATION: AHk encoding AHBA kinase (the gene is encoded
      by the complement DNA strand)
<220> FEATURE:
<221> NAME/KEY: gene
<222> LOCATION: (70185)..(72194)
<223> OTHER INFORMATION: mbcN encoding carbamoyltransferase function
      (the gene is encoded by the complement DNA strand)
<220> FEATURE:
<221> NAME/KEY: gene
<222> LOCATION: (72248)..(73339)
<223> OTHER INFORMATION: mbcH encoding methoxymalonyl ACP pathway (the
      gene is encoded by the complement DNA strand)
<220> FEATURE:
<221> NAME/KEY: gene
<222> LOCATION: (73336)..(74493)
<223> OTHER INFORMATION: mbcI encoding methoxymalonyl ACP pathway (the
      gene is encoded by the complement DNA strand)
<220> FEATURE:
<221> NAME/KEY: gene
<222> LOCATION: (74490)..(74765)
<223> OTHER INFORMATION: mbcJ encoding methoxymalonyl ACP pathway
      function (the gene is encoded by the complement DNA strand)
<220> FEATURE:
<221> NAME/KEY: gene
<222> LOCATION: (74762)..(75628)
<223> OTHER INFORMATION: mbcK encoding methoxymalonyl ACP pathway
      function (the gene is encoded by the complement DNA strand)
<220> FEATURE:
<221> NAME/KEY: gene
```

```
<222> LOCATION: (75881)..(76537)
<223> OTHER INFORMATION: mbcG encoding methoxymalonyl ACP pathway
      function
<220> FEATURE:
<221> NAME/KEY: gene
<222> LOCATION: (76534)..(77802)
<223> OTHER INFORMATION: mbcP encoding C4,5 monooxygenase function
<220> FEATURE:
<221> NAME/KEY: gene
<222> LOCATION: (77831)..(79054)
<223> OTHER INFORMATION: mbcP450 encoding P450 function
<220> FEATURE:
<221> NAME/KEY: gene
<222> LOCATION: (79119)..(79934)
<223> OTHER INFORMATION: mbcMT1 encoding O-methyltransferase function
<220> FEATURE:
<221> NAME/KEY: gene
<222> LOCATION: (79931)..(80716)
<223> OTHER INFORMATION: mbcMT2 encoding O-methyltransferase function

<400> SEQUENCE: 11
gatctggggc gacgagccgc ccgccgggcc ggggccggcg ttgcaggcgc tcgtctcccg      60
gctgcggcgg gcgctcggcg cgccgggcgc ggtcgcgctg ggggtgggcg ggtaccggct     120
cgtggcggac gtggacgcgg cgcggttcga ggagctggcc gcgcggggcg gggaggacgc     180
gctgcgggag gccgccgcgc tgtggggcgg gcgggtcggg ggcgagccgc cggtggtcgc     240
ggccgtcgcg ccgcgggtgg cgacccggct ggcgcggctg tcggtggagg tggtgctgga     300
cctggcggag gtcgagctgg cgctcgggcg caccggggcg gccatcggtg gggcgagcgg     360
ggtgctggcc gagcacccgg cgcacgagcg gccgccgggg gtgctggtgg acgcgctcgc     420
gggcgcggga cggcaggccg aggcgctggc ggcctacgag cgggtccgcg cggcgctggc     480
cgacgagctg ggcgccgacc ccggcacggg cctgcgcgag cgccacctgc ggctgctgcg     540
cgccaccccg ccaccgctcc cccggccgaa cgcgctgccc gcgccggtga cgggcttcct     600
cggccgggac gccgacctcg cccgcgtcgc cgacctgctg gccgccgggc ggctggtcac     660
cgtcgtcggg cccggcgggg tgggcaagac ccggctggcc gtggaggcgc tgcgccggga     720
ccgggacgcg ctgctggtgg acctcgcgcc ggtcgccgag ccctcggagg tcgtcgccgc     780
cgtgctcgcc gggatcgggc tgcgcggcga ccgcgaccgg ccgggcgggg acgcgacggc     840
gctgctggcc gccgagctgg cggcgcgcag gtcggtgctg ctgctggaca actgcgagca     900
cctggtcgac gccgtggccc acctggtcgc gctcctgctc cccgctgccc cgagctgcg     960 cgtgctcgcc accagccggg aaccctggc ggtcgacggg gaggcgctgg tcccgctggg    1020
gccgctcgcg ctgccggaa tcggggacgg gcttgacgcc gcggtcggca cggcctcggt    1080
gcggttgttc gcccaacggg cgtcggcggt gcgcccggt ttcgccgtcg acgccacgac    1140
gctgccggac gtggtgcgcc tggtgcgggc gctggacggg ctgccgctgg cgctggagct    1200
ggccgccgcc cggttgcgcg ccctgccgct gcccgacctg gtggccgggt tgtcggcgcg    1260
gttccgcctg ctggcgggcg ggaaccgggc cgcgccgccc cggcaccgca cgctgcgcgc    1320
ggtgatcgcg tggagctggg acctgctgga cgggcccgag cgggccgtgg ccgagcggat    1380
ctccgtgctg cccggcgggg tcaccccgga gtcggccgcc gccgtctgcg cgggcgccgt    1440
gcccgccgac gaggtgcccg aactgctggc cgcgctggtc gaccggtcgc tgctgagcct    1500
ggtcgggggt cggcggcgga tgctggagac ggtgcgcgcg tacggggtcg agcgcctggc    1560
cgccgccggg gacttgagcg cggtccgcga cctggccgcc gcgcacgtgg cggggggtgct    1620 ggcggggcag gacgcggtgc tgcgcgggcc ggggcagcgc gcggcggtgg cggcgatcgg    1680
cgcggagcac gacaacgcgg tggccgcgct gcaccaccgg tgcgccaccg gggacgcgga    1740
```

```
cggggcgctc gcgctggcgc tgtcgctggt ctggtactgg caggtgttcg gccgccagtc    1800
cgagggcgcg cactggctcg ggcgggcgct ggcggtgccc ggcgggccgt ccccggagcg    1860
ggactgcgcg cgggccgccc acctgctcgg cctggccgac ggcgggcacg gggtgggtga    1920
tcgcggggag gtggggcgc tcgcggaccg ggtgctggcg caccggggc tccccggtca      1980 cctgcgggtg ctcggggcgg tcctgctgtt cctgctgggg cgcggcgagg gggtgttccg    2040
ggagctgggc gcggcggcg ggtggttgtc cgggctggcg cacctgttcc tggccgagct     2100
ggcggagaac gcgggcgagc tggaccgggc gcgcgggcac gcggaggtgt ccctggaccg    2160
gttccgggcg gccggggacg ggtggggcgt ggcgggggtg ctgccggtgc gggcgcgggc   2220
gcggcggtac gacgacctgg acgggacgtg ggcggacctt cgggaggcgc gggcgctgga    2280
gggggagttc ggggcgctga gccccggtga ccggtgcgg gcggacctgc ggtgggtcga     2340
cctgcacgag cggcgcggtg acagcggggc ggcgctggag gtgctggccg cggcccgtgc    2400 tcgggggag caggtcgcgg tggtggacgc gcggaggcc gcgctgcggg tgcggctcgg      2460
ggacctgggg cgggcgggtg agctgctggc cggggtgggt ggggcggtgg gcgacctggc    2520
gcgggccgcg tatcgggtgg cctcggggga cctggcgggt gcggagcggg cgttgcggcg    2580
ggcgcgggtg gtggcggctg cgagcgggga gctgcccgcg ctggcccggg tggcggtggg    2640 ggcggcggc ctggagcagg cgcggggcg gtgggcgggg tcggggtgc tgctcgggac      2700 ggccgcgcgg gtgcggggcg cgcacgaccg caccgacccc ctggtgcgcg agctggtcga    2760 ccggggggcgg gcggcggtgg gcgggagcgc gttcgcggcg gcgtacgcgc gggggtggga  2820
ggcggagcgg gacgtggcgg cggcgttcgt gctctgagcg ccgggatcgg gcgggcgggg   2880
tcaggcgggc ggggtcatgt gggcggggtc aggcgggcca ggtcacacgt ccagggaccc    2940
cgcccagtcc gcgatcgtcc ggacttcggc ctgcgtcggg aagaccttct cggtgagcac    3000
gcggtgcacc tcggggtcgc cgtccaggca gccgtcggcc aggacggtga gctggaagtc    3060
caggtcggcg gcctggcgga gggtggacag gaccacgccg ctggtcgcga tgccggtgag    3120
caccaggtgg tcgacgccct gggcgcgcag gacgaggtcc aggtcgctgc ccgcgaacgc    3180
gctgacgcgc gcgcttggtca ccaccacctc gtcgtcgagc ggcgcggtct cggggtggaa   3240
gtcggtggcg ccggagcccc tggggccgc ggccaggcgg ccgaacatct tgttgcgcgg     3300
gtggatctcc gcgtagtcgg ggcggaagcc gacgccgacg tggatcaccg gcacggacgc    3360
ggcgcgggcc gcctcgagcg cggtggcgag cctggggagg taggccgggt cggggtagcg    3420
ggcgaccacg gcgggctgga cgtccatcac cagcaggggcg ggggtgggga tctcgggcct   3480
cgtttcggtg gtggcggcgc ggggccgcc ggtgggggtc aggggtgcgg gggtgccggg     3540
gtgagcaggc tggtgacggt gagcaggcgg tcggcgagtt cctcggggcg cagcgggtcc    3600
tcggcgcgca cgacccagtc gtggacgatc gcgccggtgc cgtgggagat cagcacggcc    3660
aggtcgcggg cggcccgctc gtccacctcg cccaggccgg cgcgcagggc ctcggtggtg    3720
atgagggtgc ggaagagctc ggccagggcc tccgccagcc gccacgcgca cgggccggtg    3780
agcacggcgc ggtagaaggg gcggtggtcg gcgaagtggc gggccacggc caggaggcgg    3840
gcgtggcgcg gggccgcgg gtcggccagg tgcggcagga gctcgcgccg caccaggtcc    3900
gccgcagcgg cgacgaggag cgtgtcgcgg tcgccgaagt gctggtagag cagctgcctg    3960
ctgacgtcgg cggcctcggc caggtcggtc accgggaccg ccgccccgcg ctcggcgacc    4020
aggtcgacgg cggcggccat gagggcggcc ctggagcggg cgaccggcg gtcggggcgg     4080 gtggtcacgg gggtgaaact agacagttgt caataaatga gcaagtgtcg tcgaacgcgc    4140
```

```
gcgcgggaat ctccggtgcg cggggcccgt ccctggcagc atgatcacgc gatgaccgag    4200
gtgaggacgc gcccgtacgc cggggcccgcg gacctgcgcg cgatgcaggg gttggcgcgg    4260
cggatctgga cgccgtcgag ccggtggcac gtcggcgacc tggcctggca gcgcaaccag    4320
cacaccgggc gcgaggccga gtggccgacc gcgctgtggg aggcgggcgg cgaggtggtg    4380 gcgtggggt gggccgagct gccgggtgag ctggcgctgc tggtcgaccc cgcccggccg    4440
gagcttgcgg gggcggtgct cgactggttc gcgggcgtgg ccaccgcgcc ccggcggtcg    4500
gtcaccgtgc tggacgccga accgcacctg gtcgccgcgc tggaggctcg cgggtacgag    4560
cggctgggcg ggccgcactt ccggcactcg gtgcgcgcgc tggacgacct gccgacgccc    4620
gaactgcccg ccgggtaccg ggtccgcgcc gtgcggggcg aggaggacgt ggcggcgcgg    4680
gtcgcggcgc accgggcggc ctggtggccg tcgcgggtca ccgaggagag ctaccgggcg    4740
gtgatggggg cgtggccgta ccggccgggg ctggactggg tggtggaggg gccggacggg    4800
cggttcgcgg ccacctgcct gatctggttc gacgagcgca acggcgtggg cgagctggaa    4860
ccggtcgggg tcgaccccgg tctgcggcgg cgcgggctgg ggcgggcggt gtgcctggcg    4920
gcgctgggcg cgctgcgcga ggcgggcggg cgggcggcgg tggtgtaccc gctgcacggg    4980
caccccgacc accccgcgcc cgcgccgctg taccgggggc tggggttccg cgagcacgcc    5040
cgcacgatca ccttcaccgc gctggaggcg cgcgggtagc agcggccggg cggggcgagc    5100
ggacccggtc gacgagcggc tccgctgtcg gagcggtcgt cccagcgcgt ggacaccagt    5160
gccacgacca gaccgcgccc cgcttcgcgt ggtcggctcg ggggtcgacc gcggtgaggc    5220
tctcgccggg gtgggtgaac cacgtcctgg cgatggcctg caccgcgagc accgggtgcc    5280
gcccgtggcg ctggacgtca ccgacgcagc cgccgtcgac cgggccgggc cggccgcgtt    5340
cggccgttgc gccgcgccgg ccgagtccga cgccaggtgg cggccggtcc ccgggtccgc    5400
ctggaactga ccccgccggc ctccccgccc gcccgtccgg ccgggcgccg aacccgcctc    5460
aggcgtgctc gaccgcgcgc accgatcccc ccaccaccac cggcatcggg acgtggtgca    5520
cggtcgtcgg gctgcggtcg cggcggggc gggacaggag gagttccacg gccatcgcgc    5580
ccaggcggtg gtgcggcagg gcgacggtgg tcaggcgcgg gcgcatccag gcggccacgg    5640
ggtggtcgtc gaagccgacc acggagacgt cgtccggcac ggacaggccc gcctccgcga    5700
gcgcctggca cgcgccgaac gccaggcggt cgttgaagca cagcagcgcg cgagggcggt    5760
ggtgggacag gaggtccagg gtggcgcggt agccgttctc cggcatccac tccacgcacg    5820
ggcgcacgct ctccacctcc accccgcgcc ccgcgaaggt ctccagcgcg ccggagaggc    5880
gggccacggc ggcgatgtgg cgcgggtcga tcgcctcggc cgtgggcccg gtgccgatca    5940
ggtgcacgcc ctcgcggtgc ccggcgtcga gcagcacgcg cgccgccgaa cggccgccgc    6000
cgcggtcgtc ggggagcacg gcgtgcgcgg ggaagtcgtt ggcgggcagc acgttcagca    6060
gcacggacgg cccgtcgcgc agccgtccg ggacctccag cagccggggg aacctggccg    6120
cgaagaccac gccctccacc tggcgggcgc gcagcgaggc caccagcgcc gcctccacct    6180
cgcggtcgcc gccgctctca ccggcgaaca gggtgaaccc gtgccggtgg gcggcgccga    6240
ccgcgccctc gatcagctca ccggacagct ggccgaggc cacggcgtcc gagacgaaac    6300
cgagggtctt ggtgcgggag gcggacagca gcgtgtcgcg gcggtagccg agctgctcgg    6360
ccgtcgcccg caccttgcgc tccaccgccg ccgagatgcg cagctcccga gcgcggccgg    6420
agagcaccag ggaggcggtg ggcaccgaca cggcgcaggc ggacgcgacg tcggccagcg    6480
tgacgcgcgt ccgcccgctc tcgcggacac ctgctcgcgg gggtgtgccc gtcacccgtg    6540
```

```
cctcccgtca ccggtcgcgc gacagccccg cgcgaggtcc taccccatcg tgcaggccgc   6600
gccgttcaag gagaacccccg aaggtggggc gcgtccccg ccgtgggtga cctggtagcc   6660
gatgctgact ttgccaccgg gtgggatcgc cgcgttgtag cccgcgtcgc gggcggtcac   6720
ccggcccgag ctgggcgcgt acgaggcgtt ccagccggag gtgatcacct ggcccgcggg   6780
cagcgcgaac tccagcgacc agccctgcac ctgcgtggtc ccggtgttgg tgatggcgag   6840
ctccgccgtc aggccgttgc cccaggcgtt gacggtggcc gacacccggc aggccccgg    6900
ctgcggttcg ccgggcgtgg tggtggtggt ggtggtggtg gtcgtggtcg tggtggtgct   6960
ggtcgggtcg gggccggttc cggcgaactg ggtgaagaac cgccaggtct cctcgggcgc   7020
ccacgtcctg gtgccgctgt cgccgggcgc gttgtcctgc ggtgcggcga tgtggccctc   7080
gtcgaacgcg acccagcgca ccgggtagcc gtcgcggcag ccggtgtagg tggtgccccg   7140
gtgggtcagg ctgccctggg acggttccgg cgggttctgc gcggcgcagc cgttgttgcg   7200
cacgaaccgg tcgcgcatcg agcgcccgcc ggagatgttc aggacgctgt cgcgcaggcc   7260
gtggatgccg aggtaggcga tgggctgcgt gccgccggcg cagccgctga gcacgccgcc   7320
cgcgatgacc gcgaccgcgc ggaacaccgt cggccgcgag caggccaccg agtaggacat   7380
cgcgccgccg tagctgaagc cggtggcgaa ccgctgggtg gtgtccacgc acagcccggc   7440
gtcgagctgg cggacgatgt cgtcgacgag ggtgatgtcc tcgccgccgt tgttggccca   7500
gccgttgttg aagccctgcg cgccacgaa  gatcgtgctg ctgcccgcca ggcgcttgag   7560
gccgtagtag gaccagacgt cccgctgcac ggtctggccg gtggcgacgt cgttcgcggt   7620
gccgctgagc cagtggaagc cgaagacgac gcggtggggg cggttccggt cgtagccgtc   7680
cgggatcgac aggatgtagg tgcgggactt gccgctgctg gtgatcgtgc gcgtgccgct   7740
ggtgagcgcg ggcgccttgc cgcagccctc cgtcgtggcg gacgcgccgg gggcgccgga   7800
cgcgccgggc gctccggtcg cgctggtggt gatcagcccc gcggcgaggg tgagcagcgc   7860
gatgcccgct gccgcgagga ccctgttgcg cgccaaggga ttcgcccttc ctgtggtggt   7920
tccggtgggt gtggtcacgg ggtggtgagg tcgaagcggc gggcggtgac ggagccgccg   7980
agcgcggcgg tggcgtggtt gaagacggcg aagcggtagc ccatgaagaa ccgccagtcg   8040
ttcttgagcg tgaacgccgg gccgaaggcg gtgaagttga cgccgtcggt gctgtaggag   8100
aacccgggcct gcctgccgtt gccggggcgg atgtcggcgt tggcgcgcaa ccagatccgg   8160
gagccgccca ggtcggcgct cgcgacctcg tagccggttc cggtggtgcg ccaggagccg   8220
tccatggtca ggcggtgac  ggagacgatc cggttgcggc cgttgtcgcg cttgacgccg   8280
atccacgccg aggagtcgcg cagcacggcc agcccggtgc ggtcgccgtc gcgcatcccc   8340
gacaggtcca gttccacggt gccggtggag gtgggggccct ggatgcggtg ggtgagggtg   8400
ttgcgggcgg agtacaggtc gttggtgacg gtcgcggtgg acaggcgaag gccgttgttc   8460
acgctgtact tggcggtgtc cggggttgtgg ttccactccc actgcgggcc gagcgcggcg   8520
ccggagaagg tgtcggcgcc gatcatgggt ttgacctggc gcggggcgc  gggcaggttc   8580
ggcttcgggt aggtcgcgcc ccagccgccg ttgacggtgg tgacgcgcgg ccagccgtcc   8640
gaggtccagg tgatcggggc gagcaccggc acgcgcccgc cggggtaggc gtcgacgaac   8700
gccaggtagt gccagtcgcc gttctgggtc tgcaccaggc cgccctggtg cggcactccc   8760
ccgccctgga tcggcgaggg caggtcgagc agcacctgct ggatcgagta cgggccgaac   8820
gggctggacg acttgagcac gtactggccg ttcgcgggcc tggtgagcca gatgtagtag   8880
ttgccgccgc gcttgtagaa gcgcgcccct tcgagggtgc cgatgttcga ggggtctgg   8940
```

```
aacacctgct gggagcggac ctccgacttc ccgtcggcgg agagctgggc gacgctgatg    9000
ctggtgttgc cgtaggcgac gtacaggtg  tcgtcgtcgt ccacgagcat cccggcgtcg    9060
tagtagcact tgttgatggt ggtgtgcttg gaccactggc cgtcgacggc ggtcgcggtg    9120
tacaggtgcg tctgggcgaa gtcgacgcag ccgccccagt agaaggtgcg gttgctcttg    9180
cggtgcgcca ggaacgacgc ccagatgccg ttgacgtacg cgcgggagcc gttgcccatg    9240
tcgtacttgg ccccgaagtc caggcgtggc acggagtgcc cggcgaactc ccagttgacc    9300
aggtcgtagg agcgcagcac gggcgcgccg ggcgagtagt gcatggtgga ggccgagtag    9360
tagtaggtgt cgtccacgcg caggacgtcg atgtcggcga agtcctgcca cagcacgggg    9420
ttggtgtagg tcccggccgc gcgggccggg tgggtggtgg tggcggtcag gctcgccgcc    9480
acgaggccga gcacgccag  ggcgatgggc gcccatcggc gttgacgggg catcggtgtg    9540
cctctcctgg tgtccgggag ttggctctgg gcgcggcggc ggtggacttg tcgggcgcgg    9600
cggtggtcgt gggggtcagc aggggagtt  ggtctgggtc agcaggccca gccgccaggg    9660
caggcggttg tagtcgccgg acgcgttggg gtccaggccc tggtacaggt agctcagctt    9720
gcaggggttg atctccatgg tctggtcggt cccgctgcgc accagctcgc cgtgctgat    9780
gtcgcgcgtc cactggccac cggggaacgt ggtgttgttg gccctggcga acgggttcga    9840
ctcgctgtcg gccagcgcgg tccacggtcc ggcgatcgcc ggggcggtcc aggagcggaa    9900
ccagcggcgg ccgtccgagc cgatcgcctc gtggagcatc agccactggt tcttgccggc    9960
gaccttgtag atgttggacg cctcgaacaa ccggttgcgg ttgctgtcct gcatggcgat    10020
cacggtgttg gtgaagccgt tggggaactg ggcgaggctg gtctccgagc ggtacaggtg    10080
gccgttgtcg tccgaggaga acaggtggca cttggccgtg tcgcagacgg tccagaagtc    10140
gacccagtag ccgttgccga tgttgtcccg gatgatctgc ggcatcccgt tggcgtagaa    10200
gttcctcggc gcggaccagg acgcggggtt ctcgatgtcg gcggtcgtcg agtacgaggc    10260
gttggacccg gtctggtaca ccaggtacca caggcgttgc ggggcgaagt agaacacctg    10320
cggcgcggcc cggtagcccg tgccgatccc ggagcggtcc aggtagtggt gcggggcgga    10380
cgcggcctgg gaccagtcgg tgaagctggt gtgcacgagg ttgtagccgt tggtgtagac    10440
cgaggcgaac acgtggtagc ggccgttgtg gcgcaccacg ctggggtcct tgacggagac    10500
cgtggcgtgc gaggagtcgg gcttgggtcc gatcagcgcg ccgctggagg accaccggaa    10560
gctgctcggc agcgagccgc ccggttgctg cggggtcgtg gtggtgggcg gcgtggtcgg    10620
gggcgtggtg gtcgtgggcc cgactcctcc cgtgcacgtg gtcccgttga ggctgaacga    10680
ggtcgggtcg gggttggacc cggtggaggt cgcggtgaac ccgaactcga cgcggccccc    10740
ggtgggatg  gcggcgttgt aggaggcgtt gcgggcgctc acctggccgc cggactggga    10800
cacctcggcg ttccaggcct gcgcgacctg ctggcccgag ccgtaggtcc aggtgagcgt    10860
ccagccgtcg acgcgtcac  cgaggttggt gatggcgacg ctcgcggtga aaccgccctg    10920
ccactgggag gtcgccgcgt aggcgatcga gcaccccggc gccgcggcgg cctggggtgg    10980
gagggcggca agcgcggcca ccatggcgag cgaggtggtg gccatggcgc cgatccgggc    11040
ccggcgcggg gtgaacagcc ttgcgaggag catggtcgcc cttcgtcgtc gtcgacgggt    11100
ggtcggcgcg gccgaccggg agcggcggga gcgggctggt actcccccac ttcctgcaat    11160
ctagccaggt ggcacagggt ggtcaaagct aaaaagggcg gacgcggttt agcttccagc    11220
gcaaaggttt cgcgcgttct ttcggccggg gggcaggtgg atcggggcgg gctcggggcg    11280
aggacggggc tgggaatggg gcgggggatg gggcgggctc ggggcggggg tcgcccggag    11340
```

```
cccgccacgg gtcagaggcg cacgcggacg acggtgaacg ggaggttcgg ctcggcgatc   11400
tggtactgga agttgaccac cagcaggtcg tcgccgtcga aggtcgcggt ggacgggacg   11460
tccatgcccc tgccgttgac ccgccgcagc accgtggcgc gggagtggtc ctcgctcagc   11520
cgcaggacgc tgatctcgcc ctccgggtgg aacaggctgg tgacgctgta gaggtcgttg   11580
ccgcgcagga gcagcccgtc cgagccgatg tcgcccacgc cgcccaggtc gatcggggtg   11640
acggcgccgt gcgggtgct gatgcggtgg aacgcctggg agttggtgtc ggcgagcagc   11700
acgtggcggc cgtccggggt gaccacgagg ccgttgccgt tgatgccctc ctcgtagcgc   11760
accggggagt cggcgaggtc cacgaacgtc ctcagtggct ggtcgacctc ggggctcgcc   11820
agctgggcgg cggtgatccg gtagaggacg gggcggaacg agtcgctgac gtaggcgtcg   11880
ccgttcgggg cgatggcgac gtcgttgacc aggccgtcgc gggcgccgga gtcgaacacg   11940
tgcaggagcg cgccggtgcg ggtgctgtgg acgaagacct tgccggtggc gccgcccgcg   12000
atgaccagcc tgcctcgggt gatcttcatg ccgacggcgg tggtgcggcc gtgctgaccg   12060
gcgggcagga acggctccag ggcggggcgg tcgacgtggc cgcgccagat cgtgccgtcg   12120
gtcgtgccgc cgacgtagaa gtgcggcgtg cccggctcgc ggacgatgcc ctccgggtag   12180
gcgcggtcgc cggggaccac gtagcgggtg acggggtggt gcgcggcggc ggcgggtggc   12240
acggcggcgg cgggtggcgc ggcggcggcg ggtggcgcgg cggcggggag ggctggggcg   12300
agcgcggtga ggagcagggt cgcggtgagg agggctcggg tggtggtcac ggaagggctc   12360 cggggtgtcga aggggtgtct ggcgccagac aagcgcttcg tggcgcgggg tgcagtgggg   12420
cgcttgtcgg gggtagttct tcaccccccct tccgggcggg gcggccgact agggtgagcg   12480
gtgtgggcga tcttgggcgg cacccggtgg cgaaccgctc cgacgtgcgg gacttcctgg   12540
tcagcaggcg cgcgagggtg agtccggggc gggccgggct gcccgtgctc gggcggcggc   12600
gggtgccggg gttgcggcgg gaggaggtcg cgctgctcgc cggggtcagc gtggactggt   12660 acaccgctt ggagaagggg cacatcggcg gtgtctcgcg ggaggtgctc gacgccgtgg   12720
ccggggtgct gcggctcgac gccgaggagc gggtctacct gttcgacctg gcgcgcgcgg   12780
cccggcgtcc ccgcgccgcc gaggtggcgg cggaggccgc gctgcccgcg acggcgcagt   12840
ggctgctgga cagcatgacg ctgtcgtcgg cgatggtgac cgggcggcgg caggacgtgc   12900
tggcggtcaa cccgctggcc cgcgcgctct acgcgccgct gttcgccagc gccaccacgc   12960
gggacggcgg ccgggcgaac ctcgcccgct accacttcct cgacgcgggc gcccgcgagt   13020
tctacgggga ctgggcggc accgccgacg tgctcgtcgc cgcgctgcgc gccgaggccg   13080
ggcgcgaccc gcgcgacggg gccacccgcg agctggtggg cgagctgacg gccgcgagca   13140
ccgagttccg ggcgcggtgg agcgcgcacg acgtgctgct gcaccgcgcg ggcgccaaga   13200
ccttccggca ccccgaggcg ggtgagctga gcctgagcta ccactcggtg gacctgccga   13260
tctccgccac cgagacccgg cacgtgtgcg cgtgcaccgc cgaacccggc tcgaccgacg   13320
aggcgaggct gcgcgcgctc gtcgggtgag ccggggtgg ccggccaccg ccgtcgcgct   13380
cgcggcggcg gggcggggcc gccggtcaga gcgtgagcgc catcccgatc gagcggggc   13440 cggtctcggt gaagccgtgc ttgaggtaca gcggcggcc gggcgcgtcg gccaggaggg   13500
tcacgaacgc gccgggcggg gcggcctcgc ggatgcgccg gagcagcgcg tccatgatcg   13560
cgccgccgac gccccttccc tggtggtcgg gcagcacggc catgtcgacg acgtggaagt   13620
accagccgcc gtcgccgagg acccggccca tgccgacggt cccgccgtcc gcgtgcgtga   13680
cgtggaagga ggcccaggcg ccgggcaggg cggcggcggc ctgctcggcg gtcttgggcg   13740
```

```
acaggccgga ctcggcgcgc aggcggaggt agtcggcgac ggacggcggg gtcgggtgga    13800
gctcgtagtc ccggtgcacg cggtcaggct cccacgggcg cgggcgggcc cccgcccgac    13860
ctgacgattt ccccgtcggc ggggatgcgg gcgggcgctc gcggattttc gacatccccc    13920
ggcccggcga gacgcggcgg cgccgctgaa aagagcgccg tcgcggccct tcgcgccgcc    13980
cccgacatcc cccgcgcggc gaccggtcaa tgcggtccac gcctgggggt ttccctccca    14040
cgtcgaacac cgccaccacg cgcccacgcg ccgcgtcgac caccccgacg ccgaggaaca    14100
cctgttcacg ggcacgggaa gccgcagcgg aggggggaacc gggaatggcc gcaggcgatc    14160
gcggcacgac gtccgcacat caccgcgagc agaatcgcga ggcgttcacc ggggcggcgg    14220
aggaagattc cagcgcccct ctcgaagaac ctgcgggaag ccctggaaga aaacccggac    14280
ccgaaacgcg acaaaattgc ggacacccac ccgtgaaaca ccgggcgccc ccaccaggtc    14340
acccgctgac atcacgctca gtcagtatcg gcacgctccc ccgccgaggc ggagcgcgac    14400
acccgcccca accgggcacc gagcgggcac ctccactcgg cccagcaccg ccccaagatc    14460
gcacgtagca cgggttgaaa ccgctcaagc gcatctcaac ccgttcggag cagagtggcg    14520
cccgtcacgt cccgaccggt cacggttggc aacgggtcca gtccacgcga ggtggcatca    14580
agcgcacttg ccccgatcac acccgcccgt gcaaccgaat gcagcaggga tatctttccc    14640
gagaactcgg ccgttaaccg ggagtggagc caggcccacc cctaagacgc ttgcccacat    14700
gcccaacaat ggtgaagatg gaacggcgga ccgcaccgcg aacgcgaacc gaactccgcg    14760
agagggcacg gtgaacgatc ctggaacagc tactgccgcg tagctcaagg gtggaacgcc    14820
cggctcgcgc gcggcggagg gaataacggc ttttacgccc tcgacaacag cttgtcaacg    14880
aaacccgtgc acccgagcgg tccccgcgcg caccgctcgc gggggtggcg cggcgcacga    14940
cgtggctgcc cggcgtcgac gacgacgcga gttcccccgac cgcccgcgaa ggcggtcgcg    15000
gatcgccacg acggggcacc cggaccacgc ctccccccgga acagcgcgcc cacgcgcggt    15060
tccggcgcgc gccgggaccg ccgcacccgc cggagcgccg ccaccggccg gggccggtcc    15120
ccgcggaccg ggtcgccttc cggaccacca ctccacggac cacggaaagg accactcccc    15180
cagtggagct tctgcgcgca cccgagatcc agtcggccgt cgagcacctc gcggtggacc    15240
tgccggaccg ggcgggacgg gcgttcctgg tggacggacc gccgcctgc ggcaagacga    15300 cggccctgcg gcggctcgtc gaccggatcg cccacgagga ccacctcgtg ctcaccgcca    15360
cctgcacccc gccggagacg gagctgccgt tcggggtgct caagcagctc ctcgcctccc    15420
ccggcatggc cagggtcgac ccgcgcctgg tcgccgacct cggcgagctg ctcgccccgg    15480
ccccgccgcc cgccgacgac tcggcgctcc tgcagctgta ccactcgctg tgcgcggcgc    15540
tgatcgcgct gtccgaggag gtgccgctgg tcatcgcggt ggacgacgtc cgccacggcg    15600
acaccgcctc gctgcacgtg ctgctgcagc tggtgcaccg gctggacacg gcgcgggtgc    15660
ggctgctgct caccgacgac ctgctgctgc cggtgagctt cccgccgctg cgctacgagc    15720
tgctgcgcct gcgcgggctc ggcctggtcc gggtcgcgcc gctgcctgcg gccagggtgc    15780
gggaggaggc ggtgcgggcg gtcggcgcgg acgtcgcgaa gcgggtcgac ttcgccgcgc    15840
tgaccggcgg caacccgctg ctgctgcacg cgctggcggt ggacgtgctg gaggcgggcg    15900
agccgcgcga gatcggctac ggcaactcgt tcctgtcctg cctgcaccgc aacgaacccc    15960
tgttcctgga caccgtgcgg gcgctggccg tgctgggcgg cggctcggcg tcggacctgg    16020
gcaggctgtc cgggcacgag ccggagcagg tcgcccaggt gctgaacgcc ctgcgggagt    16080
cggggctgct ggccgaggac gggttccggc acgacgcggg gcgccgcgcg gtcgtcgcgg    16140
```

```
acaccccggt cgccgagcac gaggtgctgc accgccgcgc cgcgcggctg ctgcgcgacc    16200
agggcggcgc ggtcaccgac atcgccgacc acctgctgcg ggcgggccgc atcaccgacc    16260
cgtgggcggc ggacctgctg gtggacgcgg cggagctggt ggtgcagcgc ggcgagccga    16320
cggcggcggt ggcgctgctc cagcgcgcgc tcgactgcag cccggaccgg gagcgcagga    16380
cggccgtgca ggcgcggctg ccacggccg agtggctggt gaacccgtcg acctcggcaa     16440
ggcaccacac cgcgctgctg gcggcgttcc acgcgggcag gttgtcggtg cgcgacagcg    16500
cgacgctgat gaagcacctg cgctgggccg ggaacaccgc cgactcggac gcggtgctcg    16560
cccggctgcg gaccgacccg cgcgccgccg aggacgtgcc ggtgctggag cactggctga    16620
ccagcaccta ccccggcgcg gcccggccca ggaccgtgct ggggcgggac gtggactcgg    16680
cgcgcagcag ggcggacctg gtgccgaggg cgaacgcggt gctgctggac gtgctggtgg    16740
ccggggacag cgacgacgtg gccgaccggg cggaggcggt gctgcgggag ctgcggctgg    16800
cgcgggagtc cgggtgctac ggcggtgcgg ccgtgctggc gctgtccgcg ctgctctact    16860
cggaccgcgc ggacgtggcc gcctcgtggt gcgagcagct gctgtcggcg cgggccgtgc    16920
cgctgctgcc gatgccgcgc gcgcaggtgc tggcgctggc ggccgagtcg cgctgcgcc     16980
ggggcgacca cccgagcgcg gacgagctgg cgcgggaggc gctgaccgtg gtgtcccga     17040
ccgcgtgggg ggtgtcggtg gggctgccgc tgagcaccag ggtgctggcg ctgaccagga    17100
tgggccgcta cgacgaggcg gcggccgtgg tggcgcagcc ggtgccgaac gggatgttcg    17160
ggcaccgcaa cagcgtggac tacctgtacg cgcgcgggca cttcttcctg gcgcgggaac    17220
ggccgcgcgc ggcgctgggc gacttcctgc tgtgcgggga gcagctgacc cggtggggcc    17280
tgggcagcgg gtgcgcgccg gtgccgtggc ggaccgcggc ggcggaggcg tggctggcgc    17340
agggcaaccg ggaccaggcg cgggtgctga tccacgagca gctcggcagg ccgggcacgg    17400
acagccgccg ggcgcgcggg caggcgctgc ggctgctcgc ggcgaccagc tcggtgaagc    17460
ggcacccgca gctgctgcgg gaggcggtgg cgtgttcga ggccgtcgac gacaagtacg     17520
agctggcgcg gaccctgcgc gacctgggga gggcgcagcg ggcgctgggc gagaacaagc    17580
tggcgcgccg ggtgatccgg cggggtggc acgtcgcccg gatgtgcgag gcggcgccgc     17640
tgtgcgagga gctgatgccc accgccgacg ggctggtgcc cgcgcagccc cgtcggcgg     17700
cccgcaggtc ggacctggac cggttgacca gctcggagca ccgggtggcc gcgctcgcgg    17760
cgtcggggct gacgaaccgg gagatcgcgg tgaagctgta cgtcacgcac agcacggtgg    17820
agcagcacct gacgcgggtg ttccgcaagc tcgggatcaa gcagcgggag cagctgccgc    17880
cggagctgag cgtcgaccgg tcgaagtgac gcggacgggg cggtcccgtg gatctggggc    17940
cgccccgtcc ggtcccggtc cgtccggtcc cgccctgtcc ggtcccgccc tgtccggtcc    18000
cgccccgtcc ggtcccggtc cgcctcaggc tcggggcatc gcggccaggg tggtggcgac    18060
gacgtgctct cgacgtcgc gcaccagctc ggccgccgc gggccgtcga gcacgaacgc      18120
caggccgccg gtggacttct tgtcgcggcg catgaaccgc agcagctcgt cgtccggcac    18180
gcccggcgga agcgcgacgg gcagcccgta gcccgcgacc acggagtggt gctcggccac    18240
ccggtccggg ccgatccggc cgagcgcgcc cgcgaggcgg ccggcgaaga ccgtgccgat    18300
cgcgacgccc tcgccgtgcc gcaccgcgaa accggtggcg agctccaggg cgtggccgag    18360
ggtgtggccg tagttgaggg tgtgccgcag gccggagtcg cgctcgtcgg cggccacgac    18420
gcgggccttg agggcgacgc tcgccgcac ctggtccagc agcggcagcc ggtccaggcc     18480
cggcgcgccg atgaagtggc agcgggcgat ctcgccgagg ccgttgcgca gctcgcgctc    18540
```

```
gggcagggtg gcgagcaggt cgaggtcgca cagcacggcg gcgggctgcc agtaggcgcc   18600
gacgaggttc ttgccctcgg ggaggttgac cgccgtcttg ccgccgacgc tcgcgtcgac   18660
ctgggccagc agcgaggtcg gcacgtgcac caccggggtg ccccggtggt agagcgaggc   18720
ggcgaggccg accgcgtcgg tggtggtgcc gccgccgcag gagacgacga cgtcggcgcg   18780
ggtcaggccg aactcggcga accggctgca caggtgggcg acggtggcga gggtcttgtc   18840
gtgctcgccg tcgcgggccg ggaggacgag ggaggggacg ccggggtcgg gcgtctggtc   18900
cgccgggcgg gcggtgacca cgacggcgcg gcgcgcgccg agggcccgca cgacgtccgg   18960
gagggcggcg cgcacgccgt gtccgatgtg gacggtgtag gcgcgctcgc ccagctcgac   19020
ccggacctcg cgggtggtgg cggcggtggg gcggggtgg gtggagctgg gcactgcttc   19080
ctcctcgggt gggcgggacg ggggcgatc ggggacgcg gaggggtgac gggaaagcaa   19140
tcgggcagga atgggaacgg gtccggggc gaacgggcag gaattcgaat ggggcaagc   19200 gaccgggagc gatcccagtg gtgggcgga agtgcgggcg gcgaaaggc ggtcgtgctg   19260 cctcagccgc cgcccgcggc gcccgtcacg agcgtggtgc gcagggtgag cgccgcccgc   19320
gccgccacgg ccgcgccgac gccgaggcgg ttgtgggtca gggtcgcctg ctcgaacagc   19380
accggcaggg ccgggcggcg gcggtccgcg gcggcgcgca gctgctccag gtagcgccgc   19440
cacgcgcccg ccgagccgac cacgcgcccg ccgggcggcg cccctgcgc ggcgacggcg   19500 gcctcggtgc gctcgaccgg gcggagcggc ctgctccagc tctgccagca gtggaacagg   19560
aacgcgggcc tggccggttc cggggccagc gcgaccagtt cggccaggtg gtgcagcacc   19620
gtggcctgcg cgcccgactc gccagggtcc tcgccccaca ccgggctcac caccgacgcg   19680
acgtccaggg ccagttcgct ggacgcggtc gcgaccagcg gctcgaccgg ccgccggc   19740 aggcccccac ccggcaggcc ctcgcccgcc gggtcgacgc gcaggtcgcg ggccgccgcc   19800
tcggcgcaca gcacggcgag caccggggcc cgcgcggcct cggtcgtgcc cagccacagc   19860
gccaccaccc ccgcccgcg caggaacgac cagtgcgcgc cccggtcccg cgcgcgcagc   19920
tcccgcacga cggggggcag cacctcggcc accgagcggg ctccaccgcc tgccagcgac   19980
cagcccgacc aggacggggc gcccgccgcc ggggtccgc cgaggggcgc tctcgcggaa   20040
ccggtccgcg tcatgtccac caccacttcc gccttggcga aacgggtcc tgcgggatca   20100 ccgcgctgtt ccgacgccgc cgacaatagc gacgcgcaat acgccgaatt caccgccaaa   20160
tcaggtcagg ggggttgagg gggatgcctt aggggcgag tgcccgcaaa gcggaagaag   20220
aatcggaagc acatgcagga gcgacttcca agctcaggcc gcaggaccgg gtccgcgtcg   20280
tcgcggacac cccggtcctg cgcgtgcgcg caccgaagga cgtggtgaca tgcttcggac   20340
cgacctgatc cgcccggttc ccgaactgct cggggccaac gcggatcgct tcggcgacag   20400
gaccgcctac tcggacggtc gccgttcggt cgggcacgcc gggctggaac ggcgcacgcg   20460
ccgcctcgcc ggtcacctcg gcagttgcg gctgcacccc ggcgaccgcg cgatgatctg   20520
cctgggaaat cgcgtcgaaa tgatcgagag ctatttcggc gtgctccgcg cggacgccgt   20580
ggcggtcccg gtgaacccgc gttccaccga cgcggagctg acccacctgc tcgccgacag   20640
cggggcccgg ctggtgatca ccgacgcggc gcgcgccgag cggttcgacc ggttgcgcgc   20700
cgagcggttc ggcgacctga ccgtgatcgc cacccaggac ggcccgctgc cgacggcgt   20760 catcgcgttc gagccgctgg ccgccgagga gccggagctg cccgcgcgcg acgggctcgg   20820
gctcgacgac gtggcctgga tgctctacac ctccggcacg accggcgcc caagggcgt   20880 gctgtccacg cagcgcagct gcctgtggtc ggtggccgcc tgctacgtgc cggtgccgga   20940
```

```
cctgcgcgcc gaggaccgcg tgctgtggcc gctgccgctg ttccacagcc tgtcgcacat   21000
cacctgcctg ctggccgcca cggccgtggg cgcgaccacg cgcatcgtgg acggcacgtc   21060
cgcgcaggac gtgctcgcgg cgctggagca ggagcggtcg acgttcctgg cgggcgtgcc   21120
gacgctgtac cggtacctgg tcgacgccgc ccgcgagcgc gggttcaccg ccccggacct   21180
gcgggtgggc ctggtcggcg gggcggtgac gacggcggag ctgctgcgcg cgttcgagga   21240
cacgttcggc gtgccgctga tcgacgccta cggcagcacc gagacgtgcg gggcgatcgc   21300
ggtgaactgg ccgaccgggg cgcgcgtggc gggctcgtgc gggctgccgg tgccggggct   21360
gacggtgcgc ctggtggacc cggagacgct gctggacgtg cccgccgggc gggagggcga   21420
gttctgggtg tcggggccga gcgtgatgct gggctaccac aaccagcccg aggcgacggc   21480
cgaggtgctg cgggacggct ggtaccgcac gggcgacctg gggcggcgcg acgaggccga   21540
gttctgcacg gtcaccgggc ggatcaagga gatgatcatc cggggtgggg agaacgtgca   21600
ccccggcgag gtcgaggccg tggtgcgggc ggtgccgggg gtggcggacg tcgccgtcgt   21660
gggcaagccg cacgacgtgc tgggcgaggt gccggtggtg ttcgtggtgc cgggcgcggg   21720
cgggttcgac ccggcggcgg tgctggcggc gtgccgggag gagctgtcgt acttcaaggt   21780
gcccgaggag gtctacgaga tcgagcgggt gccgcgcacg gcgtcgggca agaccacccg   21840
gcacgtgctg ctggacctgc ccgcccggtt gcggcggcg tcgagcgggc agttccagtc   21900
gctgctgcgg ctggactggg tgccgaggac ggcgctgccg ggtgaggagg tcccggcgag   21960
ctgggtgctg gtggacggcg acccgctggg gctcgcggac gggttgcggg ccacgggcgc   22020
gcgggtgcgg gtgggcgagc cgggcgcgga tgcgctgggc gacggcggat cggacgccga   22080
cgagccgggc gcgagcagcg cgggcgaacc gggctcgggt ggctcgggtg agccgggctc   22140
gggtggctcg ggcgaaccgg gctcgggtga accgggcgcg agcagcgcgg gtgagccggg   22200
tgcgggtgag ccgggcgcgg ccgaaccccc gcaggtcgtg ctggtcgccg cggtccccgg   22260
tgagcgtggt gaggtcgcgc gggacgtgga ggcgctcgcg gacgggctcg cgcggcggct   22320
cgtcgggtgg ctggccgacg agcggttcgc ggggcgcgg ttcgtcgtgg ccacctcggg   22380
cgcggtgtcg acctcccccg gcgaggacct gcggagctg cgggcggccc cgctgtgggg   22440
tgtggtgcgg tcggtgcagg ccgcgttccc cggtcgggtg gtggcggccg acctggacgc   22500
gtccggcgac gggcgggcgg cggcgctggc tcgcgtcgtc gcgggcgggc acgaccaggt   22560
ggccgtgcgc ggcgacgtgc cgctggcgcc ccggctggcc agggtgtccg tgccgtccga   22620
cccggccccc gccccggcgc tggacccgga cgggctggtc gtggtcaccg gtggcgactc   22680
ggcgcgcggc gcggccctcg cgcggcacct ggtggccgcg cacggcgcgc ggcgcctgct   22740
gctggtctcc cccgacgggc tgcccgacca ggccgccgcc gacctggagg ccgggttcgc   22800
ggcggcgggc gcgcgggcgg agtcggtggt gtgcgacccg gccgaccgg tcgcgctgcg   22860 cgccctgctc gacgcgcagg accgcccggt cacggccgtg gtgcacgtgc agggcgggcg   22920
ggcgctgctg gactcggcgc gcgccctcgt cgccctgcac gagctgaccc gccaggcgcg   22980
accggcgctg ttcgtcgtgg tcacctcggt ggccgggctg ctgggctcgg cgggcgaccc   23040
ggcgcgcgcg gcggccgacc agttcgccga ggcgctggtg cgcaggcgcg ccgaccgggg   23100
cctgccgggg ctggccgtgg cctggggtcc gctgccgggc gagcccgcgc aggcgggcgc   23160
gggcgcgctg ccgatggccg aggcgctgac cctggtcgac gccgcgctcg ccgccgacca   23220
gggcccgctg gtggtgctcg ggctcgacgg ggtcgggtcg cggcgcgcgg tgggcgcggt   23280
gccgccggtg ctgcacgacc tggtcgacgg cggtcgcgcc gcgcgggtcg cgccgggcgc   23340
```

```
ggtggccgag ttcacgcgca ggctcgcgga ggcgggtggg cagcgggccc gacgcgtcgc   23400
gctggacctg gtgcgcgagc acgtcgcggc ggcgctcggc ctgcccgagg acaccccggt   23460
gcgcgccgac caggcgttcc gcgacttcgg cgtcacctcg ctgaccgccg tggcgctgcg   23520
cgaccggatc aacgccgcga ccggcgcgtc cctgcccgcg acggcggtgt cgaccaccc    23580 gaccccggcc gcgctcgccg accacctggt gcgcgaggtc accggcgacc ggccgcacgt   23640
cgagcgggcg cgggacgagc gggcgcgcgg gacctcgcgc gcggacgagc cggtggcgat   23700
cgtcgccatg gggtgcaggc tgcccggcgg cgtggcctcg ccggaggacc tgtggcggct   23760
ggtggacgag ggcgtcgacg cgatcggccc gttcccgacc gaccggggct gggacctggc   23820
caccctgctc gacggctcgg actcgccggg gaggtcctcc gtggaccgcg gtggtttcct   23880
gccgggcgcg ggcgacttcg acgccgggtt cttcggcatc tccccgcgcg aggccctggc   23940
catggacccg cagcagcggt tgctgctgga ggtggtgtgg gagaccgtgg aacgcgccgg   24000
gatcgacccg cgctcgctgc acggcgaaga cgtcggcgtg ttcagcggcc tgatgtacca   24060
cgactacggg accgaacccg gttccgcgcc ggagggcctg gaggggttcg tcagcaccgg   24120
cagcgcgggc agcgtggtct ccggccgcgt cgcctacgcg ctcggcctga ccggcccggc   24180
gctgaccgtg gacacggcgt gctcgtcgtc gctggtggcg atccacctgg cggcgcaggc   24240
gctgcgctcg ggcgagtgct cgatggcgct cgcgggcggg gtcgcggtga tggggcagcc   24300
gacgtcgttc gtggagttct cccggcagcg cgggctcgcc gccgacgggc gctgcaagtc   24360
gttctccgac gacgccgacg gcacgaactg ggccgagggc gtgggcgtgc tgctgctgga   24420
gcggctctcg gacgcgcgcc gcgacgggca cccggtgctg gcggtgctgc gcggcagcgc   24480
ggtgaaccag gacggggcca gcaacgggct gaccgcgccc agcggcccgg cgcagcagcg   24540
ggtcatcagg caggcgctgg cgaacgccgg gctgcgaccg tccgaagtgg acgccgtgga   24600
ggcgcacggc accggcacca ccctgggcga cccgatcgag gcgcaggcgc tgctcgccac   24660
ctacgggcag gaccgcgagc agccgctgtg gctgggctcg ctcaagtcca acctcggcga   24720
cgcgcaggcg gcggcgggcg tcgcgggcgt gatcaagatg gtgatggcgc tgcggcacgg   24780
cgtcctgccc cgcaccctgc acgtcggcac gccctcgtcc aaggtcgact ggtcggcggg   24840
cgcggtcgag ctgctgaccg aggccaggcc gtggcgcgcg aacgggcggc cacgccgggc   24900
gggcgtgtcc tcgttcgggg tcagcggcac caacgcgcac gtcgtggtgg aggagcaccg   24960
ggaaccggcc gccgcgccgg tcgacccggt ctccccggc ctggcggtca gcggcggcgt    25020
cgcgccgctg tgctgtccg gcgcacccg ctccgcgctc gccgcgcagg ccgcggccct     25080
gctggggcac ctggccgacg ggaccgaccc ggcggcgctg ggccgcgcgc tcgccaccac   25140
ccgcaccgcg ttcgagcacc gggccgcggt cctcgcgccg gacgtcgacg ccgcgcgcgc   25200
cggggtgcgc gcgctcgccg aggaccggcc cgcgccgaac ctggtcaccg gcaggccga    25260 cgtgacggc ccggtcgtgt tcgtcttccc cggccagggc gcgcagtgga ccggcatggg    25320
ccgggagctg ctggagacct cgccggtgtt cgccgcgcgg ctgcgcgagt gctcggaggc   25380 gctgagcgg tggaccggct ggtccctgct cgacctgctc gccgacgggg cggagctgga    25440
ccgggtcgac gtgctccagc ccgcctcgtg ggcggtgatg gtggcgctgg ccgcgctgtg   25500
ggagtcgtgc ggggtgcgcc cggacgccgt ggtcgggcac tcgcagggcg aggtggccgc   25560
cgcgtgcgcc gccgggtggc tgtcgctgga cgacgcggcc agggtggtgg cgctgcgcag   25620
ccgcgcgatc gccgagcacc tggccggcg cggcggcatg atgtccgtcg ccgcggggc    25680 ggagcgggtg gccgggctga tcgccgaccg gcagggccgg gtgtcggtgg ccgccgtgaa   25740
```

```
cgggccgtcc gcgaccgtgg tggccggggc cgccgacgcg ctgcccgagc tggccgcgcg   25800
ctgcgagcgg gagggcgtgc gggcccggat catcccggtg gactacgcca gccacaccga   25860
gcacgtggac gcgctcgacg gggtgctgca ggaggtgctg gcgggcgtca ccgcgcaggc   25920
cgggcacgtg ccgtggctgt ccaccgtgga cggcgagtgg gtcgacggct cggggctgga   25980
cgcggactac tggttccgga acctgcgcgg gaccgtgcgg ttcgccgacg cggtggcggc   26040
gctggcgggc tccgggcacc gggtgttcgt ggaggtgtcc agccacccgg tgctcaccgc   26100
cgcgaccggc gaggtgctgg aggccgccgg ggtgcgcgac gcgctggtgg tcggctcgct   26160
gcggcgcgac gacggtggcc ccgagcggtt cctcaccggg ctcgccgagc tgcacgcgcg   26220
cggcgtcccg gtgggctgg aggcggtgtt cgcgggcgcg acgggcgggg tggagctgcc   26280
gacgtacgcg ttccagcacg agcggtactg gctggcgcgc ggcccggtgg ccggggacgt   26340
gtccgggtcg gggctggtgg acgcggcgca cccgctgctc ggggcggtcg tgccgctgcc   26400
gggcacgggc ggggtgctgc tgtccggccg gctctcgcac cggcggcagc cgtggctggc   26460
cgagcacgcg gtgccgggga cggtgctgct gccgggcgcg gcgatcgtgg agctggccgt   26520
gcgcgcgggc gacgagaccg ggtgcggggt gctgcgggag ctggtgatcg ggcagccgct   26580
ggtggtgccg ccggacgccg aggtggacct gcaggtgctc gtcggcggcc cggacgacgg   26640
gggcgtgcgg gacctgcggc tgtactcgcg gaccggggcg gcggcggagt gggtcgagca   26700
cgcggcaggc gcgctcgccc ccggcggcgc ggtcggcggg gcgcgaccgg ccggggcgcg   26760 gacgccggg gcgcgactgg acggggcgcg actggacgga cagtggccac ccgcgggcgc   26820
ggaacccgtt gcgctggaag gcttctacga gaacctggcg gagctgggct acgagtacgg   26880
gccgctgttc cggggctcg cggcggcgtg gacgcgcgac ggcgaggtgt cgccgaggc   26940 cgtgctgccc gaggaggcgt tgtccgggca ggcgttgtcc gggcaggcgg ggtccgggca   27000 ggcgggtcc gggaacgggt ccgggaacgg gttcggcatc cacccggccc tgctggacgg   27060
ggcgctgcac gcgggcaacc tgtgcgtgcc gcccgcgccg ggccggacgc tgctgccgtt   27120
cgcgtggaac gaggtgcggc tgcacgccac cggggcgacg gcggtgcggg tgcgcgtgcg   27180
ggcgaccggc gaggactccc tggagctgga gctgttcgac gccgacggcg cgcccgtggc   27240
gagcgtcggc gggctgaccc tgcgaccggc ggtcacgggc gcgcgccgg ccgagtcgct   27300 gcacgaggtg gagtggaccg aggtcgcggc gggcggttcg tggccggagg tcgccgacac   27360
ccgcgactgg gaggccgccg ccgacctgcc gacccggtcg cgcgagctgg ccgcccgcgc   27420
gctggaactg gtgcaggacc ggctggcggg cgtggacggc gcaccgctgc tggtgatcac   27480
cacgggcgcg gtggcggtgg ccgacgacgc cgaggtcacc gacccggccg ccgccgccgt   27540
ctgggggctg ctgcgctcgg cgcagtccga gcacccccgc cggttcgcgc tggtcgacgt   27600
cgacggcggc gcggcggccg aggtcgccgc gctcgtgccc ggcgacgagc cgcagaccgc   27660
gctgcgcggc gggctcgtgc gggctccgcg cctgcgccgc ctgcccccg gtctcgtgcc   27720 gcccgccggg gcgcactggc acctggacgc agtcaccacc ggcacgctcg acgggctcgc   27780
gctcgtggcc tcggaaccgg tcccgctgcg ggccggggag gtgcggatcg aggtcagggc   27840
ggccgggcag aacttccggg acgtgctggt ggcgctggac ggcgtcgcgg gccaggaggg   27900
catcggcggc gagggctccg ggatcgtgac cgaggtcggc cccgaggtga ccggattcgc   27960
cgcgggcgac cgggtgatgg ggctgttccc gcgctcgttc gggccgctgg ccgtggccga   28020
cgcccgcacg gtggtgcggg tgccgcgcgg ctggtcgttc accgacgcgg cggccgtgcc   28080
ggtcgcgttc ctgaccgcgc tgcacggact ccaggacgtc gccgggctgc gggccgggga   28140
```

```
gacggtgctg gtgcacgcgg cggcgggcgg cgtcgggcag gccgccgtgc agctcgccca   28200
ccacttcggc gcgcgcgtgc tggccaccgc gcacccggcc aagcacagcg tgctgaccgc   28260
gctgggcgtg cccgccgagc ggctcgcctc cagccgcgac ctcggctacg cgcggcggtt   28320
cggcgacgtc gacgtggtgc tgaactccct ggtcggcgag cacgtcgacg cctcgctgcg   28380
gctgctgcgc gcgggcggcc ggttcgtgga gatcggcaag aacgacgtcc gggacgccga   28440
ctcggtcggg gacgtccgct accgggtgtt cgacctgggc gcggacgccg ggccggaccg   28500
gatcggcgag ctgctggagc agctggtggg cctgttcgag tcgggcgcgc tgcggccact   28560
gccggtcgcg acgtgggacg tcacccgcgc ggcctcggcg ttccgcgaga tgagccgggg   28620
cgggcacacc ggcaagatcg tcctgacgat cccgcgccgc ctcgaccccg agggcacggt   28680
gctgatcacc ggcggcgccg gcacgctcgg ggccaccgcc gccgccacct ggtcaccgc    28740 gcacggcgcg cggaacctgc tgctggtcgg caggcggggc cccgacgcgc ccggcgcgag   28800
cgagctggcg gaggagctgc gcgggctggg cgcggacgtg cgggtggcgg cgtgcgacgt   28860
cgccgaccgg gccgcgctcg acgccctgct cgcctcggtc ccggccgggc gcccgctgac   28920
ggcggtcgtg cacgcggcgg gcgcgctcga cgacggcacg gtcaccgcgc tcaccccgga   28980
gcggttcgac gcggtgttcc gccccaaggt ggacgcgatc gcgcacctgg acgaggcgac   29040
ccgcgacgcc gacctggccg cgttcgtcgt ctactcctcg gcggcggggcg tgctcggcaa   29100 cgcggggcag ggcaactacg cggcggcgaa cgccgtgctg gacgcggtgg cccgcacccg   29160
gcacgcccgc gccctcccgg cgacctcgct ggcctggggg ttgtggagcg acacgagcgc   29220
gctgaccgcg acgatggacg ggcgcgcggt ggaccgcacg cggcgcgcgg gcgtgctggg   29280
catgggcaac gacgaggcgc tggcggcgct ggacgcgggc ctggcgtccg ggctgcccgc   29340
gctggtggcc gcccggatcg acccggccgc gctgcgcgac cccgcgtcgg ggtcgccgct   29400
gctgcgcggg ctggtgcgcg ccacccgccg cacggccgcc accgcgacc gggacgccgt    29460 gggcgggctg gccggacggt tggccgggtt gtcggccgcg gagcaggacg agctgctgct   29520
gggcctggtg cgcagcgagg ccgccgccgt gctcgggcac gcgagcgccg agcgggtcga   29580
gccgcaggtg gcgttccggg acatgggggtt cgactcgctc accgccgtgg agctgcgcaa   29640
ccggctcgcg gcggcgaccg ggctgcggct gcccgcgacg gcgacgttcg accacccgac   29700
gccggtgcgg ttcgccgcgc tgctgcgggg cgagctgctg gcgccgtcg tggctcccgg    29760 agccgtgacc gccgccgcgg ctcccgtgac cgccgccgcg cccgccgacg agccgatcgc   29820
gatcgtgtcg atggcgtgcc ggctgccgg cggggtggtc gacccggccg gctgtgtgga    29880
gctgctcacc ggggagcggg acgggatcgt ggacttcccc gacgaccggg gctgggacct   29940
ggagtcgctc taccacccgg acgccgactc ccccggcacc tcctacgtgc tgcgcggcgg   30000
gttcctggac gacgcgggcg ggttcgacgc cgggttcttc ggcatctccc cgcgcgaggc   30060
cctggcgatg gacccgcagc agcgggtgtt cctggagacc tgctgggagg cgttcgagcg   30120
cgccgggatc gacccggtct cggtgcgcgg cagcgacacc ggggtgttcg ccgggatcat   30180
cgaccaggac tacggggtgc gcgcgggcac ggccccgag gagctggagg ctacctgct    30240 caccggcacc gccacgtcgg tggcgtccgg gcgggtggcc tacctgttcg gctggagggg   30300
cccgccggtc accgtggaca cggccgtgctc gtcgtcgctg gtggccacgc actgggcggt   30360
gcaggcgctg cgccggggcg agtgctcgat ggcgctggcg ggcggcgcga ccgtgatggg   30420
gcggccgtcg gcgttcgtgg agttctcccg gcagcgcggg ctggcgcggg acggaactg    30480 caaggcgttc ggcgcggacg cggacggcac cgcgttcagc gagggcgcgg gcgtgctgct   30540
```

```
gctggagcgg ctctcggacg cgcggcggcg cgggcacccg gtgctcgcgg tgatccgggg    30600
gtcggcgctg aaccaggacg gggcgtcgaa cgggctgacc gcgcccagcg gaccggcgca    30660
gcagcgggtg atccgggcgg cgctggccga cgcgggcctg cggccgtcgg acgtggacgc    30720
ggtggaggcg cacggcaccg gcaccgcgct cggcgacccg atcgaggcgg gcgcgctgct    30780
ggcgacctac ggcgcggacc gggagggcgc ggaaccggtg tggctggggt cgctcaagtc    30840
caacaccggg cacacgctgg cggcggcggg cgtgtcgagc gtgatcaaga tggtgctggc    30900
gctgaaccac ggcctgctgc cccggtcgct gcacgtgcgg gagccgagcg cggcggtgga    30960
ctgggagtcg ggcggcgtgc gcctgctgac gagcgcccgg ccgtggccgg agagcggcag    31020
gccccggcgg gcggggggtgt cgtcgttcgg gatcagcggc acgaacgccc acctggtgct    31080
ggaagccgcg cctgcggagg agggcgcggg ggcgcggagt ggggcggcgg cgccgggacc    31140
ggacacccgg tcggcgccca ccccggacgc cccagcgggc cccgtccaga cctccggcgt    31200
gatcccctgg ccgttgtcgg cccgctccgc cgacgcactg cccgcgcagg ccgcgaagct    31260
ggccgcccac gtgcgggcgc acgacgacct ctcgccgctc gacgtcggct ggtccctcgc    31320
gaccacccgc accgcgcacc cgcaccgcgc cgtgctcgtc ggcggcaccc gcgaggcgct    31380
gctgtcggcc gccgacgcgc tcgcgggcgg cgaggccagc caggccgtgc tcaccggctc    31440
cgccgtcggg tcgggttcgg cgaagaccgt gttcgtgttc cccggccagg gcgcgcagtg    31500
ggcgggcatg ggccgtgagc tgctggggtc ctcgccggtg ttcgccgcgc ggctgcgcga    31560
gtgcgccgac gcgctggccc cgcacaccga ctgggacctc ctggacgtgg tgcgcggcgc    31620
ggagggcgcg ccggggttcg agcgggtcga cgtgctccag cccacctcgt gggcggtgat    31680
ggtggcgctg gccgcgctgt ggcgctcgtg cggggtggag ccgtccgccg tcgtcggcca    31740
ctcgcagggc gaggtggccg ccgccgtggt cggcgggtac ctggcgctgg gcgacgcggc    31800
gcggctgatc gcgcggcgca gcagggccat cgcgcaggag ctgaccgggc gcggcgggat    31860
gctgtccgtg ctcacctcgc ccgagcgggt cgccgaactg ctggagccgt gggccgggaa    31920
gctgtggatc gcggcggtca acagccccgc gtccgtctcg gtgtccggtg acgccgaggc    31980
gctgggcgag ttcgtgcggg tgctggccaa ggcccggatc aaccggtggc ggctgcccgg    32040
cgtggacttc gccgggcact ccgggcacgt cgacggcatc gaggcgcggc tgcgcgagga    32100
gctggccgac gtcaccgccg cggcgggcga agtgccctgg ctgtccaccg tggacgggcg    32160
gtgggtggag cgcaccaggc tggacgccga ctactggtac cgcaacctgc gcgacgtggt    32220
ccgcttcgac gaggccgtcc gcgcgctggt ggacgccggg caccgggcgt tcgtggaggt    32280
ctccacgcac ccggtgctga ccaccgcgat cggcgaggtc gccgacgagc ggcaggacgt    32340
gcgggtcgcc gtgcgcggca cgctgcgccg cgacgacggc ggcgcggacc gggtcgtggg    32400
cgcgctcggc gaggtggccg cctcgggcgt ggcggtggac tgggcggcgg tgttcggcgg    32460
gaccggggcc gcggtggtgg agctgccgac gtacgcgttc cggcacgagc ggttctggct    32520 cacccccgtcc ggcggcgacg tgcgcgcggt ggggctgcgg caggccgggc acccgctgct    32580
gggcgcggtg gtcagcgtcc cggacaccgg cggcgtgctg ctgaccgggc ggctgtcgct    32640
gtccgcgcag ccgtggctgg ccgaccacgc gctgtccggc gtgccgctgc tgccggggac    32700
ggcgctggtg gagctggcgg tgcgcgcggg tgacgagacc ggcacgccgg tggtggcgga    32760
gctggtgctg ggcaggccgc tcgtgctgcc gcgcaccggg tcggcgcagg tgcaggtgct    32820
ggtgggcgag gaggcgcggg acgggcggcg gccggtcgcg gtgtactcgc gggcgggcga    32880
cgaccggccg tggaccgagc acgcctcggg ctcgctcgcg ccggacagag gacgccgcgcc    32940
```

```
gggagcggag ggcgacgagt ggccgcccgc cggggccgag ccggtggacc tcggcggctt   33000
ctacgacggc ctcgccgaac gggctacga ctacggcccg gccttccggg gcctggtgcg    33060
cggctgggtc aggggcgacg aggcgttcgc cgaggtcggg ctgcccgacg accagcacgg   33120
cgcggcggcc cggttcgggc tgcacccggc gctgctggac gcggccctgc acgcggcctc   33180
gctgtgcgcg ggccacggcc ggggcacggc gctgccgttc acctggaccg gcgtgcggct   33240
gcacgcggcc ggggcgacgg cgctgcgcgt cgggctggag gcggacgggc cggagcggtt   33300
gtcgctgcgg gcgagcgatc cggcgggcac gcccgtggtg accgtcgggt cgctgctgct   33360
gcgcgccgcc gacgcggacc ggctgcgggc gacagcggcg cgacggcgg cagcggcggc    33420 ggacgacggg ctgcacgcgc tggagtggac cccgcacccg ctgcccgagg agacgaccgg   33480
ttcccccgcc gtcctggaca ccagggcgtg ggagctgccc gagggcgtcg ggcgggccga   33540
ggcgatcacc acgcgggtgc tcgccgagct ccaggccgag ctcgacggga cggcgaccct   33600
ggtcgtggtg acgcggggcg cggtggccgt gcatgacgac gccgaggtca ccgacccggc   33660
cgccgccgcg gtgtgggggc tggtgcgcgc cgcgcaggcc gaggaacccg gacgcgtcgc   33720
cgtggtcgac gtcgacgacg cctccgaggc gcgctggac gccgccgcgc acgccgcggg    33780
cgcagaaccg cagctcgccc tgcgcggcgg ggcggcgttc gcgccgaggc tggtcgaggc   33840
gtccggggcg ctggccgtgc cggacgggcc gtggcggctc gacagcaccg gccggggcac   33900
cctggagaac ctggcgctcg tgcccaaccc cgccgccggg gcgccgctcg cgcccggtca   33960
ggtgcggatc gtggtgcggg cgggcggcct gaacttccgg gacgtgctga tcgcgctcga   34020
cgcctacgag tcggagatcg gcaccgaggg cgcgggcgtg gtcgtggagg tcgcgccgga   34080
cgtcacccgc gtggccgtgg gcgaccgcgt gatgggcatg atccccggct cgttcgggcc   34140
gctggccgtg gccgacgccc gcacggtggt gcggatgccg cgcggctggt cgttcaccga   34200
cgcggcgggc gtgccggtcg cgttcctgac cgccctgtac gggctgcgcg acctcggcgg   34260
cctggcggag ggcgagaccg tgctggtgca cgcggcggcg ggcggcgtcg gcatggccgc   34320
cgtgcagctc gcccggcact tcggcgcgcg cgtgctgggc accgcgcacc cggccaagca   34380
cgccgcgctg gacctgcccg ccgaccacct ggcctccagc cgggacctcg cctacgcgca   34440
gcggttcggc gacgtcgacg tggtgctgaa ctccctggtc ggcgagcacg tcgacgcctc   34500
gctgcggctg ctgcgcgcgg gcggccggtt cgtggagatg ggccgggcgg acctgcgcga   34560
cgccgacgag gtggcgcgcg agcaccccgg ccgcgcctac ctcccgttcg acctcggcgg   34620
cgacgccggg ccgaccggga tcgccgagct gctggtggag ctggtggccc tgttcgagtc   34680
gggcgcgctc cgcccgctgc cgacccggcg caccgacctg gtgcgcgccc ccgaggcgtt   34740
ccgggccatg agccagggcc gccacgtcgg caagctcgtg ctcacccccgc ccgcgcgct    34800 cgaccgcgac ggcacggtcc tgatcaccgg cggcacggga accctcggcg cggctctggc   34860
ccgccacctg gtgacgcgc acggcgtccg gaacctgctg ctggtcagcc gcagcggccc    34920
caacgcgccg ggtgcggccg acctggtcgc ggagctggcc gagcggggcg cgagggtccg   34980
ggtggccgcg tgcgacgtgg ccgagaagga cgcgctcacc gcgctgctcg cctcgatccc   35040
caccgggcgc ccgctcaccg gcgtcgtgca cgcggcgggc gcgctggacg acggggtgct   35100
caccgccctg gacgccgacc gggtcgcggc ggtgctgcgc cccaaggccg acgccgccct   35160
gctgctgcac gaggccaccg aggacgccga cctcgcgctg ttcgccctgt gctcgtcggt   35220
ggcgggcgtg ctgggcaacg cgggccaggc gaactacgcc gccgcaaaca cctacctgga   35280
cgcgctggcc cagcaccggt cggccgccgg tctggccgcg ctgtcgctgg cctggggccg   35340
```

```
gtgggcgcag accagcgccc tcaccgcaga cctgcccgcg cccggcggtc gccgcgacct   35400
ggtgcgcccc atggacaccg cgtccgcgct gcgcctgctc gacgccgcgc tccgcaccgg   35460
acgctcgacg gtcgtcgccg ccgagctgga cgtcacggcg ccaccgccg  cgaacccggt   35520 gctgcgcggc ctggtccggc ccgcccggcg cgcgctggcc acgtccgcgc gggacgagcg   35580
cggcgtggcg gcggcgctgg ccgggctggg cgaggccgac cggcgccggt cgtgctgga    35640 cctggtcgcg tcgcacgccg ccgtcgtgct gggcctggcg ggcaaggagg ccgtggacgc   35700
cgagcgcgcg ttcaccgaga ccggcttcga ctcgctcacc gccgtggagc tgcgcaaccg   35760
gctcgccgcc gcgaccgggc ttcggctgcc ctccacgctg gtgttcgacc acgccacccc   35820
gaccgcgctg gccgcgcacc tgcgcgccga gctgaccggc gacgacctgc cgcaggcgcg   35880
ggccgtcgcc gccacggcgg gggcgcggga cgacgacccg gtggtgatcg tgtcggcgag   35940
ctgccgcctc cccggcggcg cggactcgcc ggaggcgctg tgggagctgc tggagcgggg   36000
cagggacgcc atcaccccgt tcccgcgcga ccggggctgg gacctggagg cgctctacga   36060
cgccgacccg gaccggccgg gcaagagcta cgtgcgcgac ggcgggttcc tcgccgacgc   36120
ggccgggttc gacgccgagt tcttcggcat ctccccgcgc gaggcgctgg ccaccgaccc   36180
gcagcagcgg ctgctcgccg agacctcctg ggagctgttc gaacgcgcgg gcatcgcccc   36240
gacctcggtg cgcggcagcg acgtcggcgt gttcgcgggc gtgatcaacc aggagtacgg   36300
cgtgcacagc ggcacgaccc ccgccgagct ggaggggtac gtgatgaccg gctcgaccac   36360
cagcatcgcc tccggccggg tggcgtacct gctcggctg  accgggcccg ccgtcaccgt   36420
ggacaccgcg tgctcctcgt cgctggtggc gatccacctg gcggcgcagg cgctgcgctc   36480
gggcgagtgc tcgatggcga tcgcgggcgg cgcgacggtg atcgcgaggc cgggcgggtt   36540
cgtctcgttc tcccggcagc gcggcgcggc ccccgacggg cgctgcaagg cgttcggcga   36600
cggcgcggac ggcatggcgt tcgccgaggg cgtcggcctg gtgctgctgg agcggctctc   36660
ggacgcgcgc cgcaacgggc acccggtgct ggcggtcgtg cgcggcacgg ccctgaacca   36720
ggacggcgcg tccaacggcc tgaccgcgcc gaacgggccc gcgcagcagc gggtgatccg   36780
gcaggcgctg gccaacgccg ggctgtcccc cgacgaggtg gacgcggtcg acgcgcacgg   36840
caccggcacc gcactcggcg acccgatcga ggcgcaggcg ctgctcgcca cctacgggcg   36900
ggaccgggac ccgcgcggc  cgctgtggct ggggtcggtg aagtcgaaca tcgggcacac   36960
ccaggcggcg gcgggcatcg cgagcgtgct caagatggtg ctggcgatgc agcggggcgt   37020
gctgcccgcg accctgcacg ccgacacccc gacgacgaag gtcgactggt cctcgggcgc   37080
ggtggcgctg ctgtcgcggg cgcggccgtg gccggagacc gggaggccgc gccgggcggg   37140
cgtgtcctcg ttcgggatct ccggcaccaa cgcgcacgtg ctgctggagc aggcccgca   37200 ggacgcgccc gccacgccgg tcgccccgcg gggcgccggg ctggtcgggg cggtggcctg   37260
gccggtgtcc gggcgcacgc ccgccgcgct gcgcgcccag gccgccaggc tcgggacgca   37320
cctggcgggc gcgcaggccg gacccgccga cgtgggctgg tcgttggcgg gcacgcggac   37380
ggcgttcgcg cagcgggcgg tcgtggtggc cgggacggcg gagcaggccc gtgacgggct   37440
ggcggcgctg gccgaaggcc gctcgtccgc gctcgtgacg accggtgagg ccggggtcga   37500
cgggcgcgtg gtgttcgtgt tccccggcca aggggcgcag tggatcggca tgggcgcgga   37560
gctgatcgac gcgtcgccgg tattcgccga gcggttgcgc gagtgcgcgg aggcgctgga   37620
accgttcgtg gacttcgacc tgatcgaggt gctgcgcgga cgcgggtcgc tggagcgggt   37680
cgacgtggtg cagcccgcgt cgtgggcggt gatggtgtcg ctggcagcgc tctggcggtc   37740
```

```
gctgggcgtg gaaccggacg ccgttgtcgg gcactcgcag ggcgagatcg cggcggcggc   37800
ggtcagcggg gcgctcagcc tgcccgacgc cgcagccgtg gtcgcgttgc gcagcaaggc   37860
gatcgcccag gacctggccg ggctcggcgg catgatgtcc gtcgccctgc ccgccgacga   37920
cgtcgacctg agcgggtatc ccggacgcct gtgggtcgcc gcgcacaacg gccccacctc   37980
gaccgtggtg gccggtgacg tggacgcgct gcgcgagctc cacgcccact acgagggcgc   38040
cgaggtccgg gcccggatca tccccgtcga ctacgccagc cacaccgggc acgtcgacac   38100
catccgcgag cggctcgccg aggcactggc gcacgtgcgg ccgagggcgg gcacgatccc   38160
gtggctgtcg accgcgaccg gcgagtggac caccggtgag gacgccgacg ccgactactg   38220
gttccgcaac ctgcgcggcg cggtgggctt ccacaccgcc atcaccaccc tcgccgagca   38280
gggccaccgg gtgttcgtgg aagtctccag ccaccccgtg ctcaccaccg ccatcgaggc   38340
cacgctcgaa ggaaccggac ccaccgccgt caccggaacc ctccgccgcg acgacggcgg   38400
ccccgaccgc ctcctcacca gcctcgccac cctgcacgtg cgcggcgtcc acgtcgactg   38460
ggacgcggtc tacgcgggca gcggcgcgca ccgcacgacg ctccccacct acgcgttcca   38520
gcacgagcgc tactggctca ccgagccgga cgcgccgcag gccgtcgcgg acgcccgtt   38580
ctgggacgcc gtggacagcg cgacgtggc cgcgctcgcc gggtccctgg gcgtcgagcc   38640
cgccgccctg gagccggtgc tgccggggct gacgagctgg cgggcccgca accgggacgg   38700
cgcggccgtg gacgactggt cctaccggat cggctgggag cgggtggacg tgcccgccgc   38760
cccgctgtcc gggacgtggc tggtcgtggt gcccgaggca ctcgccgacg acacctcggt   38820
cgccgaggtc gcggcggcgc tggccgcgcg cggcgcgacg ccgaggatcg tggcggcggg   38880
cccgacctg gcccggacc tgggtgacga gccggacggg gtgctgtcgc tgctggcgtg   38940
ggacgaccgc ccgccggggg gcggcacgct ctcgcgcggc gtcgtggacg cggtcgggct   39000
ggtgcgggag gcggtgcggc gcggctggtc ggccccgctg tggtgcgcca cgctcggcgc   39060
ggtcgccgtc gccgaccccg gcgaggtgac ggccgagttc gggccgcagc tgtggggcac   39120
gggcgtcgtg ctgggcctgg acctgccgga cacctgggt ggcctggtcg acctgcccgc   39180
gcggccggac ggggtcgcgc tggacctgct gtgcgcggtg gtcgcggggcg cgggcgacga   39240
ggaccagctg gcggtgcgcc cggcggggt gttcgcgcgg cgcatgaccc gacgcccggt   39300
cgcgtcggcg cccgcgtggc gaccgcgcgg gacggtgctg gtcaccggcg gcaccggcgg   39360
cctcggcggc tacgtcgccc ggtgggcggc ggagcggggc gcgcgggacg tggtgctgct   39420
ctcgcgcggc ggcccggacg cgccgggcgc ggacgccctg gtcgccgaca tcacggcggc   39480
gggcgcccgc tgcgcggtgc tggcctgcga cgtcaccgac cgggacgcgc tggccgaggt   39540
ggtcgcgaac ctgccggacg ggccgctgtc ggtggtgcac gccgcgggcg tggcgcgacc   39600
gggacggccg ctggtggaga ccacgccgga ggagttcgcg gccatcggcc ggggcaaggt   39660
cgcgggcgcc cgcctgctgg acgagctgct gggcgaccgg gagctggacg cgttcgtgct   39720
gttctcctcc ggcgcggcgg cctggggcag cggcgggcag gccgggtacg cggcgggcaa   39780
cgccttcctg gacgggctcg cgcagcgcag gcgcgcccga gggctcgcgg ccacctcggt   39840
ggcctggggc gcgtggggcg gcgtcggcac ggtcgacgag gtgctgggcg agcagtggcg   39900
gcgcgccggg ctgctcacca tggacccgcg cctggccacc ctcgccctcg cgcacgccgt   39960
gggctcgggc gaggcgcacc tgctcgtcgc ggacgtcgac tgggcccgct tcgccccgc   40020
ctacgcgctg gccaggccgc gcccgctgct ggcggcgctg cccgaggtcg ccgacgcgct   40080
ggcggtcgtg gacgcgcccg ccgacgccgg ggggatcggg gcgcggctgg ccgggctgcc   40140
```

```
gcccgccgag caggagcggc tgctcaccga gctggtgcag gcggaggcgg cggccgtgct    40200
gggcctgggc ggcatcaccg gcgaccgggc gttccgggag gtcgggttcg actcgctcac    40260
ggccgtggag ctgcgcaacc ggctcggcgc ggccacgggt ctcaccctgc ccgcgacgct    40320
ggtgttcgac caccccgcgcc cgagcgccct ggccgcgcac ctgcggtccg cgctgggccc    40380
```

```
gcccgccgag caggagcggc tgctcaccga gctggtgcag gcggaggcgg cggccgtgct    40200
gggcctgggc ggcatcaccg gcgaccgggc gttccgggag gtcgggttcg actcgctcac    40260
ggccgtggag ctgcgcaacc ggctcggcgc ggccacgggt ctcaccctgc ccgcgacgct    40320
ggtgttcgac caccccgcgcc cgagcgccct ggccgcgcac ctgcggtccg cgctgggccc    40380
ggccgccgcg ccggtggact cggtggcggg cgtgctggcc gagctggacc ggctggaggc    40440
ggccatcccg gcgctgccgt cggccgagat cggccggtcc cggctggagc tgcggctgcg    40500
gcggttgagc gcccgcgtcg gcgagctggt cgccgcgaac ggcgagcggg cgaacggcgg    40560
gcgcgcgaac ggcgggcgcg cggcggccga cgagctggac gacgcggggg ccgaggacgt    40620
gctcgcgttc atcgaccggg agttcgggga cgcgtgagcg gccacacgag ccccgacccc    40680
ggcccccacc gcgcccccca caacgacgac cctggcgagg aacagatggc gaacgacgag    40740
aggctcctca gctacctcaa gcgggtcacc gccgacctgc accgcacgcg ggagcggctg    40800
cgcgaggcga gtccggggc ggacgagccg atcgcgatcg tcggcatggc ctgccgcttc    40860
cccggcggcg tgcgcacccc ggacgagctg tgggagctgg tggcgtccgg ccgcgacggc    40920
atcggcccgt tcccggacga ccggggctgg gacctgggcg cgctgttcga cccgaccccc    40980
gacgccaccg gccgctccta cgtcaccgag ggcgggttcc tggacgacgc ggccctgttc    41040
gacgcgggct tcttcgggat ctccccgcgc gaggcgctgg ccaccgaccc gcagcagcgg    41100
gtgctgctgg agaccgcgtg ggagaccttc gagcaggcgg gcatcgaccc gacctcgctg    41160
tccgggcagg acgtgggcgt gttcaccggg gtcgccaacg gggactacgc gctgaccgtg    41220
gaccgggtgc cggagggctt cgagggctac ctgggcatcg gcgggcggg cagcatcgcc    41280
tccgggcgca tctcgtactc cctgggtctg gagggtccgg ccgtcacgct ggacaccggc    41340
tgctcgtcgt cgctggtcgc gatgcactgg gccgggcacg cgctgcgggc gcgggagtgc    41400
tcgctggcgc tcgcgggcgg cgtgatggtg atggcgacgc cgggtgggtt cgtcgggttc    41460
tcccggcagc gcgggctggc ccgcgacggg cggtgcaagt cgttcggcga cggcgcggac    41520
ggcacgtcgt ggtcggaggg cgtgggtctg ctgctgctgg agcggctgtc ggacgcgcgg    41580
gccaacgggc acgaggtgct tgcggtggtg cgcgggtcgg cgatcaacca ggacggggcg    41640
tccaacgggc tcaccgcgcc caacgggccg tcgcagcagc gggtgatccg cgcggcgctc    41700
gacgcggcgg ggctcgggca cgcggacgtc gacgcggtgg aggcgcacgg caccgccacg    41760
gtgctcggcg acccgatcga ggcgcaggcg ctgctgaaca cctacgggcg gcaccgggac    41820
ggggcgcagc cgctctacct ggggtcggtc aagtccaacc tcgggcacac ccaggcgcg    41880
gcgggcgtgg ccggggtgat caaggcggtg caggcgatgc ccacggcgt gctgccgccc    41940
accctcaacg tcggcacgcc caccaccaag gtcgactggt cctcgggcgc ggtggaggtg    42000
ctggcggagg cccggccgtg gccggagacc gggcgtccgc gccgggtggg cgtgtcgtcg    42060
ttcggcgtga gcggcaccaa cgcgcacgtg atcctggagc aggcacccga gcacgagcca    42120
gcgccggagg agccgggtgg gcgcgggccg gtggcggcgg gcggcgcgac gccgtggacg    42180
ctgtccgggc gcacgcccgc cgcgctcgcc gaccaggcgc ggcggctggc cgggcacgtg    42240
acggccgacc tgcgggcgga ggacgtcggg ttctcgctgg ccaccaccag ggcgcacctg    42300
gagcaccggg cggtggtggt cggctcggac gggctggcgg cgctggccga aggccgctcg    42360
tccgcgctcg tgacgaccgg tgaggccggg gtcgacgggc gcgtggtgtt cgtgttcccc    42420
ggccaagggg cgcagtggat cggcatgggc gcggagctga tcgacgcgtc gccggtattc    42480
gccgagcggt tgcgcgagtg cgcggaggcg ctggaaccgt tcgtggactt cgacctgatc    42540
```

```
gaggtgctgc gcggacgcgg gtcgctggag cgggtcgacg tggtgcagcc cgcgtcgtgg    42600
gcggtgatgg tgtcgctggc agcgctctgg cggtcgctgg gcgtggaacc ggacgccgtt    42660
gtcgggcact cgcagggcga gatcgcggcg gcggcggtca gcggggcgct cagcctgccc    42720
gacgccgcag ccgtggtcgc gttgcgcagc aaggcgatcg cccaggacct ggccgggctc    42780
ggcggcatga tgtccgtcgc cctgcccgcc gacgacgtcg acctgagcgg gtatcccgga    42840
cgcctgtggg tcgccgcgca caacggcccc acctcgaccg tggtgccgg tgacgtggac    42900 gcgctgcgcg agctccacgc ccactacgag ggcgccgagg tccgggcccg gatcatcccc    42960
gtcgactacg ccagccacac cgggcacgtc gacaccatcc gcgagcggct cgccgaggca    43020
ctggcgcacg tgcggccgag ggcgggcacg atcccgtggc tgtcgaccgc gaccggcgag    43080
tggaccaccg gtgaggacgc cgacgccgac tactggttcc gcaacctgcg cggcgcggtg    43140
ggcttccaca ccgccatcac caccctcgcc gagcagggcc accgggtgtt cgtggaagtc    43200
tccagccacc ccgtgctcac caccgccatc gaggccacgc tcgaaggaac cggacccacc    43260
gccgtcaccg gaaccctccg ccgcgacgac ggcggccccg accgcctcct caccagcctc    43320
gccaccctgc acgtgcgcgg cgtccacgtc gactggaagg ccgtgttcgc cggcacgggc    43380
gcgcgccgcg tcccgctgcc gacctacgcg ttccagcacg agcgctactg gctggaccgg    43440
ggcgcggcgg ccggtgacgt cacggggcgc ggcctggccg acgcggcgca cccgctgctg    43500
gccgccgtcg cccagctgcc cggcaccggc ggggtgctgc tgagcgggcg gttgtcgcgg    43560
gcgacgcacc cgtggctggc cgagcacgtg gtgaacggga ccgcgctggt gcccggcacg    43620
gccctggtgg agctggcgct gcgcgcgggc gacgaggtgg acgcgcccgt gctgcgcgag    43680
ctggtgatca cccggccgat gccggtgccg gagcgggtt tcctgcacgt gcaggtggac    43740
gtcgcgggtg cggcggacga cgggtcgcgg gcggtgcgga tctggtcgcg cgccgaggac    43800
gcggcgagcg agacgcccg ctggaccgag cacgccaccg gctccctcgc ccccgacgac    43860 gcggcccgc ccgcccgcgc gagcggcgcg tggccgcccg agggcgcggc ggccgtggac    43920
gtggacgact tctacgaccg cctcgcgggc gcgggctacg agtacgggcc gctgttccag    43980
ggcctcaccg ccgcgtgggc cggggacggg caggcgtggg ccgaggtggt gctgcccggt    44040
gaggcgggcg ggttcggcgc gcacccggcg ctgctggacg cggcgctgca cgtgggcacg    44100
ttctgcctgc ccgcgggcc ggggtcgcgc acgctgctgc cgttcgcgtg acgggcgtg    44160 cggctgcacg ccaccggcgc gacggcggtg cgggtgcacg cccgcgccac cggcgacgac    44220
ggcctcgtcg tggagctgcg cgacgcggac ggggaaccgg tcgtgacggt cgacgcgctc    44280
gtgctgcgcg acgccgaccc cgccgacgcg caggccccgg acgtcacggc ggacgcgttg    44340
tggcgggtgc ggtgggtcga gcagccgccc gcgcccgcgg cgcccggctg ggtgctgctg    44400
ggcgggccgt ccgggcacgc cgggttcgcc gccctgccgg tgttcgccga ccctgcggcc    44460
gtggcggcgc tgcccgaggg cgaccggccc gcggtggtcg tcgtggacac caccgcgtgt    44520
cgggagccgg ggcgggacgt gccggggggcg gcgcgggcgt tcgtggtgcg ggcgctggag    44580
ctgctggtgg cgtggctgcg cgaggacgcg ctggccggga cccgactggt gctagtcacc    44640
agcggcgcgg tgccggtgcg cgcggacgcc gaggtcaccg accccgctgc cgcggcggtg    44700
tggggtctgc cgcgctcggc gcagtcggag caccccgacc gggtgtggct gctggacgtc    44760
gacgagccgg gcgcggcgcc gggcgcgctg gcctcgccgg agccgcagct ggccgtccgg    44820
gcgggcgcgg ggttcgcgcc ccggctcgcc agggccgagg ccgcgcccgg cgcgctgccg    44880
gtcgacgggc cggtgctggt caccggcggc accggcacgc tcggcgcgct cgtggcccgg    44940
```

-continued

```
cacctggtca ccgcgcacgg cgcgcggaac ctgcacctgg tgagcaggcg cggcccggac   45000
gcgtccggcg ctcgagaact cctggacgag ctgcgcgggc tgggtgccga ggtcgagctg   45060
tcggcgtgcg acgtggccga ccgggtggcg ctcgccgccc tgctggggcg cgtgcgcccc   45120
gccgccgtgg tgcacgcggc gggcgcggtg gacgacggcc tgctcaccga cctgaccgcc   45180
gaccggttcg acgccgtgct gcggcccaag gtcgacgcgg tcgcccacct ggacgaccta   45240
ctcggggacg tgccgctggt ggtgttctcc tccgcgaccg gcaccctcgg caccccggc    45300
caggcgaact acgccgcggc caacgcggtc gccgacgcgc tcgtgcagcg ccgccgcgcg   45360
cggggcctgc cgggcgtgtc gctggcgtgg ggcctgtggt cggacaccag cgagctgacc   45420
gcgaccatgg acgccgccga cgtggcccgc acccgccggg gcggggtgct cggcctggac   45480
gcggcgcgcg gcctggcgct gctcgacgcc gcgctcggcg cggacgacgc gctgctcgtg   45540
ccgatccacc tggacaccgc cgcgctgcgc cggggggccg accggctcc gccgctgctg    45600
cgcggcctgt tccgccgcgc ccggcgcgcg cgggcgcggg cccggcaggc cgcgctgccg   45660
ctggtggcgc gactggccgg ggtggacgcg gcggagcggc ggcgggcgct ggtggagctg   45720
gtgcgcgccg aggccgccgc cgtcctcggg cacggcggcc cggacggcat cgggcaggac   45780
cagccgttcc gggaggtcgg gttcgactcg ctcacggccg tggagctgcg caaccggctc   45840
ggcgcggcca cgggtctcgc gctgcccgcg acggtggtgt tcgaccaccc gacgtccgcg   45900
cgggtcgccg agcacctgcg ggagctgctg ttcggcgcgg agacggctca ggcccccgcg   45960
cggcgggagg tggtggccga cgacgacccg atcgccgtgg tgggcatggc ctgccggttc   46020
cccggcgggg tcgccgacgc ggacgggctg tggcggctgg tcgccgagga gcgcgacggc   46080
atcggcccgt tcccggacga ccggggctgg gacctggcgg cgctgttcga cccggacccc   46140
gaccacgcgg gcacctcgta cgtgcgggaa ggcgggttcc tcgacggggc gacccgggttc   46200
gacgcgccgt tcttcggcat ctccccgcgc gaggcgctgg ccatggaccc gcagcagcgg   46260
ctgctgctgg aggtggcgtg ggagacgttc gagcaggcgg gcatcaaccc gcgctcggcg   46320
cacggcaccg acaccggggt gttcgcgggc gtgatctacc acgactacgg cgaggcggcg   46380
ggcgagctgc ccgagggcgc ggagacctac cgcagcaccg gcacgtcggg cagcgtggtg   46440
tccggccgcg tcgcctacgc gctgggcctg accggcccgg cgctgaccat cgacacggcc   46500
tgctcgtcgt cgctggtggc gatccacctg ggcgcgcggg cgctgcgggc gggcgagtgc   46560
tcgatggcgc tggtcggcgg ggtgacggtg atgtcgacgc cgggcgggtt cgtgagcttc   46620
tcgcggcagc gcgggctggc cccggacggg cggtgcaagt cgttctcgga gggcgcggac   46680
ggcaccgggt tcagcgaggg cgtcgggctg gtgctgctgg agcggctgtc ggacgcgcgg   46740
gccaacgggc acgaggtgct gcggtggtg cgcgggtcgg cggtgaacca ggacggggcg    46800
tccaacgggc tcaccgcgcc caacgggccg tcgcagcagc gggtgatccg cgcggcgctc   46860
gacgcggcgg ggttggggca cgcggacgtg acgcgcgtgg aggcgcacgg cacgggcacc   46920
accctcggtg acccgatcga ggcgcaggcc gtgctcgcca cctacgggca ggaccgcgag   46980
cagccgctgt ggctgggcac gctcaagtcc aacctcgggc acacccaggc ggcggcgggc   47040
atcggcagcg tgatcaagat gatccaggcg atgcggcacg gcgtgctgcc gcgcacccctg   47100
cacgtcaccg agccgaccac ggccgtggac tgggcgcggg gcgcggtgga gctgctgacg   47160
cgggcgcggg agtggccgga gaccgggcgt ccgcgccggg cggggtgtc gtcgttcggg   47220
gtgagcggca cgaacgcgca cgtgatcctg gagcaggccc ccgaaccggt ggcggtggag   47280
gcggcgccgg aggcgggggt gctgccgtgg gtgctgtcgg cccgcacgcc cgaggcgctg   47340
```

```
cgggagcagg ccgaccggct cgtggcgcac ctgggcggtg agtcgtcctc ggcggccgtg   47400
gcccggtcgc tggtgctggg tcgggcggcc ctggaggagc gggccgtggt cgtgggcgac   47460
cgggcgcgcg ccggggaggc gttgcgggcg ctggccgagg ggcggccctc ccccgcgctc   47520
gtcaccgggc ggaccggggt cgaggggcgc gtggtgttcg tgttcccggg tcagggcgcg   47580
cagtgggtcg gcatggggcg tgcgctgctg gacgcctcgc cggtgttcgc cgaacgcctg   47640
cgcgagtgcg cggcggccct gcgcccgtac accgactggg acctggtcga ggtgatcacc   47700
tcgggtggcg cgctggacga cgtggacgtc gtgcagcccg cgtcgtgggc ggtgatggtg   47760
tccctcgcgg cgctgtggcg ctcgctcggc gtcgaaccgg acgcggtgat cgggcactcg   47820
cagggcgaga tcgccgccgc gaccgtcgcg ggctggctca gcctccagga cggcgcgaag   47880
atcgtcgcgc tgcgcagcca gctgatcgac gaggagctga ccgggctggg cggcatgatg   47940
tccgtcgccc tgcccgccga ggacatcgac ctgagcggtt acgagggccg gttgtgggtc   48000
gcgacggtca acgggccgag cgcgaccgtg gtcgccgggg acaccggggc actggaggag   48060
ctgcggcgcg gctgcggcga ggcggtccgc acgcgggtga tccccgtgga ctacgccagc   48120
cacaccgggc acgtcgacgc catccgcgac cagctcgccc ggatgctcgc cgacgtcacc   48180
ccgcggcccg gcgagatccc gtggctgtcc acggtgaccg gcgagtggat cacccccggc   48240
gacgacgacg ccgactactg gttccacaac ctccgccgca ccgtccactt cgccgacggg   48300
atcaccaccc tgctcgacgc cgggcaccgg gtgttcgtgg aggtctcctc gcaccccgtg   48360
ctggcggcgg cggtgcagga gagcgccgag gcggccgggg acgcgcgggt cgccgtgacc   48420
ggcacgctgc gccgcgacga cggcggctgg gacgggtcc tgaccggcct ggccgagctg   48480
cacgtgcgcg cgtggacgt ggactggacg cgggtgctgc ccgaggcggg gcgggcgccg   48540
ctgccgacgt acgcgttcca gcacgagcgc tactggccgg aacccgcgcg cccggccgcc   48600
gcgccgggcg gtggtgacga cgcgctgtgg gcggtgatcg agggtggtga cgcggcggac   48660
ctggccgggg agctggccgt ggacgaggac gagctggcgc gggtgctgcc cgccctgacc   48720
tcctggcggc ggcgcagccg ggcaaggagc gcgctcgacg gctggcgcta ccgggtcgac   48780
tgggtcccgg tccccacgag cgggtctggg ctgcccggcg gcaagcgct gtccggcggg   48840 caggcgctgt ccggcgggcc gaggtcgtcc ggcggggcag ggctctccgg cggtcagggg   48900
acgccaggcg ggtccgggtc gcccggcgga gcggcactgc caggcgggcc agggtcgccc   48960
ggcggagcgg cgctgcccgg ccgggtggcc gtggtggtgc ccgcgaacga cgagcgggcg   49020
cgggcggtcg cgggcgggct ggtcgcgcgg ggtgtggacg tgaccgtcgt ggcggcgtc   49080 gacgccaccc gcgacgggct ggcgaaggcg ctgcccgacc gccccgacgc cgtggtgtcg   49140
ctgctgtcct gggacgcggg ggccgacgag ccggcgcgc ccggttcggc cacggccgcg   49200
ctggtgcagg ccctggccga ccgggtgcc accgggccgc tgtggtgcgc gaccgggggc   49260
gcggtgagcg tcgcgggcga ggacgccgac cccgaccagg ccgccgtgtg ggggttgggc   49320
ggggtgctgg ccctggacct gccggaggcg ttcggcggac tggtcgacct gccgcggcag   49380
cccaccgacg ccgacctcga cgcgttcgcc gccgcgctga ccgcccccgg cggcgaggac   49440
cagctcgcgg tgcgcgacgg ccgcctgctg gcccgccgcc tggtccgcga cggggccgac   49500
gcgccggagt ggacgccgcg cggcgcggtg ctggtcaccg gcggcaccgg cggcctcggc   49560
acgcacgtgg cccgctggct cgcccgctcc ggggccgggc acgtcgtgct cgccagccgc   49620 tccgccccg ccgccccgg cgcggccggg ctggccgccg aggtggaggc gctggcgcg   49680 cggtgcagcg tggtggccct ggacgtggcc gaccgggacg cggtggccgc cgtgctcgcc   49740
```

-continued

```
gacgtcgagc gggacgggcc gctgaccgcc gtggtgcacg cggcgggcgc gggactggcc   49800
ccgacgccgc tggtggagct gaccgccggg cggtacgcgg acgtcgcggc cggcaaggtc   49860
gagggcgcgc gggtgctgga cgaggtgctc gccgaccggg cgctggacgc gttcgtgctg   49920
ttctcctccg gcgcggccgt gtggggcagc ggcgggcagg ccccgtacgc ggcggccaac   49980
gcgttcctgg acgggctggc cgcccgcagg cgggcgcgcg ggctcgtggc cacctcggtg   50040
gcgtggggcg gctggggcgg cggcctcggc atgatcggcg acggggacgc ggagcggtgg   50100
gcccggctgg gcatccgcac gatggacccg gaggcggcgc tgcgcggcat ggcgctggcg   50160
gtcggctccg ggcgggccgc gagcgtggtg gccgacgtcg actgggcccg gttcgccccc   50220
ggctacgccc tggcgcggga gcgcccgctg ctgcgcgggc tgccggaggt ggtggcgctg   50280
ctggccgaac cggacgagcc cgccgcgcg gtggacgcgc gggcgcgct ggcggccgg   50340 ctgaccgggc tggacgcggc cgggcaggac gagctgctcg cggacctggt gcgggcgcag   50400 gcggcggcg tgctggggtt cgccgaccct ggcgcggtcg cggcggaccg ggcgttcaag   50460
gacgccgggt tcgactcggt gaccgccgtg gagctgcgga accggctggg cgcggccacc   50520
gggctgcggc tgccgccgac cgtggtgttc gaccacccga aaccctggc tctggcgcgc   50580 gtgctgcgcg ccgagctggt cccccagcgg ggggacgggg tgacggcggc gcaggtggcg   50640
caccgggagg acgcgatccg gcgggtgctg gcgtcggtgc cgctggcccg gttcgaggag   50700
ctgggcgtgc tcggcgcgct cgtggacctc gtgcccgccg cgccaccggc gggcggcgcg   50760
gcgacagcgg agcgggacga cctgcgcgac ctggcggagc tggacctgga cggtctggtc   50820
cgcagggcga tgcgcggcac caccgccggg aacgactgag gctttgatgc ggagcggaga   50880
gagcatgagc gcgggcacct cgccggagag cgtcgtccag gccctgcgga ccacgctggt   50940
ggacaacgag cggctgcggc gggagaacga gcggctggtc gccgaggccg gtgagccggt   51000
ggcgatcgtg tcgatggcgt gccggctgcc cggcggcgtc accgaccgg agtcgctgtg   51060 ggagctggtg cgcgagggcc gggacgccat cgggccgttc ccgaccgacc ggggctggga   51120
cctggggtcg ctgttcgacg acgacccgga cgcggcgggc tcctcgtacg tgcgggaggg   51180
cgggttcctg gcgcgggcgg gcgggttcga cgcgccgttc ttcggcatct ccccgcgcga   51240
ggccctggcc atggacccgc agcagcggct gctgctggag gtggcgtggg aggccgtgga   51300
gcgggccggg ctcgacccgc gctgctgga gggccgggac gtcgcggtgt cgcgggcgg   51360 caacccgcag ggctacggcg gcggaccggg tgacgccccg gagggcctgg aggggttcct   51420
gggcgtcaac gcctcgtcgt cggtgatctc cggcgcggtc tcctacaccc tgggcctgac   51480
cggcccggcc gtcaccgtgg acacggcgtg ctcgtcgtcg ctggtggcga tccacctggc   51540
ggtgcggtcg ctgcgctcgc gggagtgctc gatggcgctc gcgggcgggg tgaccgtgat   51600
ggggcagccg accgcgttcg tggagttctc gcggcagcgc gggctcgccc cggacgggcg   51660
gtgcaagtcg ttcggcgacg gcgcggacgg cacgtcgtgg gccgagggcg tcggcgtgct   51720
gctgctggag cggctctcgg acgcgcggcg cgacgggcac gaggtgctgg cggtgatccc   51780 cggctcggg gtgaaccagg acgggcgtc caatggcctg accgcgccga acggcccgtc   51840
ccaggagcgg gtgatcgcgg cggccctggc cgacgccggt ctcggcctgg ccgacgtgga   51900
cctgctggag gcgcacggca ccggcaccag gctgggcgac ccgatcgagg cgcggcgct   51960 gctcaacacc tacgccgggg gcaggccgca ggaccggccg ctgtggctgg ggtcggtgaa   52020
gtcgaacctc gggcacgccc agtcggcgtc ggggtggcg ggcgtgatca aggtggtgca   52080
ggcgatccgg cacggcctga tgccgcgcac gctgcacgcc gacgagccga gctcgaacgt   52140
```

```
ggactgggcg gcggggcgg tggagctgct ggcgcgcgag cgggagtggc cggagaccgg   52200
gcgggcgcgg cggggcgcgg tgtcgtcgtt cggggtgagc ggcacgaacg cgcacgtgat   52260
cgtggagcag gcgcccgagg aggccgccgc cgggtcgcg gcggcggggc ggcccgcgcc   52320
caggtcggcg ggcgggcagg acgccgggat cgcggcggtg accgggcagg ccgccccgc    52380
cgctggcccc gccaccgccg aacccgccgc gtcggccgtc gaggacggga ccggcgtcgc   52440
ccccggcccg gtcgcgaccg gcggggtcgt gccgtgggcg ctgtccgggc ggaccgccgc   52500
cgcgctggcc gcccaggcgg cccggttgcg cgcgcacctc gccgcgcacc cggcggcccg   52560
cccgtggac gtggcctggt cgctggccac gacccgctcg gtgctggagc accgggccgt    52620
cgtgcccgcc gcctcgctcg acgaggccct ggcggggttg gacgcgctcg cctcgggccg   52680
cgcggaccgg tcggtggtcg tcggcgaggc ggcgcccggc cgggtggcgg tgctgttcac   52740
cgggcagggc agtcagcggg ccggtgcggg gcgcgagctg cgggagcggt tcccggtgtt   52800
cgcgcggggc ttcgacgccg cgtgcgccgc cgtgggcgag ctgcccaccg gcgacgcgcg   52860
cgcgatcggg ctcgccgagg tggcgctggc cgaccccggc acgcccgccg ccgcgctgct   52920
cgaccggacc gcgttcaccc agcccgccct gttcgcgctg gaggtcgcgc tgttccggct   52980
ggtccagtcg tggggcgtgc gcccggcggc gctggccggg cactcggtcg gcgagatcgc   53040
cgccgcgcac gtggccgggg tgctctccct cgccgacgcc gccgcgctgg tgcgcgccag   53100
gggcgggctg atgcaggagc tgcccgaggg cggcgcgatg gtggcggtgg aggcggccga   53160
ggacgaggtc gtgccgctgc tcggggacgg ggtgtcgctg gccgccgtca acggccgac    53220
ctcggtggtg ctctccggcg acgaggaggc cgtcaccgcc gtcgccgcga ggctggcgca   53280
gcggggcagg cgcaccaaga ggctcgccgt ctcgcacgcc ttccactcgc accgcgtgga   53340
cccggcgctg ccgccttcc gcgccgtggc cgaggagctc gcctacgccg cccccacgat    53400
cccgatcgtc tccaccctca ccggccgccc cgtcacccc gacgagctgc gctccccga    53460
ctactgggtg cggcacgcgc gcggcgccgt ccggttcctg gacgccgtgc gggcgctggg   53520
ggacgcgggc gcgcgcacgt tcctggagct gggcccggag ggcgtgctca cggcggcggg   53580
cgcggactgc ctgccggacg cggtgttcgc ggcgacgctc cgccgcgacg tgcccgaggc   53640
gcgggccgtg ctcgccgggg tcgcgggcct gcacgtgcgc ggcgcgacag tcgactgggg   53700
ttcgctgttc acgggcgcgg acgcgcgcg cgtcccgctg cccacctacg cgttccagca    53760
cgaggaccac tggctggtgc gccgctccac cgccgccgac gtgggcgcgg tcggcctgcg   53820
cgaggccggg cacccgctgc tgggcgcggt cgtcgcgctg ccgagagcg gcggggtgca    53880
gctgagcggt cggttgtcgg tggcggcgca gccgtggctg gccgagcacg tcgtctccgg   53940
cacgcgctg tgtccgggcg cggcgctggt ggagctggcg gtgcgggcgg gcgacgagac    54000
cggcacgccc gtgctggagg agctggtgat cggccgcccg atgccgctgc cggacggcgg   54060
cgcgctgagc gtgcaggtcg tcgtcggccc ggacgagggc gggcgccggt cggtgcgcgt   54120
gtactcccgc gcggacgggg cggtggactg ggtcgagcac gcggcggggg cgctgaccgc   54180
gccggaggcc gcgccgaccg ccgacgcggg cccgtgccg ccgagaacg ccgaacccgt     54240
ggacacgcgg ggcttctacg acaccctcgc ggagggcggc tacgcctacg cccgctgtt    54300
ccggggcctg acctcggcgt ggcgcggcga gggcgaggcg tgggcggagg tggcgctgcc   54360
cggtgacgcg accgggttcg gcatccaccc ggccctgctc gacgccgcgc tgcacaccgc   54420
gcacttctgc ctgcccaccg ggaccgagcg gcgggccggg ctgctgccgt tcgcctggac   54480
cggcgtgcgg ctgcacgcgg gcggcgcgac gaccgcgcgg gtgcacgccc gcgccaccgg   54540
```

```
cgacgacggc gtgaccgtgc gcctgctcga cggtgccggt cagccggtcg cggacgtggc    54600
cgccctgacc ttccgcgccg cagccgacac cccgtccgcc gaggtccngg acgcgctgtg    54660
ggcggtggag tggaccgagc acccgctgcc cgcggacggg accaccccg cgggcgggac     54720 caccacggcc gtggtggtcg tggacacccg gagcgtcgac gccccgacg acggcccgc      54780 ccgcgcccgc gcgctgaccg cccacgtcct cgccgagctg cagcggcacg ccgacgacga    54840
ccggccggtc gtcgtggtca cctcaggcgc ggtcgccgtg cgcgtcgacg gcgaggtcac    54900
cgaccccgcg tccaccgccg tgtggggct ggtgcgggcc gcgcaggtcg agcagcccga     54960
ccgggtccgg ctggtcgacg tcgagccggg ggccgacccg gtgctcacct cgcccgagcc    55020
gcaggtggcg ctgcgcggcg ggaccgcgca cgtgcccagg ctggtccgcg cccgccgcgc    55080
cctcccggcg ccgaccgcga cgtcgtggcg gctgggctcc gaccgccccg gcacgctgga    55140
ctccctcgcc ctgctcccgg acgactccgg cacggcccg ctcgccccg gcgaggtgcg      55200 gatcgcggtc cgcgcggcgg gcctgaactt ccgcgacgtg ctggtcgcgc tgggatgta    55260 ccccggtcgc gcggtgatcg gcgcggaggg cgcgggtgtg gtcgtggagg tcggccccgg    55320
ccccgacgac accgacgccg gcgacaccgg ccccggcgac accggctcgg gcggcctggc    55380
cgtgggcgac cgggtgatgg gcctgttccc cggcgcgttc ggcccgctgg ccgtggccga    55440
ccaccgaatg gtgaccccgga tgccggacgg ctggtcgttc accaccggcg ccggcgtgcc    55500
catcgcgttc ctgaccgccc tctacgggct gcgcgacctc ggcgggctca ccgcgggcga    55560
gaccgtgctg gtgcacgcgg cggcgggcgg ggtcggcatg gccgccgtgc agctcgcgcg    55620
ggcgttcggc gctcgggtgc tgggcaccgc gcacccggcc aagcacgcgg ccgtgacccg    55680
cctgggcgtc cccgagtccc acctgtcctc cagccgcgac accgcctacg ccgacctgtt    55740
cggcccggtg gacgtggtgc tgaactcgct caccggcgag cacgtggacg cctcgctggg    55800
gctgctgcgc gcgggcggcc ggttcctgga gatgggcaag accgacctgc gcgacgccga    55860
cgaggtcgcg aaggcgcacc ccggcgtcgc ctaccgcccg ttcgacctgg gcggcgaggc    55920
gcccgccgag cgcgtcgcgg agctgctggc cgagctggtc gcgctgttcg aggcgggccg    55980
catccacccg ctgcccaccg cggcctggga gatcacccgc gcgccggagg cgttcggctg    56040
gatgagccgg gccgggcacg tgggcaagat cgtgctgacc ctcccccgcc gccccgaccc    56100
ggacggcacg gtgctggtca ccggcggcac cggctcgctc ggcgcggtcg cggcccggca    56160
cctggtcacc gcgcacggag cccgccacct gctgctcgcc tcccgacgcg gcgagcaggc    56220
ccccggcgcg gcggagctga ccgacgggct gcgcggctg ggcgcggacg tgcgggtcgc     56280
ggcgtgcgac gtcgccgacc gggacgcgct cgccgcgctg ctcgccacga tccccgccgc    56340
gcacccgctc accgccgtcg tgcacacggc gggcgtgctc gacgacgcg tgctcgccgc     56400 gcagaccccc gagcgcctgg acgcggtgtt ccgccccaag gtcgacgccg tcgcgaacct    56460
gcacgagctg accggcgacc cggccctgtt cgcgtgtac tcctcggcct ccggcgtgct     56520
cggcggcgcg ggccagacca actacgccgc cgcgaacgcc tggctcgacg gcctcgccca    56580
cgtccggcgc gcggcgggcc tgcccgcgac ctcgctggcc tggggcctgt gggcgcagga    56640
cggcggcatg acgggcggcc tggcgggcgg accggccggg ccggcgggc gggcccgccg     56700 gggagccgtc gcgccgctgt ccaccaccga gggcatggcg ctgttcgacg cggccgtcgc    56760
gtcgggccgc ccgctcctgg ccccgatcag gctcgacccc gccgcgctca ccgccgacgg    56820
cgcgcagccg cccgcgctgc tgcgcggcct ggcccgcccc accgccgca ccgccgtcgc     56880 ggccaccacc gacgacggcc tcgcgggcag gctcgccgcg ctcgacggcc ccggcaggca    56940
```

```
gcggctgctc gtggagctgg tgcgggagca ggccgccgcc gtgctgggct cgcgacccc    57000 ggacgccgtg tcgccgggcc gggcgttccg ggacctgggc ttcgactcgc tgacggccgt    57060
ggagctgcgc aaccgcctct ccgccgccac cggcctgcca ctgcccgcca ccaccgtgtt    57120
cgaccacccg accccgctgg acgcggcggc ccacctgctc gacgcgctgg gcgtcgcccc    57180
cgcgcccgcc ccggccaccc cggtcgtgac ggccgcgcgg gacgacgacc cgatcgcggt    57240
cgtcgccatg ggctgccgcc tgcccggcgg cgtgtcctcc ccggaggacc tgtggcggct    57300
gctcgacggc ggcgtcgacg ccatcggccc gttcccggac gaccggggct gggacctggg    57360
gtcgctgttc gacgacgacc ccgacgcggt cggcaagtcc tacgtgcgcg agggcgggtt    57420
cctggcgggc gcgggcgggt tcgacgccgc gttcttcggc atctcccccc gcgaggcgct    57480
cgccatggac ccgcagcagc ggctgctgct ggaggtggcc tggagaccg tcagcgggc    57540 cgggatcgac ccgacctcgt tgcgcggcgc ggacgtcggc gtgttcgccg ggcgggcgc    57600 gcagaactac ggcagcggcc ccggcccggt gcccgagggc ctggagggct acctgggcgt    57660
gggcggcgcg acgagcgtgg tgtccggccg cgtctcctac acgctcggcc tcaccgggcc    57720
cgcgctgacg atcgacaccg cgtgctcctc gtcgctggtg gcgatccacc tggcggtgcg    57780
gtcgctgcgc tcgggcgagt gctcgatggc cctggcgggt ggggtcgcgg tgatgggcga    57840 gcccgcggc ttcgtggagt tctcccggca gcgcgggctc gccccggacg gcggtgcaa    57900 gtcgttcggc gcggaggcgg acggcacgac gtgggccgag ggcgcgggac tggtgctgct    57960
ggagcggttg tcggtggcgc gggcgcgcgg gcacgaggtg ctggcggtgc tgcgcgggtc    58020
ggcggtcaac caggacgggg cgtccaacgg cctgaccgcg ccgaacggcc cgtcgcagga    58080
gcgggtgatc cgggcggccc tggccgacgc ggggatcacc ccggacgcgg tggacgcggt    58140
ggaggcgcac ggcaccggca ccaccctcgg tgacccgatc gaggcgcagg ccgtgctggc    58200
gacctacggg caggaccgcg agcagccgct gtggctgggg tcgctgaagt cgaacatcgg    58260
gcacgcgcag gcggcggcgg cgtcgcgag cgtgatcaag tccgtgctgg cgctgggccg    58320
gggcgtgctg ccccgctccc tgcacgccag caccccgacc ccgcaggtcg actggtcctc    58380 ggggcggtg gagctgctgg cgcgggcgcg ggagtggccg gagaccgggc gtccgcgccg    58440
gatcggggtg tcctcgttcg gggtgagcgg caccaacgcg cacgtggtcc tggagcaggc    58500
ccccgagccg gaaccgcgc gggaggcgga accgcgcgg gagtccgcgc cagggccgga    58560
gtccgttccg ccgctgaccg gggccacgcc gtggctgctg tccgcccgct ccccgaggc    58620 gctggcggac caggccgccc ggctggtgga cgccgtgccc gccgagtggc gggcctccga    58680
cgtgggctgg tcgctggcca ccacgcgggc ccgctggag cagcgggccg tggtcgtggc    58740
gcgggacacc gcgcgcgggc tcgccgccgc gtccgcgctg gccgccggac gcccgaccc    58800 gcacgtggtc accgggaccg ccgacgtgga cggcaggacc gccttcgtct tccccggcca    58860
gggcgcgcag tgggcgggca tgggcggga actcctggac gcctcgccgg tgttcgccga    58920
acgcctgcgc gagtgcgcgg cggccctgcg cccgtacacc gactgggacc tggtcgaggt    58980
gatcacctcg ggtggcgcgc tggaggacgt ggacgtcgtg cagcccacca gctgggcgat    59040
catggtgtcg ctggccgcgc tgtggcgctc gctcggcgtc caccggacg cggtgatcgg    59100 gcactcgcag ggcgagatcg ccgccgcac cgtcgcgggc tggctcagcc tccaggacgg    59160
cgcgaagatc gtcgcgctgc gcagccagct gatcgacgag cacctgaccg gctcggcgg    59220 catgatgtcc gtcgccctgc ccgccgagga catcgacctg accggctacc agggccggtt    59280
gtgggtggcc gcccacaacg gccccaccgc gaccgtggtc gccggggacg ccgacgccct    59340
```

```
ggcggagctg cgggacgcgc tggagggcga ggcccgcacc cgcgtgatcc ccgtcgacta   59400
cgccagccac accggccacg tcgacgccat ccgcgaccag ctcgcccgga tgctcgccga   59460
cgtcaccccg cggcccggcg agatcccgtg gctgtccacg gtgaccggcg agtggatcac   59520
ccccggcgac gacgacgccg actactggtt ccacaacctc cgccgcaccg tccacttcgc   59580
cgacgggatc accaccctgc tcgacgccgg gcaccgggcc ttcgtcgagg tctccacgca   59640
ccccgtgctc accccggccg tgcaggaggc cgccgaggcg aacccggcgc tgcgcaccgt   59700
cgccgtgggc accctgcgcc gcgcggacgg cggcgcggag cgggtggtgg cgggcctggc   59760
cgagctgctg gcgcgcgggg tggccgtgga cccggcgggg tgttccccg gtgcgaggcg   59820 ggtcgcgctg ccgacgttcg cgttccggca cgagacgttc tggctctcgc gggcgctgcc   59880
cgacgcgcgg ccggtgccgc agggcgggca cccgctggcc ccggtggtgg tgagcgatcc   59940
gggcacgggc ggggtgatcc tgtccggccg gatctccgcg gccacccacc cgtggctgct   60000
cgaccacgcc gtcgcgggcg cggtgctgct gcccggcgcg gcgctggccg agctggcggt   60060
gcgggccggc gacgagaccg ggacgcccac cctggaggag ctggtgatcg gcaggccggt   60120
ggtgctgccc gaggacgggg agctgcggct ccaggtggtc gtgggcgccg aggacggggc   60180
gcgccgcgag gtgcgcgcct actcccgcgc cgacgacgcc gcgccgtgga ccgagcacgc   60240
gagcggcacg ctgtcggcga agtcctcgct gcccgccgac gtcccggccg ccccgtggcc   60300
gcccgcgggc gcggagccga tcgcgctgga cgggttctac gaggccatgg caggggccgg   60360
ttacgggtac gggcccgcgt tccggggct gcgcgcggcc tggcgcgacg gggacgacgt   60420
ggtcgccgag gtggccgtgc cgcggggcgca ggagcaggtg gcgggccggt tcggcatcca   60480
cccggcgctg ctggacgccg ccctgcacgc cgggaacttc tgcttccccg cgcaggacgg   60540
cgagcgggcc acgatgctgc cgttcagctg ggacgacgtg cggttgcacg ccaccggcgc   60600
gacgtcggtg cgggtgcggg cccgcgcggt gggcggccct ggcgcgcccg cgctgaccgt   60660
ggcgatcacc gacccgagcg gggtgccggt ggccggggtg ggcgcgctcg ggatgcgcgc   60720
ggtcagcccc gagcagctgg gcgcgccggg cgtcggcggt gacgcgctgc gggtgctgga   60780
gtgggccgag gtggccggtcg aggcggcgga ccggtgggcc gtgctgggct ccagcggca   60840 cccggacgtg gacgcctacg cggccgaccc ggaccggccg ggggcgctgc tggtggacgt   60900
gggcgcctgg ctgggcggcg acgacgccgt ggcccgcgcg cacgcgctga ccagcgcggc   60960
gctggagctg gtgcgggact gggcgacccg cggggacctg gcggtgagc ggctggtgct   61020 ggtcacgacc ggggccgagg acgtgcgcga caccgcgccc cgcgaccgg cgcaggccgc   61080 cgtgtggggc ctggcgcgct cggcccgctc ggagcacccg gaccggttcg cgctggtcga   61140
cgccgacgac cggtccccgg cgacgctcgc cctggcggcc gggtcggcgt tcccggaggt   61200
ggtcctgcgc ggcgagcggg cgcacgcgcc gaggctggcg cgggccgtcc ccggcaggcc   61260
ggtggcgctg gacccggacg gcacggccct gatcaccggc ggcaccggcg ccctgggcgc   61320
gctcgccgcc cggcacctgg tgaccgcgca cggcgtgcgg cgcctgctgc tcaccggccg   61380 ccggggggccg gacgccccccg cgcggcgga gctggccgag gagctgcgcg gctgggcgc   61440 ggacgtgcgg gtggaggcgt gcgacgtcgc cgaccgggac gcgctcgccg cgctgctcgc   61500 gtcgatccc gccgggcgcc cgctcaccgc cgtcgtgcac gcggcgggcg cgctcgacga   61560
cgccccggtg accgacctga ccccggagcg gctgtccgcc gtgctggccc cgaaggtcga   61620
cgcgctggcc aacctggacg agctggtcgg ggacgggccc gcggtgttcg cggtctactc   61680
ctcggcgtcc ggggtgctcg gcacggccgg gcaggcggcg tacgcggcgg ccaacacctt   61740
```

```
cgcggacgcg ctggtgcgcc gacgccgggc cgagggccgg gcgggcgtgt cgctggcgtg   61800
gggcctgtgg gcaggcgcca gcgagctgac cggcgacctg gccggtgacc ggctcgcccg   61860
cacccgccgg ggcgggctgg tgccgctgac cgccgccgag ggcatggcgc tgttcgacgc   61920
gggcgcggtc accacgggcg gcccggcgct ggtcgtgccg ctgccgctgg acctggcggc   61980
gctgcgcgcc tccgcgcgcg acgaggcggt gcccgcgctg ctgcgcgcgc tcgtccccgc   62040
cgcgcggcgc tcgctctccc ccgccaccgg gcaggccgcg cccccggccg ggttgcgggc   62100
gcgcctggcc gggctgtcgg gcgacgagca ggaggccgtg ctcaccgagc tggtccgcga   62160
cctggccgcc gccgtgctcg gcacggcgga aagggcgcg gtgggcccgg acgacgcgtt   62220
cttcgagatc ggcttcgact ccatgacggc cgtgcagctg cggaaccggc tgaacaccgc   62280
caccgggctg cgcctgcccg ccgcgctgct gttcgaccag ccgacgcccg cgatcgccgc   62340
cgaggcgctg cgcgagcgac tggccgccga gcaatcgggc tcagggcaat cgggcgcagg   62400
gcagccgggc gcagggcatt caggcgcagg gcagtcgagc gcagggcgat caggcgcagg   62460
gcagtccacc gacccgaccg acgagaggtg agcaccagca tgatcgacgt ggccgagtac   62520
ctgcggcgca tcggcgtgga gggcggcgtg ccgagcccga cgctggagtc gttgcgggcg   62580
ctgcacaagc ggcacctgat gtccgtgccc tacgacaacg gcggcgcggc cgaccggttg   62640
ccgccgaacc gggggctcgc ggagatcccg ctgccccgtg tgttcgcgca cgtggtgacc   62700
ggccgcaacg gcggggtctg ctacgagctc aaccggctct ccacgccct gctcaccgcg   62760 ctgggctacg aggtgctgat ggtcgcgcg cgatccggc tggccgacga ccggttcggg   62820
ccggacgagg agcactcgtt caacctggtg cgcctggacg ggcggacctg gctggtggac   62880
gtggggttcg tcggcccgtc ctacctggag ccgctggagc tgtcggcggt cgagcaggag   62940
cagtacggct gcgcctaccg ggtcgtggag cgcggggacg cgcacgtggt ggagcgcagg   63000
cccagggacg gggcgtggca ggcggtgtac cggttccggc cggggcgggc ggaccgggac   63060
ggctgggagg cggtgcggtt ggacgggctg gacgactacg cgcgggactc ggtgctggcg   63120
ggcaccacgt tccgggggtcg gcggcggag aacgggcagc acgtgctgat cggccgccgc   63180
tacttcaccg tgctggacgg ggtggagacg acgcgggtgc tcgtgaagaa ggacgagttc   63240
gcccgcgtca ccgagtcgat catgatcggg gggtgagcgc gtggcgggcg aggtcgagca   63300
cgacgtggtg gtcgtcggct acgggccggt ggggcagctg ctgtcggtgc tgctggcgca   63360
gcgcggctgg cgggtgctgg tgctggagcg ctggccgacg ccgttccggc tgccgcgcgc   63420
ggtcgggttc gacagcgagg cgacccgcgt gctggcctcg gccgggctcg ggcccgcgct   63480
ggccgagttc ggggagcccg cgggcgacta cgagtggcgc accgcgtccg gggagacgct   63540
gatcgcgttc accgtgcggg aggagggca ctgcggctgg cccgaggcga cctcggccta   63600
ccagcccgcg ctggaggacg cgctgatcgc gcgcggcgag gcgctgccgg gggttcaggt   63660
gcggcgcggc tgggaggtga ccgggctgac cgaccggggc gaccacgtgc gggtggtggc   63720
caccgacccc ggcggggcgc gcgtgaggct gacgcgcgg ttcgcggtcg gctgcgacgg   63780
ggcgaacagc gtggtgcggg cccgcaccgg caccgacgtg accgacctgg acttctcgca   63840
cgactggctg gtgtgcgacg tgcggctgca cgaccggcgc ccggtgacgc cgaacaacct   63900
ccaggtgtgc gacccggcca ggccacgcac gcggtgtcg gcggggccag ggcaccggcg   63960
gtacgagttc atgcgggtgc ccggcgacga cccggagcgg ttcggcacgc cggagagggc   64020
gtgggagctg ctgcgcgctgt tcggcgtcgg gcgcggcgac ggggtgctgg accggctggc   64080
cgtgtacacg ttccaggcgc ggtgggcgcg gcggtggcgg gcgggccgga tgctgctggc   64140
```

```
cggggacgcc gcgcacctga tgccgccgtt cgccgggcag ggcatgacct ccgggttccg    64200
ggacgcggcg aacctggcgt ggaagctgga cctggtgctg cgcggcgagg ccgggtcggc    64260
gctgctggac agctacacgc tggagcgcgc cgagcacgtg cggcacgccg tgacgatctc    64320
ggtgggcctg gggcgggtgg tgtgcgtggc cgacccggcg gtggctgcgg accgggacgc    64380
ggcgatgctg gcggcgcgcg agcgcgagct gacaccgggc gcgtcggccc ggtcggtgct    64440
caagcccctg gaggacgggg tgctgcaccg ggacggcgac ggcgccctcg cgccgcacgc    64500
gggggccgtg ggcccgcagt ggcgggtggg gcgcggcggg cgggtcgggc tgttcgacga    64560
cgtggtgggg accgggttcg cgctgctcac caggggcggg ctggtggcgg ggccggaggt    64620
gcgggcgcgg ctggacgggc tgggcgcgcg ctacgcgcac ctggtgcccg ccggggcggc    64680
ggcggacggg ccggacgacg tggtcgacgt gagcgggaac tacctgacgt ggctggagga    64740
gctggacgcg cggcggtgc tgctgcgacc ggacttctac gtgttcggcg cggccgggga    64800
cgcggcgggg ttggccgggc tggtggcgga cctgcgcgcg cggttggggt gacgccccgc    64860
aggccccggc acgtgccgcg ccggggcctg ctcgcgcgtc acgtccggtc gtcggcgagg    64920
tgggccaggc accagtcgag cacctgcgag ggcttgcgga ccaccgcgtc cgggttcgcc    64980
gccagcagct ccgcctcgtc cgtctcgccc cacagcgcgg ccagcgccgg gtagcccgcg    65040
gcgcgggcgc tggccaggtc cgtcagggcg tcgcccacca tcaccacccg gtcggccggg    65100
acgtcgagca ggccggtggc cagcaggagc atgtccggcg cgggcttggg gttcgcgacc    65160
tcgtcggagc cgatgatatg gtcgaacagc cccgccatgc cgagggtggt cagcagcgac    65220
cgggcgcgcg gcccgctctt gccggtgacc acggcggtgc cgaagccgtg ctgccgcagg    65280
tccgccagca gctccggcgc gccctcgaac acctccacct cacccgccag ccggtagctc    65340
tcgcggacga acggaccctc catctccagc ggcaggtcca tgatccgcat gatgtccggg    65400
aagtaccgcc ccaggtgccg gttgtactcc tcgaacggcg cgggcccgtc gccgacgacc    65460
tcggcgtagg cgatctcgaa cgcctgccgc atgacggcga agctgttgac cagcaccccg    65520
tcgaggtcga acagcacggc ccggtcgtag gtcgcgccgg ggacgtgccg gtggggcgcg    65580
ggggtcggcg gggcgagggg gcgcggggcc gcgggcgccg gaaccgcggt cgcggcccgc    65640
tcgtccccgg ctcgggcccg cacgactcgg gggttggtct gtccggtggt catcacgggg    65700
ctcccgtcgg gacgaggtcg accggcgcgt gtcgtcgttc ggcgcaccgc acggtgtcgg    65760
cggcgcggta gacccgttcg atcgcgcccg cgatccagcg cgccccggac gccgcctcgc    65820
cgcgcgtggc ggggtcggcc aggcgggtgg gcaggctcgc gagctgggcg tcgtactcgg    65880
cgcccaccgg ctcggcgggc agctcgaccg gggtggtgcg gccgtcggtg gtgagcagga    65940
gccgcgacgg gccctcgcgg ttcgggctga agccgaaggt gcagcgcagc tccgccgtgc    66000
cgccgctgcc ctccacgcgc acgaccgtgg tgtccagcgc ctggtgcgag gcccaggccg    66060
cgcgcacccc gatcgagatc cccgaccggg tgacgaggaa cccctggcg gtgtcctcca    66120 cgtcgccgac caccgggtcc accggcgccc cgtcgccgcg ccaggcggcc cggaacgcgt    66180
ggtcgttgac gaagtccgcg gacaccgcgc cggtgacgtg ctccagctcc gcgccctccg    66240
ggtcgccggt ggcgccgcgc agcagcacgc gggcggtgtc gagcaggtgc cagccgaggt    66300
cgaccagcgc gccgccgccg gagcgggtgc ggttggtgaa ccagccgccc cggtccggga    66360
tgcccttgga ccgcacccag gacacgtcga cgtgccgcag cgcgcccagc gacgcggcca    66420
cctggcgcag cgcccgcacg tcggcccggt gccgggcggc gctccgcccc agcagcaccg    66480
cgccaccggc ctgctcggcg gcggtgagcg cggcggcctc ggcggacccc aggcacagcg    66540
```

-continued

```
gcttctccag gaacaccggg acgccccgcc gcagcagacc ggacgcgacc ggcgcgtgca   66600
ggtggttcgg cacggcgacc acggccaggt cgacctcgtc gcggcgcagg tcctccaccc   66660
gctccagcgc ggtgatcccg cgggagccgg gcacggcggc gcgggcctgc gcggacggct   66720
cgaccacggc gacgacccgg aaggcggggc tgcccagcaa ccggggcagc cacacctccc   66780
gcgccaccca cccgagcccg accaccgcga cccgcaccgg accaccgctc ccggccctcg   66840
gcccgtcgct cacaccacca cccccgctcc ccgcgcccgc caccccgcgc tcacgcgccc   66900
gcgaccacgt cggccacgac ggcggcaagc cggtgcagct gctcctcggt gcccagcagc   66960
acccggtggt gcagccacac gcagtcgcgg gtgatctcct ccgacaccgg gcaccgggcg   67020
gccagctcct cggtggtcag gtcgggcgcg ccggtctccc agaacgcctg ggtgcggtag   67080
accgcccgga acgccatgaa cgccgggatc ccgcgccgca ccagctcgtc caccaccgcg   67140
ttgcgccgct cctcggtgac gccgggcatc cggaacatcg ccatgtagct cgggttgcgg   67200
tcgctgcgcg ggtcgacggt ctgcggcacg acgccgtcga tccccgccag cagcgcggac   67260
agcaccggcc agcgggcctg cctggtcgcg atctgcgagt ccagcctgcc gagctgggcg   67320
cgcagcacgg cggcggagaa ctcgttcatc cggaagttcg agcccgaggt gaggtggaag   67380
tagccgcggt cgcccttggg cctgccgcag ctgtgcagga cgaacgcctt ctcccactgg   67440
gcctcgtcct cgaacagcac ggccccgccc tcgcccgccg tcatcagctt gccgttctgg   67500
aagctgaacg tggcgatcga cccgagctcg ccgacccgct gccgcgcca gtgggcgccg   67560 tgggcgtggg cggcgtcctg caggaccggc acgccggtgc tcgtggacag cttgtccagc   67620
cggtccatgt cggcgaactg gcccgccatg tgcacgggca tgatcgccga ggtgcgggag   67680
gtgacggcgg cctcggcggc ggcgacgtcc aggcagtagg tgtcggggtc gacgtccacg   67740
ggcacggcga ccgcgccgag gcgctgcacg gcctgcgagg acgagatgaa ggtgaaggcg   67800
ggcacgatca cctcggcgcc ggggcccacg tcgagcacct ggagcgccag ctccagcgcg   67860
tgcgtcccgt tggtgacggc gagcgcgtgg cccgcgccgt ggtactcggc gaactcgcgc   67920
tcgaactcgt cgacctcgct gccgccgacc cgccaccact ggccctggtc cagcgcgcgc   67980
agcagggccg tgcgctcggc gtcgtcgtgc tgcggccagg ccgggaactc gatgcctgcg   68040
tccggagaat tgctcatgag cccctgtccc gtcgttcgcg gaaatggcgc gggggaattc   68100
gccgcggcct gctttcggaa ttcgacgcta ccgattccgc agatcccgac caacccccct t   68160 gacctccccc taatccccccc tgttcccagg ccatcaccgc agcacgcggg cacagcggca   68220
cagccgtgcg cacaatgggg gcgaacggga accggggcgt ccgcgcgccc cggcggcgct   68280
ttcggggaaa ggtgtcaggc gtgggcgagc tgctgctggt gaacgggccg aacctcggca   68340
tcctggggcg ccgcgaggtg tcggtgtacg ggaccgacac gctcgcggac gtcgagaagg   68400
cggtcggcga ggaggtcgcc gggcgcggct ggtcggtccg ctcggtgcag cgcaacggcg   68460
agggccagct cgtggacgag atcgaggcgt cctacgacac ggtgggcgcg atcgtgaacc   68520
ccggcgcgct gatgatggcg ggctggagcc tgcgggacgc gctggcgaac tacccgcgcc   68580
cgtggatcga ggtgcacctg tcgaacgtgt gggcgcgcga gagcttccgg cacgagtcgg   68640
tgctggcgcc gctggcgagc ggtctcatcg cgggcctggg cgcgcgcggc taccggttgg   68700
ccgcccgcgc gctgctggac ctggtggact gaccgccgtc gcgcgcgagc ccggccgcgt   68760
gcacggcccc gcgcagcgag gacaggccgc cgagcagcgc gggccgcacg ggcgcggtcg   68820
ggtggccggg ccgggcgagt gcggcgcagc ggtcggcgac cgcgtcgacg tatccgggca   68880
cggcggcggc gaacccgccc ccgaccacgc acagcgaggg ccgcgccagc tcgccgacgc   68940
```

```
cgacgagcgc ggcggccagc gcccgggccc cccgctcgac cgcggcccgc gcccacccgc   69000
gcccgtcgcc gagcgcccgc accaggtcct ccccggtgac cggcgcgccg ccgagcctgg   69060
cggcctcggc gagcacggcc ggtccggacg cgaacgcctg cacgcacccg gcccgcccgc   69120
acgggcaggg cggcccgtcg agcgccacca cgacgtgccc cagctcgcag gacccgcgct   69180
cgggtccggg gaacggcagg ccaccggaca cgacgccccc gccgacgccg gtccccacgc   69240
ccgcgtagac caggtcggcg cacccgtggg cacgggcctc ggcgagcgcg gcgaggtcgc   69300
cgtcgtccgc gacgagcacc ggggcggcca gcccgccgag gaaccccgcg aggtcgacgc   69360
cgacccaccc cggacggctg gccaggccg tgacgacccc gccgtcgacg gtgccggga    69420 acgcgatccc gaccccgtcg agcggcgccc cggcccgccc ggcgaggtcg gcgacggcgc   69480
ggccgagcag gtcgaggtcg gcgcgcggat caccgtcccc aggccaccgg aagccctccc   69540
gcagcaccag cggcccgcgt tcgagccgca gcgccacctt ggtcccgccg acgtccaccc   69600
cgagcagcgc cccgctcaca ccccgacctc ccgccgtccg cacccctcgc cgcaccacca   69660
cccgcgcggg ccgccgccca cgacgccgcc cgccacaccg ataccgcgc ggtcctcgct   69720 cacgacgccg ccacaccacc accgcacggg cctgcggtca cgacgccgcc acacctccac   69780
ccagcgcacc accacccgcg cgggccgccg ctcacgaggc caccgctcac gacgccgccg   69840
cccgccaggc cgccaccgcc tcggcccgcc gggcgtcgcc gctctccacc agcgcgaacc   69900
ggatcgcccg cgtggccgcg ttcgccgcct gcagcgcctc gtgcgcgccg ggctcggggt   69960
cgctgcgccc ggtcgccacc tcggtgatgc tgcgcgccgc ctccaggcac gccaggcagg   70020
ccgcgacgta cgcgtccgcc ccgcctcccg cgccgcccag cttctccagc agccgcgtca   70080
cgtcggcgtg cacctcgcgc acggcgtcct ccaccggcc cgcgccgggt ggtgtgccgg    70140 ggatggggt caccgctgcc tcccggtgcc tgacgcggac ccggtcagcc gagggccggg    70200
atgagttcga cgaaccgacc ctgccacaac cggcgcagct cgcgcgtcaa ctcctcggac   70260
ggcgcgccgc cgaccagctc cgccagggtc gtcacgccgt ccacccggct gagcagcgcg   70320
tgcgcctgcg cggtggtggc ggtgacgggc ccgtggtcgt actccagcga cacctcgtgc   70380 accgctcgc ccgccgccgc gctgcccggc gcgggcgcgg tgcgcacggc caggcgggtc    70440
accgggcgca gcctgggcac cagcgcgccc aggtcctgct cggggcgggc ccgcaccagg   70500 aagcccctcca cgaccaggcc gtccaggtcg gtggtcagga agctggtgag cacgtcgtcc   70560
aggctctgcg cgatcggctc ggcgttgttg ttgaacgagg tgttgagcag caccggggtg   70620
ccggtcagct cgccgaaccg cgccaccagc cggtggaagc gctctcccga ctcgggcgtg   70680
acgacctgca cgcgcgcgct gccgtccacg tgcgtgaccg cgcccagctc ggcccgcctg   70740
gcgggcagca ccggcaccac gaacgacatg aactcgtggt gccccagcgc cccggacagg   70800
tcgaaccagt cccgcgcggc ctcggcggtg accacgggcg cgaacggccg gaagctctcc   70860
cgcttcttca ccatggcgtt gatcgcgtc tggttctccg cgggccgggc gtcggcgatg   70920
atgctgcggt gcccgagcgc gcgcggcccg aactcggagc ggccgtgcgc ccagcccagc   70980
acctcgccgt cggcgagcag cttcgccgcg gtctccaccg gtccaccag cggcgtcacc    71040 tccaccaccg gcgaccagtc cgcgagccgc gcggcgacct gctcgtccgt gccgaggtcc   71100
ggcccgagcg ccgccgacac cagcgcgccc gacggccgct ccagcacgcc cagcgcggcg   71160
gctgcggcgt acgcggcgcc ctcgccggcg cccgcgtcgt gcgaggcggg gtggatgaac   71220
acctcgtcga acagcccggc cttgaggatg cggccgttga gcgtggagtt gtgggcgacg   71280
ccgccgccga acgcgagcgt gcgcagcccg gtgacctcgg cccagtgccc gagcacgtgc   71340
```

```
agcgcgatct tctcggtcgc ctcctgcagc gcggcggcga agtcccggtg cgcctggctg   71400
aacggctcgt ccttgcggcg cggccggaac ccggcggcga ccagcgcggg ggtgaccagg   71460
ttcggcacct tggtgttgcc gatcaggtcg tactcgccct tgtcgcgcag cgcgtgcagc   71520
ccggagaaga cctcgcggta ggtcgacggg tcgccggacg gggcgagccc catgaccttg   71580
tactcgtcgc cgaagccgta gccgagcagg aacgtggcgt tcaggtacag cccgccgagg   71640
gacttctcca ccgggtagtc gtgcagcttc tccaggtgcg cgccacgcgc gtggtagacc   71700
gtgccggagt tgtcctcgcc ccggccgtcg aagatcacca ccagcgcctc gtccgcgccc   71760
gagtgcaggt aggacgagta ggcgtgcgcc tcgtggtgcg gaacgtagac gagcttgtcg   71820
tcgggcagct cccagccgag gtcctcgcgc agccgctgct tgatcagctc gcgggagaac   71880
cgcagcggca ccctcgggtg ctcggtgtag acgtggttga gcaccaggtc gaggtggtcc   71940
tcggggaagt agtagccgac cgcgtcgacg tcgtccacgg tcgcgcccgc gagcgccagg   72000
cactcgcgga tggcggtgga cgggaacttg gtcgtcttct tgacgcggtt gagccgttcc   72060
tcctccacgg cggccacgag ctcgccgtcg cgcaccaggg acgctgccgc gtcgtggaag   72120
aacagctccg acatcgacgg gacgaggtcg gtctcggcgg gcgagaagtt cccgttgatc   72180
ccgagcacga gcatgtggca tcaccttgat ccggaggcg agggctgggg cgcggagggg   72240
gtcgccgtca ggcgcggggc gcgacggcgg cgaggtcggg cgaggtcagc cgcagcgcgg   72300
tgggcgcggg cttcgcggtc ggcacgaggt ggaagcgctc cacgccctcc tcggtgggcg   72360
cgggcagctc ggcggcgcag gcgcagtcgg cggggcgaa cccggcgaac cggtaggcga   72420
tctccatcat ccggttgcgg tcggtgcgcc ggaagtcggc gaccaggtgc gcgcccgcgc   72480
gcgccgcctg gtcggtgagc caggtcagca gcgtcgaccc ggcgccgagc gagacgacgc   72540
ggcacgaggt ggccagcagc ttgaggtgcc acacccgccg gcgccgctcc agcagcacga   72600
tgccgaccgc gccgtgcggc ccgaaccggt cggacatggc cacgaccagc acctcgtgcg   72660
cggggtcggc gagcaggccg cgcagcgccc ggtcgtcgta atgcacgccg gtggcgttca   72720
tctggcttgt gcgcagggtc agctcctcga cgcgggtcag gtccgcctcg cccgcgcgcg   72780
cgacgaccac ctccaggtcc agggtgcgca ggaactcctc gtcgggcccg gtgaagccct   72840
cgcggctggc gtcgcgctcg aagcctgcgc ggtacatcag ccgccgctgc cgcgagtcgg   72900
cggtgaccac ggcggggctg aactcggggc gctcggcag ggaggcgacg tcggcctcgg   72960
tgtacaggcg cacctcgggc agggcgcggg ccacctcggc gcgctcgacg gggctgtcgt   73020
cgacgaacgc gatcgtgcgg tgggcgaagc cgagccggtc ggcgatggcg cgcaccgacg   73080
ccgacttggc gccccagccg atctgcggca gcacgaagta gtcggcaagg cccaggcgtt   73140
cgagcacggg ccaggcgtgg tcgtggtcgt tgccggctggc cacggactgc aggacgccgc   73200
gcccgtcgag cgcggtgatc acctcgcgga cccgctcgaa cgggacgacg tcggcgtcct   73260
ccaggagggt gccgcgccac agggtgttgt ccaggtccca gaccaggcac ttgaccgtcg   73320
gtgcgggggt ctcggtcacg gctgctgctc cctgagcgga gttcggctgc gctggtcaag   73380
tccgcgcggg gcccggctgc gcacgtgctg ggcgagcacg agctggcaga tctcggaggt   73440
gccctcgatg atctccatga gcttcgcgtc ccggtgcgcc cgcgccacca cgtgcccgtc   73500
gctgcgcccc gcggagccga gcagctgcac cgcgcgcccg gacccggcgg cggcctcgcg   73560
cgaggccagg tacttggcct gcaccgccgc caccgccagg tccggcgagt tcgcgtccca   73620
cagcgcgctg gcgtgctcgc tcgcgcgggc ggcgacctgc tcgccgacgt gcaactcggc   73680
caggtgccgg gcgacgagct ggtggtcggc cagcacgccg ccgccctgct cgcgggtcgt   73740
```

```
ggtgtgctcg acggcggcgg ccaggcaggc gcgcaggatg ccgacgcagc cccacgccac   73800
cgacacccgc ccgtaggtca gcgcggcggt gaccaccagc ggcagcggca gcccggtgcc   73860
gcccaggacg tcggcggcgg gcacccgcac cccgtccagg gtgatcccgg agtgcccggc   73920
ggcccggcac ccgctggggt tcggcaccct ctccacccgc acgccgggcg cgtcggcggg   73980
cacgacgacc gcgctcgccc cgccccggta gtgcccgaag accaccagca ggtccgcgta   74040
gtgggcggcg gtgatccacg acttgcggcc ggtcaccacc acctcgccgt cgccggtgtc   74100
ggtgatggtc gtggtcatcg cggacaggtc gctgcccgcg cccggctcgc tgaacccgac   74160
cgccgccagc ccgcccgagg tgagcctgcg caggaaccgc tcgcgctgct cggcggtccc   74220
gagcctgcgc gcggtccacg ccgccatgcc ctgggaggtc atgacgctgc gcagcgagcc   74280
gcacagctcc cccaccgacg cggtcagctc gccgttctcc cggctgccca gcccgaggcc   74340
gccgtgcggg gcgccgacct gggcgcacag caccccagc ccgcccagct ccaccagcag   74400 ctcgcgcgg agctcgcccg ccaggtccca cccggcggcg cggtcgccga cgcgctcggc   74460
gaccagcccg gccagtgcga cggcgtcgct caccgccccg cctcccgcag ccgcagcacc   74520
agcgtggtca tggtgttgac ggtgcggaag ctgtccaggc ccaggtccgg cccgtcgatc   74580
acgacgtcga aggtcgactc caggtgcacc acgagctcca tcgcgaacat cgaggtgacg   74640
gtgccggacg cgaacaggtc ggtgtccggc tcccaggtct gcttggtgcg ctcggcgagg   74700
aacgcctgca cccgctcggc caccgcgtcg gcggtgagcg cgccgggctg ggaggaggtc   74760
gtcacagctg tgccttcccg tagtcgtaga agccccgccc ggacttgcgc ccgaggtgcc   74820
cgtcgcggac cttgcgcagc agcagctcgc agggcgcgga gcggggtcg ccggtgcgct   74880 cggccagcac gcgcagcgag tcggccaggt tgtccaggcc gatcaggtcg gccgtgagca   74940
gcggtcccgt gcggtggccg aggcagtcct gcatgagggc gtccacggcc tcgacggagg   75000
ccgtgccctc ctggacgacg cggatcgcgt cgttgatcat cgggtggacg atccggctgg   75060
tcacgaagcc ggggccgtcg ccgacgacga ccggtgtgcg ggccagctcg cccagcacgc   75120
ccacgagggt ctccagcgcg tccgcgccgg tgcgcgcgcc ccggacgacc tcgaccgtgg   75180
ggatcaggta cggcgggttc atgaagtgcg tgccgatcag ccgcgccggg tcggggacgt   75240
gcccggccag ctcgtcgatc gggatcgagg aggtgttgga caccagcggc acgcgcggcc   75300
cggtgagcgc ggcggccccg ccagcacct cggccttgac cggcagctcc tcggtgaccg   75360
cctccaccac cagcgagacg tccgcgacgt cggcgagcga ggtggtggtg agcagctcgc   75420
cccgctcgcg gtcctcgggc agcgcccgca tcagcctggc catgcgcagc tgggcggcca   75480
ccgcctcccg cgcccgcccg accttggccc ggtcggtctc gaccagcacc accggcacgc   75540
cgtgcccgac ggccagggag gtgatcccca ggcccatcgt gcccgcgccg agaacggcga   75600
gcaccgtcct gccgtcctgc tctcccatcg cgctcccccg ccgcggccac cgcggccgcc   75660
gtccggtccg cgcgccgtcc cggcacgcgc attccaccct cgatcgtgtg ccgggaaagg   75720
cgcgcccgac cccctgacct gccccccctga accccctca acggaaccgg aaatcgaatg   75780
tcccgaacgc gccgtcaaat cgtcgattga cagccgcaga actgttcata gactgtggcg   75840
gcagtaccga tctccgaatt ccacggaaga gtcctccccc atggctcagc agatcagcgc   75900
cacctcggaa atcctcgact acgtccgcgc gacctcgttg cgcgacgacg acgtgctcgc   75960
cggtctgcgg gagcggaccg cggttctccc ggccgcgtcc gcgctgcagg tggccccgga   76020
ggaggggcag ctgctcggcc tgctggtgcg cctggtcggc gcgcgctcgg tgctggaggt   76080
cggcacctac accgggtaca gcacgctgtg catggcccgc gccctcccgc ccggcggacg   76140
```

```
tgtcgtgacc tgcgacgtcg tcgcgaagtg gccggacatg ggcaggccgt tctgggagcg    76200
ggcgggcgtc gcggaccgca tcgacgtccg cgtcggcgac gcccgcgcca ccctggccgg    76260
cctgcacgcc gagcacgccg tgttcgacct ggtgttcatc gacgcgaaca agtcggatta    76320
cgtccactac tacgagcgcg cgctgacgct gctgcgcacc ggcggcctgg tcgtcgtgga    76380
caacacgctc ttttcgggc gggtcgccga tccgtccgcg accgatccgg acaccaccgc    76440
cgtgcgcgag ctgaacgcgc tgctgcacgc cgacgagcgg gtcgacatgt gcctgctgcc    76500
gatcgcggac ggaatcacgc tcgccgtgaa gcggtgaacc cgcccgaatc gcgccgaatt    76560
cccccggaga gaaaggccgc cgcagtgttc accgaggacg tggccaccga cctgcccgcc    76620
tacccgttcc tgcgggaccg gggcgactgc ccgttcgcgc accccccgcg ctacggccaa    76680
ttacgggagg agcagcccgt caccagggtc cgcctgtggg acggcagcac cccgttcctg    76740
ctcaccggtc acgaggtgtg ccgcaccgcc ctgaccgacc cgcgcttcag ctccgacggc    76800
gccaaccgcg cccagccgcg cttcgtgaag ttcgacatcc cggacgacgt gttcaacttc    76860
ggcaagatgg acgacccgga gcacgcgagg ctgcgccgca tggtcgccgg gcacttcgcg    76920
agccgccccg tggaggcgat gcgccccgcg atcaccacga tctgccacgc ccagctgcgc    76980
cagctcgtgc aggcgggctc ccccgccgac ctggtggccc actacgcgtt cccgatcccg    77040
tccctggtga tcggcggcgt gctcggcgtg gcgggccccg gcctgacgga gttcgcgcgc    77100
gactcgacgc gcgccctgga cccgtccctg tccgccgagg agatgggcgc cgccatcaac    77160
tcgatggtcg ggttcgtgga cgacctgtgc gcggccaagc gggccgcccc cggcgacgac    77220
ctgatcagcc gcctggtgct ggacttcgag cgcaccggcg agctgacccg gaagcagctc    77280
gtcgccaccg tgatggtcgt gctgctggcg ggctacagag ccaccgcgaa catgatcgcg    77340
ctgggcacga ccgcgctcct gcgcgacccc gagcagctgg ccttcctgcg cgccgagccc    77400
gccggtttcg ccaacgccgt cgaggagctg ctgcgctggc acaccatcgt ccaggacggc    77460
accggccgcg tggccctgga cgacgtcgag ctggacggcg tgctcgttcc cgcgggctcc    77520
ggcgtgatcg tcaacctgcc cgcggccaac cgcgaccccg acgtcttccc cgatcccgac    77580
cgcctcgacg tgaccaggca caacgcccgg cggcacttcg cgttcggcta cggcgtccac    77640
cagtgcgtgg gcatgacgct ggcgcgcgtc gagctgcaga tcgcgctgga gaccctgctg    77700
tgcggcctgc cggcctggc gcctgccacg ccgttcgagg acctggactt cgccctggag    77760
tccatgaacc tcggcctgcg ctcgctgccg gtcacgtggt gagcaccgac cgtccaccag    77820
gggagagccg atgacccgca ccaccccac ccccgacctg gccccggagt tcccgatgcc    77880
caggtcgccc gagcacccgt tcgacccgcc cctcgactc cgcgaggcgc aggaggcggg    77940
cggcctgtcg cgggtcgcc tgtgggacgg cagcacccg tggctgatca ccaagcacgc    78000
ccaccagcgc gagctgctgc gcgaccccg cctcagcgcg gacttcctgc gccctggcta    78060
ccccagcccg attcgcatcg aggacaagtc gacgttcatc agcagcttcc cgctcatgga    78120
cgaccccgag cacaaccggc agcgccggat ggtcctgggc ccgttcaccg tccgcaaggt    78180
ggaacgcctg cgcccgttcg tgcagcggat cgtcgacgag aagatcgacg aactcctcgc    78240
gggccccaac ccggtcgacc tggtcaccgc gttcgcgctg cccatcccgt ccctcgcgat    78300
cagcgccgtc ctgggcctgc cctactccga ccacgaggtc ttcgagcgca acagcgccgt    78360
gctgatccgc caggacgtgc ccccgcagga acgggccgag ccagcgagg agctccagca    78420 ccacctcgac cgcgtcctgg gcgacaagat gaccgacccc gccgacgacc tcctctccga    78480
cctgggcgca cgggtgctgg caggcgagat cagcaggccg gaggcggtcg acatgaccgt    78540
```

```
cctggtgctg gcgggcgggc acgagaccac cgcgaacatg atcgcgctcg gcaccctcgc    78600
gctgctccgg caccccgacc agctggcgct gctccaggcg ggcgacgacc ccgccctcgc    78660
cgagaccgcc gtcgaggagc tgatgcgcta cctgacgatc tcgcacaccg ggatgcgccg    78720
cgtggcgacc gaggacgtgg agatcgacgg ccaggtgatc cgcgcgggcg agggcgtggt    78780
gctggcgacc tcgatcggca accgcgaccc cgacgtctac gacggcgacc cgcacgtgct    78840
ggacctgcgc aggccggtga agcagcactt cgcgttcagc ttcggcaccc accagtgcct    78900
gggccagtcg ctggcccgca tggagctgca ggtcgtcgtg aacaccctct accgccgcgt    78960
cccgaccttg cgactggcga ccgcgctgga gcgcatcccg ttcaagcacg acgggatcgt    79020
ctacggcgtc tacgagctgc ccgtcacctg gtgaccccgt cccaccagac ctcctgccac    79080
gcagacctcc cgcaagccga ccccgaaagg ccgttcccat gagcgacacc acgctgtccg    79140
tgcccgtccc cgaggaggtc ggcaagctct acgaccagat cctgaaggac gagcacacct    79200
acgagcagtt cgagaagttc aaccaccagc tgcacatcgg ctactgggac gacccgacct    79260
cggacgtgcc catgcgcgag gccgtggtgc gcctgaccga gctgatggtc gagcgcctgc    79320
gggtggacgc cgaggaccgc gtgctggacc tgggctgcgg catcggcggc ccggcgaccc    79380
agatcgtgcg caccaccggc gcacgcgtcg tcggcgtgag catcagcgag gagcaggtca    79440
agctcgccac caggctggcc accgaggcgg gcgtgggcga ccgcgccacc ttccagcgcg    79500
ccgacgccat gcggctgccg ttcgaggacg agtccttcga cgcggtgatg gccctggagt    79560
cgatcctgca catgccgtcc agggagcagg tcctgtccga ggcgcgccgg gtcctgcgcc    79620
ccggaggccg cctggtcctc accgacttct tcgaacgcgc accccgcacg ccggggatgc    79680
accccgcgat cgagggcttc tgccgaaccg cgatgacgac gatggccgac gtggacgact    79740
acgtgccgat gctgcaccgg gtgggcctgc gcgtgcggga gctgctggac atcaccgagc    79800
agaccatgga acgcacttgg cgggagaccc tggagatcgt cagccagaac gaccgcccgg    79860
tcgacttcga cctggcggag ctgttcggcg tggacgagtt cggctgcctg ctggtcgccg    79920
cagaccgccc gtgaggcccg tccccgaggc cgtgggccgc ctgtacgacg acctgctgga    79980
ggccgagctg gaggggggcg cagccgaccc gaacctgcac atcggctact gggacgcgcc    80040
ggactcgcca acgccacgcg cggaggcggt agtgcgcttc accgacgaac acgtccgccg    80100
cctgcacgtg accacgggcg accgagtgct ggacgtgggc tgcggcgtag gcggcccagc    80160
cctgcgcgcg gtggacctga ccggcgccca cgtgaccgga atcagcatca gcgccgccca    80220
gatcacccac gcgacccacc tggccaagtc gcgcgggccac gcggacaaca ccaagttcct    80280
ccacgcagac gcgatggccc tcccgttccc ggactcctcg ttcgacgcgg tcatggcgat    80340
cgagtccctg atccacatgc ccgaccgcga gcgggtcctg aacgaggcaa gacgcgtact    80400
gcgcccaggc gggcgactgg tcctcaccga actgttcgaa cgcgcccaa gacccacccg    80460 cagacaccca gcgataaccg agttctgccg agcatcgatg gtgtccctgc caacgcaga    80520 cgactacccc gcactactac accgagcagg cctacgccta cgggaactcc tggacatcac    80580
cgaccacacc gtccaacgca acttccgcga actggccgat ctggtaggcg acgcgaaggg    80640
cctgctgttc cacccacgcg acctggtggg cgtcccagaa ttcggctgct tcctagcagt    80700
agccgaacac ccgtaaccac gcggtggcgt ccccacgga cgccaccgcc tcgcgggctg    80760
cggggcgagc gcagcgagcc cgcgcagccc cactcccgcg tccctcttct ccgtgtggcc    80820
tggcgcatgt caaattccca ctgactgcca acagatcatg tgccgtttga gcaggtcagc    80880
gacttgtcgc gcttcggtgc cttaaggccg agctgggatg ggggcactgt ttccggactg    80940
```

```
agcggggcag cttggaaggt ggagttcggt gagcagaggc agcacgtccc gtcgcacgta   81000
gaggtggttg tacacgcggt ggcgggacct gcgcagtagg ccgctatccg caagctgctc   81060
caagatcagg agtgcggcgc ggtgcgtata gccgagttcg gcggtcagca tggtgctgtt   81120
gagcagtggg gcgacgagca gcggggcggg aagcgctttg accttcctcc gcccggtgcg   81180
catcgcccag gtgggcgatc gcgcgagcct cacggatcgc ggtcacctca tgcaggctgg   81240
cgctcaacct ggaacgcgcg actgtttcgt ccagacgtgc cagggcggtg taggcgtgca   81300
acaaggtctt gctggtttcg gagcgcagtc tgagccggga ccaggacgac aactccgcga   81360
tcctcgcgga cggggcggc ctcgtgtctt caccggtggt agttgacctg cgcggggcgg   81420
aggtgcccta ttgctgccgg gacgaggtca tcccccggag cagtttctca gcacgccgtg   81480
aatcgagatc cggggcgctg agcgcggtga acgcctcgtc cagcgagtcg cacgcgcacg   81540
tcgtcctgac atcgggccgc gcatggcccg aggtggtcag cggtgagcgg gaaggcgcgg   81600
cagggtgtgt gcgagacact ccgggactcc gtgcagaagg tcgatcaggc gaaagggttg   81660
aactgcgaat cgcaaagcgg cccggccgca aaggggtcgg gccgcctgcg acgattggtc   81720
acgctgctgc ggcgcggtcc cgccggaact gcttgccgag caggtcgatc cgcccttgt   81780
gatcttctgc cagcgcctcc agaaccgaga gcagtcgtcg ggcgtgcagt gcatggccaa   81840
taccatcgtc gcgtacccca gagggtgtcg ctcccgttca ggggcgacca tttcccacgc   81900
ccgcttggcc tccttggcgg cccggccaag atcgccgagc atcaggtagg tgcccgacaa   81960
cccgacaacc ctgcctgcca acgcggcttc cggcaccccg cgcgcctcgt cggcttccaa   82020
cgcccgaaca ccgtgccaca gcacggcccg cgcgttgccc tcgctcgtct ccagccatcc   82080
catgacaccg tgcgcttcgg ccagtgacca cgatcggctg tcgggatcgg tgttgcacaa   82140
cgccagctcc agcgctcgtt cagcagcgtt accgaccaca gcgcggcgcc gatgtccagc   82200
acttcttgcc ggtacccgcc cacgagtgcg gcggtgcgct gcacggccac gacttcccgc   82260
cgatgcacga tcagccactt gtacgccgcc aaggcgttgt cgaacagcgg cttcgccccg   82320
acctcgaagc cgtcgacgaa cacctcgcgc aaatcaccga gcagtttccc tgcggccaag   82380
gtgcgccgat gcaggtacct gcccaagcgc tccaactctt gcgggaactc ctgctgcaca   82440
gcccatcgca gcagtgcctg ggcttggtct gtctcctgcg cgcgatggcg accggccagc   82500
cggtaacgcg aggaggtgaa ctcggggtgc gtgatgttcg ggtgaagttc agtccacgaa   82560
ggctgcgtca gcaccagcac gccctggttc acccagtccc gcgcgtgttg ggcggtctcc   82620
tcgacggtga ttcccagcat cgcggccaac gacgaggtcg agaccacggg gtccggcagc   82680
aggtccagca atctcagctc ttgcggaatg ggcacaagag tgttgatcat cgatgcccct   82740
cccggaggac ggcgatgatt ggagtggcga acagaagggg aaacgccagt cgccgggtt   82800
ccggcggtcc acgcgccttc ggccggccac ttggactccg acgggcagaa gttcaccggc   82860
aaggactctg gtgacggtgg agcggtgcac gcccatcgct tcggccaagg cgtagtcgct   82920
gtggtaacca gcgaactgag ctagctttcg catcttgtcg ccgcgcaccc cgacgacctt   82980
cttgatcttt tcggtctcgc tgtcgttgtc gtcgacatgt ccgccgtccg gcgctgacac   83040
cgttctcctt gagatcgccg agctgaatgg gggatgcttc gacgtaaggc gttgcgtatg   83100
cgcaacaggt caggcggcgt cgagtctccc cattaccgag gtttcgcttg atcgccgacg   83160
gggcccgcct cgaagaagtc caatcgagct ggcatcccct tcgattgatc aatagcgcga   83220
cgggtgtcgc tcgacatcgc cccaccgcct gctcctgacg tgccacgagc agggaggagc   83280
gacctccctc gggactgcac cgaccgttcc tccctgtccg ccgattcagt tgcattccgc   83340
```

```
cacgctaggt gccggatgcg ggccgaaggg acaacgaagg gacaagtcga acagcccagg    83400
tgcgaggtat cttgaaatag cccgaatcct ccgtcgcgaa gcaggtcgcc atgcccactg    83460
acgaacagtc cgagggtgtc ggagagcgca tagccgtcca acgcaaactg gctggcttga    83520
ctcagcaagc tctggcgaag cgcgcacacg tcagcctcag cctcatcaaa ggggtggaac    83580
agggaaggat tcccgcctct cccgcgctcg tgtcccaggt ctcgcgggcg ctcaaggtcg    83640
aggcgacgat cttgctgggg cagccgtacc gccccgagga tcggagcagt cttcgcgttc    83700
actccgtcat ccccggtctg cgccgagcct tggcggccta ccggttgccc gctgatgagg    83760
gcatcagccc tcgcgggtac gacgagctgg ccgccggtgt agccgccgcg tcgaagatgc    83820
gccacgccgc gacgttggac gtcctggggg ctgaactccc cggcctgctc gacgagatcc    83880
gctcggccat cgacgaggct cggggagttg agcggcagcg cctgttcagc ttgctggcag    83940
aggcatacgc agccgctggt caagtcgcgt ggaagctggg ttacgcggac ctgtcctccc    84000
tggcgacgga gcgcgtggag tgggcggcca aagagtccgg cgatccgctc gcgatgggcg    84060
cagcggactt ctacatcgcc ggtgagctga tcgcagcagc ggagtggcgc ggcgccctct    84120
cctacctcga cggctcccgt cgccgcctgg agcacgtggt gcgcaaggac gacgaggccg    84180
ccttgtcgat ctacggagtc ctgcacctga agtcggggct cgcggcggca cgggccggga    84240
aagccgacga atccgacgcg cacctcgctg aagcccgtgg catcgcggaa agggtgccgc    84300
tgggcagtga ccactaccgg ctcgcgttcg accgggactc ggtcaacatc tggaccgtgg    84360
ggctggcagt ggagcgcatg gacggcacgg aagccgtcaa acgagcccac gggatgcgct    84420
tcagcaagac cacccccgcgt gaacgcgtgg gccaccacta catcgatctg gcgcgcggct    84480
accagctgca cggagaccgt gaccgcgccc tgcacaccct tcagatcgcc aggcgaacct    84540
caccgcagca ggtgcgctac cacccgcagg tcagggaaac ccttctcacg ctcgcggaac    84600
aggaccgcag gcgctcggat tccctggcag ggctcgcgcg ctggatcggt atgccggtgt    84660
gacaggacgg cgagctgacg tcgctgttga ggggcagccc cccatcggcc gcccctcaac    84720
agcaggtgcc ggtacgtccc tcacagcgcg acgctgacga tcaggctggc gaacatggcc    84780
acggccagcg cgatcatctg cttgggcgcg ccgccgaaga agagggaccc cacccaccgc    84840
agtggtaaac cggcaccgag caccaacggc caccggccgg cagagcccgt ccccctcttt    84900
tttggaggtc tgccccgccg gcgaggcgtg cccttcagct ctcaagctct ccactctcga    84960
tcttgtggtc cgaacacccc ccgcacccccc actacgatcc ccccatgggg gctctgatca    85020
tcgcggtagt gctgctgctc gtcttcctcg tgcaactcaa gcgggaaccc agacgactgg    85080
gcaacggcgt ctacctgctg atgagcctgg cgttcttcgc cctctggctg ctcacccctcg    85140 ccaccccccca gaccaggacg ctggtggtag gcgcggtagt cctgatcgcc ccggtattcg    85200
tcaccgtgat cgccctgttc ctcatcgcca acggcgtcac cctgctgcgc gcgagggcg    85260 tcaaaccagg caacgccctc tccttcggcg caggcaccgc catcctgtgc gtcgtaggcg    85320
gcctgctcct ggtcctgctc tccgccctgc gcgaaggctc ccccgacccc tgggtgctgg    85380
cagcagccgg ttccctggtc ctcctggccg gctacctggg cttcgccttc accctcttcc    85440
tgctctactc cgtgctctac ggccgagtcc gcaagcgcac cggccacacc gcgatcatcg    85500
tcctgggcgc gggcgtcccc ggcggccgag tgacccgct cctggcaggc cgcctggacc    85560
gcgccctgaa gctctaccgc cgcgccgcag ccaagggcgc ttccccgtg gtagtcgcct    85620 ctggcggcca aggcccagac gaaccagcct ccgaagccga ggtcatggcc aactacctcc    85680
gcgaacgcgg catcccggac gaggccctcc tggaagagcg cgagtccacc tcgacctggg    85740
```

-continued

```
agaacctccg cctctcctcc gccctgctcg ccgaacgcgg cgtgaccggc agactcctgg    85800
tcgtcaccag cagctaccac gtcccccgag ccgcgatcct ctcccgccgc gcaggcctga    85860
aggcagacgt ccgcggcggc cgaaccgcct ggtacttcgt gccgaacgcc ttcctccgcg    85920
agttcgccgc cctcctggtc cagtaccgca ccctcaacgc cctggcagcc tgcaccgcac    85980
tctccgtctt cccgctcctg gcctacggcg tctgaaaagc acgacccggc cgaccggaca    86040
ccgcgtcaca gatccagcgg cgccgacccg aaggccacgt tgaaccggtc gcaccacacc    86100
acgacgctgc gcagccccga caggtccacg tcctccggaa tcaggtagtt ctggttgccg    86160
tcggtggcct tcatgggacc gagcggcagg tagcgcccat cgtcgtactt gccccactcc    86220
ccacccgcgg tcgcgtcgga gagccagatg tgcaggtcgg gccgtccga ggtggagaac     86280
ccatccagcc gcagcacgcg cgcggccccg ctgcgcagca cggtggcggt gccccgcgtc    86340
tcgtgctcct gggtgacgaa cccacccgtt gccagcaccg tcggctggtc ggcggtcgcc    86400
gacgacgtcc caccgggcgt cgtggcaccg ctgcccgccg ccgccccggt gctcgacgcc    86460
ccagccccgg tgctcacccc cgcaccggtc gagacgctga actcgcgggg cagcgcctcg    86520
tccgcctcgc tgccgcgtcca caaccgccac ggctggaaca cccacagccc gacgaccgca    86580
gccaccacca caaccccccga caccgcccaa accgctctcc tgcgcaccga accgcgcacc    86640
acgtcccctc ccgttctccg cagacgacct gccaccatgc cacgggtcgc gcccgatgac    86700
cacgaccacc gcgccacacc cgccccacgc agcgactagg ctgccaccg gggtcgccag     86760
ccgatcccga gcgggttgag caggcagccc accgcagttc gcgctagtgg gatgagggga    86820
gcgggccggt gtccgagctg gatgcagccg cggtggtcac ggtgggttcc gacgtggtgc    86880
gcggggtgcc cgtgctgcgc gtcgccgggg agatcgacac caacgtcgcc gacgaggtcc    86940
gccgggcgct gctgccctgg ctggacgggt tgcgcgggcc aggggtgctc gacctgaccg    87000
gggtgaggtt catggcctcc accgggttgt cgctgctgat cgaggccgcc cggcgcaggc    87060
cggcgaagct ggtgctggcc accgcccagc gcggcgtgct ccggccgctg cagctgaccg    87120
ggatgagcgc gctgctcccg acgcaccccca ccgtggacct ggccgtggac gcccagctcg    87180
gggccgccct ggccgggatg cccagcacgg cctgaccacc ctcggtccac gggcggcctg    87240
cccgcggacc acccgcacgg cgccctgggg ggacgagatc acagctggtg aagacgcga    87300
tcctggtccg cgcgccgcga cgccggtggg cgcgggcgct cccgccacgg cggcggaccc    87360
gcccccggtc cccaccacgg ctccggcacc ggccccgaca ccgacaccga ccccagcccc    87420
gcccctgggc acgaccacac caccaacccc ggtcctgggc gcaggtgtcg ccaccgccac    87480
cgccctgacg ctggcactcg ccggggccgc agccccagcc gacaacagcg cgggaaaggc    87540
ggccatcatg gacgaggtgg acgccccaac caccccaccc accccggccg cgctggacct    87600
cacgccccgc ccaccctgg ccgaggtgcg ccgctggacc ggcgcgctgc tgatcgacgc     87660
cgacgaggaa gcagcggacg acgtgctgct cgtggtcaac gagctggtcg ccaacgccta    87720
cgaccacacc acctccccac tcgccctgcg cctcaccacc acccccgagc acgtgcgcgt    87780
ggaggtcgag gacggctccc ccgacccacc acgcccggac ctcaccgcgg gcctgcgcca    87840
gatcggcacg cgcggacgcg gcctgctgct gatccgccag ctgaccgatc gctggggcag    87900
cacgccccac cccggcggca agaccgtgtg gcggagctg ccgaacgtcc cggcgacctg     87960
agcccgacgc cccaccaacg aggccacggc ggatctcacg ggaagagcgc ggcggggcac    88020
tccgggcgcg ttggacgccg gcgcactccc cggtgagggg tcggcggcg gagtggatga     88080
gcgtggcggc gagcagggcc ggtccggcgg acgagacggc catcagcagc ccgccgaccg    88140
```

```
gggccgcgag gcgtcgggcg cgggcgccga gcctgcccgg caccgggccg accacggagc    88200
tgacgccgag gacggcggtg caggcgccga gcgcgcgcct gcgggccgcg ccctcgaagc    88260
gcacctggac ggcggtcagc gccccggaga ccatgagcgc cgcgcccgcg ccctggacca    88320
cccgcgcggc caccagcgcc gggccggtgg gggtgaggcc gcaggccggg gaggcggcgg    88380
tgaaggtggc gggcccgacg aggtgggccc agcggcggcc ccggatctcg ccgaggtggg    88440
ccccggtgat cagcaggacg gcgagctgcg gcaggacacc gacacgggca cgaccgcgtc    88500
gatgtgcgtc gcggcggcgc agggcgcgga cgggcgcg gcgagcgct gagggcccgc       88560 ccggcgccac tcccccgtca cacctcccgc cgcagcacat cctcctccgt ctcccgccgc    88620
accagcaccc gcgccactcc gtcgcgcacg cccaccacag gcggcctgcc cacggcgttg    88680
tagttcgacg ccagcgcgtg gtggtaggcg cccgtcaccg gcaccgccag caggtccccc    88740
gcgcgcacgt ccgcgggcag cggcacgtcc tcggcgagca cgtcaccgc ctcgcagtgc     88800 ctgcccacca ccgtcaccgg cgcgcgccgc ccgcccggc cgaccaggcg caccgcgtac     88860
cggctcccgt acagcgcggg cctgggggttg tcgctcatgc ccccgtccac ggccacgaac   88920
acccgcctca ccccgcgctt gacgcagccc acccggtaca gcgtcacacc agcgcccgcg    88980
acgaccgacc gccccggctc gatcagcagc ctcggcaccg gcacgcgccg cagcgcgcac    89040
tcgtggctca gcgccacccg caccgggtgc gcgaacccgc caaggtcgaa ctcccctcc    89100 cccggcaggt agggcaccgc gaacccgccg ccgaggtcca gctgctcgat ccgcaccccg    89160
cacgaggcga tcagcccgac catccgccgc gccgcctcct cgtacaccgc gacgtgtcgc    89220
acctgcgacc cgacgtggca gtgcagcccc accagcctca gcgacggctg ctcgaccacc    89280
cgcagcaccg cctccagcgc gtccccaccc gccaggaga agccgaactt ctggtcctcc     89340
accccggtcg ccaccgcccg gtgggtgcgc gggtcgacgc cggggtgac ccggaccagc     89400 acgtcctgcg gcccctggc cagcgcgccc agctgctcga tctcgtcgaa cgagtccacc     89460 accaccccgcc cgaccccgta cccgagggcg gccttgaggt cctcgggcgt cttgacgttg   89520
ccgtgcagca gaatccgctc cgccgggaac ccgaccgacc gcgcgatcgc cagctccccc    89580
gccgagcaca cgtccagcga cagcccctcg tccgccaccc accggtacac ctcgcggcac    89640
ggcagcgcct tgcccgcgaa caccacctca gcctccggca gcacctcccg gaacccgcgc    89700
gcccgcgccc ggaccgtgcc ctcgtcgagc acctggcagg gcgtgccgaa ccgggcggcg    89760
agctcggtcg cgggcacccc gccgagcagc agctcccccc gctccagccg ggtccccagg   89820
ggccacagcc ccgcctccag ggccggttcg ccggtcatgc cgacgctggg cagcaactcc    89880
gcgagtgtca tgcccgccag cacacgcccg aaccggccgg ggcgacagcg gcgcgaacgc    89940
gtccctgacg gcgtgccggg cgggattgac gccgccctga cccgaccgcc ccagcccgct    90000
ctcgaacccg gcggaagcac ccccgaaacg cgccggaaac ccgcccgcgc attccccga    90060 acgcctacct cacggcgatt ttgatgcttt ttttacgccg ggacgccgcg atattcactc    90120
ctccgagccg cgcggggacg ttgacttctc atgcccgacg acgtgatcga ggagagaccc    90180
cgaatgtccg aaaacaccgt tttcgccgtt ccacccaggg tggaaagccc ggtacgcccg    90240
gccgcgcccg ccaaccgggt ggggcgctgg ctgctggagc accgggtgca accggcggga    90300
cccgcgggca ccgaccagca cagcacgccc caggcgtggt ggaaggtcat gtgcctgacc    90360
ggcgtcgact acttctcgac cctgtcctac ctgccgggca tcgcggcgct ggcggccggg    90420
gcggtctcgc cgctgcgac gctgctgatc gtcgcgctga ccctgttcgg gatgctgccg    90480
atgtaccgcc gggtggcgca cgagtcgccg cacgggcagg gctcggtggc gatgctggag    90540
```

```
gacctgctgc cgttctggcg cggcaagctg ttcgtgctgg tgctgctggg tttcgtggcc    90600
acctcgtgga tcatcacgat caccctgtcg gcggccgacg cgtcggtgca cgcgctggag    90660
aacccgcacg cgcccgcgtt cctgcacggg cacgaggtgc tggtcaccgt ggtgctgctg    90720
ctcgtgctgg gcggggtgtt cctgctgggc ttcaccgagg cggtcagcgt ggccatcccg    90780
ctggtcgcgg tgttcctgct gctcaacgcg gtggtcgtgg tcgccggcgt gctggaggtg    90840
atcgcgaacc cggacgtgct ggacggctgg ttcgcggcgc tgacctccac cggcggcggc    90900
ggggtgctgg gcgtggtcgg cccggccctg ctggcgttcc cgctgctcgt gctcggcctg    90960
tccgggttcg agaccggggt gagcatgatg ccgctggtcg aggcgaaggg cgccgacgac    91020
gccgaacgcc tggcgaaccg cgtccgcaac acccgcaagc tgctcaccac cgccgcgctg    91080
atcatgtcgg tgtacctggt ggccaccagc ttcgtgacca ccctgctcgt gccggtcgag    91140
cagttccgcc ccggcggcga ggccaacggg cgggcgctgg cctacctggc gcacgagctg    91200
ctcggcgagt gggtcggcac ggcctacgac atcagcagcg tgctgatcct gtggttcgcc    91260
ggcgcgtccg cgatggccgg gctgatcaac atcgtgccgc gctacctgcc cgcgtacggc    91320
atggccccgg actggacgcg cgccgtccga ccggtcgtgc tggtctacac ggtgatctgc    91380
gtcggcatca cggtgatctt ccaggccgac gtggacgccc aggccggcgc gtacgcgacc    91440
ggcatcctgg cgatgatggt gtcggcgtcg gtggcggtga ccctgtcggt ggcgcgcgcc    91500
gggcggcggg gcgcggcctc ggcgttcgcg gtgctgaccc tgatcctggt gtacgcgctg    91560
gtggagaacg tgatcgagaa gccggacggc atcacgatct cgttcgtgtt catcgtcggc    91620
atcatcgccg tctcgctggt ctcgcggatc tcgcgcacca ccgagctgcg cgtggagcac    91680
atcgagttcg acgagaccgc gcgcaggctc atcaccgact cgatcgccca cgacggcgcg    91740
ctgaccgtga tcgcgaaccg caggcaggcc ggtgacgtgg ccgagtacgc ggacaaggag    91800
gccgagcagc gcggggtgaa cccggtgccg gggcaggcgg acgtgctgtt cctggagatc    91860
gacgtggtgg accgtcgga cttcagcgac gtgctggagg tgcgcggcgt ggaggtgggc    91920
ggccaccggg tgctgcgcgc ggacagcccg gcggcgccga acgcgatcgc cgcgatactg    91980
ctggcgctgc gcgactgcac cggggtgcgc ccgcactgcc acttcgcgtg gagcgagggc    92040
agcccgctgg ggcacctgtt ccgctacctg ctggtggggc gcggcgacac ggcgccggtg    92100
gtgcgggaga tcatccgggc gcacgagtcc gacccggagc gcaggccggg catccacgtg    92160
ggggcctgag cgggcacgac ggcggggtgg tccaggcagg cagcgtggtc caggccagtg    92220
gggtgctccc ggccagcaac gtgctcccgg ccggtggggg ctccagggcg ctgcggcggc    92280
cgatcgcgcg ggcgtggtcg gcgaaccgct cgcagtgctc gctgagcagg gccgcgtcga    92340
cggcggcgtc ctcaacgccg cgcagcacgg ccagcacgga ccggggcact caccaaacgc    92400
gaagagccac accaactggg cttcggcgtg ggaggcgcgg tgcagcggtt tgtggtctcg    92460
cgctgccgcg cggcgcgggg gactgggtcg cgagcagcac ctggccgccg tgccgcgcgg    92520
cgccccgcgc caggtcgcac acggcggcca ggtccggcac cggcgcgtcc cgccggtcgt    92580
ggaacacgtc gcgcatcgcg ctctcccctcg gaggatcgga tcggaaggcc ctgatcccaa    92640
ccgggcgcgc accccggcga caagccctca cccgccgaac ttgcgctttc cttccgcccc    92700
gacccccgcc cgtcacaaac cccgtcacc ccgccgtcac tttttgtgat gacgatcagg    92760
aaacagtagt agcccattcg tgacctgcac tgacgcgcag atcaccccac ccgtcaacga    92820
aacgtaaaac cgcctggtca ccccgtcaaa gacccgtcag cacccgctc acggcgtttt    92880
ccccgttgca ccctttggc gtcgcggtcc ccacgaacgg gggccgctcg gagtcgggaa    92940
```

```
gggagcacgc tcatggccga cctggcctac gcgtcgctgc tcatcgctgt gttcggactg   93000
ctcgtcctcg gcattcgcgg actggggcgg ctctgatggg cggcacggga gtcgtggcca   93060
acgccgtcgg tggcgtgctg gccctgctgc tcatcgggta cctgttcgtc gcgctgatca   93120
ggccggagaa gttctgatgt cctcgaccac ggcgggcctg ctccaggtcg ccctgctcat   93180
cgccgcgctg gccgccgcct accggccgtt cggcgactac atggcccgcg tctacaccga   93240
cgccaagcac accaaggtcg agcgcctgct ctaccgcgca gcccgcgtcg accccgactc   93300
gcagcagcgc tggggcacct acgcgcaggg cgtgctcggc ttctccctcg tcggcgtggc   93360
cctgctgtac ctgatgcagc gagtgcagcc ctggctgccg ttcgaccacg accggggcgc   93420
ggtctcgccc ggcatggcgt tcaacaccgc cgcctcgttc gtggccaaca cgaactggca   93480
gtcctacgtc ccggagaccg tcctcggcca caccgtgcag atggccgggc tgaccgtgca   93540
gaacttcgtc tccggcgcgg tcggcatggc cgtcgccgtg gcgctggtgc gcggcttcac   93600
ccgcgagggc tccgaccggc tcggcaactt ctgggtcgac ctcaccaggg gcaccctgcg   93660
cgtcctgctg cccgtgtcgt tcgtgttcgc catcgtgctg gtcgcgaccg gcgtcgtgat   93720
gagtctgaag gcgggcgtgg acgtggacgg ccagcaggtc gccatcgccc cggccgcctc   93780
gcaggaggcc atcaaggagc tcggcaccaa cggcggcggc atcttcaacg ccaactccgc   93840
ccacccgttc gagaacccca acggctggtc gaacctggtc gagatcttcc tgatcctgct   93900
gatcccggtc tcgctcaccc gcaccttcgg caccctggtc ggcaaccgca agcagggcta   93960
cgtgctgctc agcgtcatgg gcgtgctgtg gaccgcgatg ctcgcggtca tctgggcggc   94020
cgaggcgcac ggcctgcgcc ccctggaggg caaggagctg cggttcggcg tccccggcag   94080
cgccctgttc gccaacacca ccaccgccac ctccaccggc gcggtcaacg ccatgcacga   94140
cagcctcacc ggcctgggcg gcggcgcgac gctgctgaac atgctgttcg gcgagatgac   94200
gccgggcggc gtcggcaccg gcctgtacag catcctggtg atggcgatca tcgcgatgtt   94260
cctggccggt ctgatggtcg ggcgcacccc ggagtacctg ggcaagaagc tgggccgccg   94320
cgaggtgacc tgcgccgcgc tgtccatcct ggcgatgccc gcgctggtgc tggtcggcgc   94380
cgggatctcg gcggtgctgc cgtcgacggc cgggtacctg aacaacccccg gcgagcacgg   94440 cctgtccgag atcctctacg cctacgcgtc ggcctcgaac aacaacggca gcgcgttcgc   94500
gggcatcacc gtgaccagcg actggttcca gtcctcgctc ggcgtctgca tgttgctcgg   94560
ccggttcgtc ccgatcatcg cggtgctgtg cctggccggt tcgctcgccc ggcagaagcg   94620
cgccccgcgg accgcgggca cgctgcccac ggacagcccg ctgttcgcct cgctgctggt   94680
cggcgcgatc gtgctcgtcg ccgccctcac cttcgtcccc gccctcgccc tcggccccat   94740
cgccgaggca ctgctgtgac caccaccgac acccgccagc ccgcccccga ggacacgggc   94800
gcgcggcccc cggccaagcc cgtcccgtcg ggcgtgttcg cccccgcgcc gctgctcacg   94860
tccctgccgg acgcgctgcg caagctccac ccccgccacc agctgcgcaa ccccgtgatg   94920
ttcgtggtgt gggcgggctc ggtcctggtc acggtcttcg ccgtcaccga cccgaacccg   94980
ttcacgatcg cggtcgcgct gtggctgtgg ttcaccgccc tgttcgccaa cctcgccgag   95040
gccgtcgccg aggggcgcgg caaggcgcag gccgagtcgc tgcgcaggac taagaccgac   95100
gcgctggccc gcctgaccga cggccgcacc gtgcccggca ccgagctgaa ggtcggcgac   95160
ctggtcgtgg tcgaggccgg tgaggtgatc ccggcgacg gcgacgtggt cgagggcatc   95220
gccaccgtcg acgagtcggc gatcaccggc gagtccgcgc ccgtggtgcg cgagtccggc   95280
ggcgaccggt gcgcggtcac cggcggcacc accgtgctgt cggaccggat cgtcgtgcgc   95340
```

```
gtcaccagca agccgggcga gacgttcgtg gaccggatga tcgcgctggt cgagggcgcg   95400
cagcggcaga agacgccgaa cgagatcgcg ctgacgatcc tgctgtccac gctcacgatc   95460
atcttcctgc tcgcggtgct cgcgctccag ccgttcgcgg tgtactccgg cggcgagcag   95520
tcggtgatcg tgctgaccgc gctgctggtg tgcctgatcc ccaccacgat cggcgcgctg   95580
ctgtccgcga tcggcatcgc gggcatggac cgcctggtgc agcgcaacgt gctggccacc   95640
tcgggccgcg ccgtcgaggc ggccggtgac gtggacacgc tgctgctgga caagaccggc   95700
accatcacct ggggcaaccg ccgcgccacc gagctgatcc ccgcgcccgg cgtcacgctg   95760
gacgagctgg tggacgccgc ccggttgtcg tcgctggccg acggcacccc cgagggccgc   95820
agcgtggtcg agctgtgcgc gaccgggcac ggccgctccc ccgagcccac cgacgcggag   95880
aagaccggcg agttcgtgcc gttcaccgcc cagacccgga tgagcggcat cgacctggac   95940
ggccgcagcg tccgcaaggg cgccgcgacc gcgttcaccc tcaccgactc ggtcaagtcc   96000
acggtggacg agatcagcgg cgacggcggc accccgctgg tggtcgccga cggcgagcgg   96060
gtgctcggcg tgatccggct gtccgacgtg gtcaagcccg gcatgaagga gcggttcgcc   96120
gagctgcgcg ccatgggcat ccgcacggtc atggtcaccg cgacaacccc gctgaccgcc   96180
agggcgatcg cggccgaggc gggggtcgac gactacctcg ccgaggccaa gcccgaggac   96240
aagatggccc tgatccgcaa ggagcaggag ggcggcaagc tggtcgcgat gaccggcgac   96300
ggcaccaacg acgcgccggc gctggcccag tccgacgtgg gcgtggccat gaacaccggc   96360
acctcggccg ccaaggaggc cgggaacatg gtggacctgg actccgaccc caccaagctc   96420
atcgagatcg tggagatcgg caagcagctg ctgatcacgc ggggcgcgct gacgacgttc   96480
tcggtcgcca acgacctggc gaagtacttc gcgatcctgc ccgccatgtt cgccgcgatc   96540
cacccgcagc tggacaagct caacgtcatg ggcctggcca cgccgcagtc ggcgatcctg   96600
tcggcggtca tcttcaacgc gctgatcatc gtggtgctga tcccgctggc gctgcgcggc   96660
gtgcgctaca agccctccag cgcgagctcg ctgctgcggc gcaacctgct ggtgtacggc   96720
gtcggcggca tcatcacgcc gttcgtcggc atctggctca tcgacctgct cgtccgcctc   96780
atccccggaa tcgggtgaac tccgtgaacg cgttcgtgaa gcaggccctg gccggtctgc   96840
gcgtcctgct ggtgctgacc gtcatcaccg gcgtgctcta ccccgccgcc gtctggctcg   96900
tctcgcgggt gccggcctg cacgccaacg ccgaggccac cggcaccgag ctggtcgtgg   96960
cgccgcgcga gggcgacggc tggttccagc gcgcgcccgtc gatggcgacg ctgcccgcgt   97020
cgggcgggtc caacaagggc gagcgcaacg ccgactacga cgcggtgatc gccgagcgcc   97080
gcaccgagat cgcccggcgc gagggcgttg cggaggacgc cgtgccgcag gacgcggtga   97140
ccgcctcggc ctccgggctg gacccgctga tcagcgccga gtacgcggcg atccaggtgc   97200
cgcgcgtggc gcgggagcgc ggggtgtcgg aggacgccgt gcgggcgctg gtcgccgagg   97260
cgtcggtggg ccgctcgctc gggttcgtgg gcgagccggg cgtcaacgtc accgccctca   97320
accgggccgt cgacgcggcg gagtgagacc gaccgggggc cgtcctcgcg gcggcccccg   97380
gtcttcccca tttctctgat ctcgggagcg ggcgggaccg tggacaagcg caagcgcggc   97440
gaactgcgca tctacctggg cgcggcgccg ggcgtcggca agaccttcgc gatgctcggc   97500
gaggcgcacc gccgccgggg gcgcggcgcg gacgtcgtcg tcgccctggt cgagacgcac   97560
ggccgcgagc gcaccgccac catggtcgac ggcctggagg tgctgccccg caaggaggtc   97620
cagcaccggg ggaccacgat caccgagatg gacgtggacg cggtgctggc ccgcgcgccc   97680
gagatcgccg tggtggacga gctggcgcac accaacgccc ccggctcccg caacgccaag   97740
```

```
cgctggcagg acgtcgagga gctgctggac gccggcatcg acgtgctgtc cacgctcaac    97800
atccagcacc tggagtcgct caacgacgtg gtgcgccgca tcacccgcgt cgagcagcgc    97860
gagaccatcc ccgacgaggt ggtgcgccgc gccgagcagg tggagctggt cgacctgacc    97920
ccggaggcgc tgcgccgccg cctggcgcac ggcaacgtct acgccgcgca caagatcgac    97980
gccgcgctgg gcaactactt ccgggtcggg aacctgaccg cgctgcgcga gctggcgctg    98040
ctgtgggtgg ccgaccaggt ggacgtggcg ctccagcggt accgcaccga gcagcgcatc    98100
accgacacct gggaggcccg cgagcgggtc gtggtcgcgg tgaccggcgg cgcggagagc    98160
gagaccctga tccgcagggc ccgccgcatc gccgcgcgcg ccggggcgga gctgctggtg    98220
gtgcacacca tgcgcggcga cggcctcgcg ggttccgcgc cggagtcgat ccggacccgc    98280
gtcgggctca ggtgctcgac ggtgctcttc aacgtggtct cctcgtaacg ggacgtgcgg    98340
aacaccccgc agcgcccagg gtcgggcggc tgacgggatt cgcctgagtc taggcgaggc    98400 cgccccccggc cggggtggca ccccgcgacc gggtggttca cgtgcgggtg cgcgcgcccg    98460
gcgcggcgcg cgcggtgcga gaggtgggcc gtccggcggc gcgcggtttt ccgacatggc    98520
gcgcgcacga aatagtttc ggcgggtcgg gcgccgtcga atcgactcgg ggtcgggttt     98580
tccgcgccac cccggaagcg gacgaaccgg gcgggcgaac cggcgggcg gtgcgcggac      98640 aacgggcgcg accgccgcgg tgcgccggtt tgggcagcct ttaccgccct ccaggtcacc    98700
cattccgccg ttgcggggaa catccgcgta ccagtggccc ccggcggaca cgcggcccag    98760
cacccgctag gccgttcgca ggacgtcgtg gtgcaccggg agcgtgaaac cgaacgtaac    98820
cggacagcgg cgggctcaag tggggtaaca ctggcgccgc agcgcactct tacccacagc    98880
gacgaacgcg gcggaacgct accctttaca ggtgaagtga ggccattcgg agcaccggtg    98940
cgcagaaaac tttcacgccc ggagatgact ccactcgccg tagtccatta gtgtgggatt    99000
ccggtaccgt tgcgccgcag gccgcaagaa ggcggccagg aaagacgatt aactcatccg    99060
ggcgccccgc cgtcgtgcac gtgaacgcga cgggcgaccg gaacggaac gagcgagaca     99120 tgtcatcgcg ctctttacca cctaccagaa aaggtgccga tgaccccgat gaagaccatt    99180
ccgccgattc ccccgaacac gcgggcgtcc gcccgtccgc cgctcgggca accgcacgac    99240
gggcttgcgc gccacccgga accccagggc ccggccgcga ggcgatgttg acccgacccc    99300
cggccaccag ccgggacagg ccgaccaccg ccacgcgcgg aacccacggc gaaccgcctc    99360
tcgccgtgat ccaccacgga ccgttgggga gttccatgga gacccgtcaa cttctggcgt    99420
tcaccacagt ggtgcagacc ggcagcttca cgaaggccgc cgccacgctg aactgctctc    99480
agcccacgat caccaccagg atcaaggcgc tggaggagac cctcggcgtc gccctgttcc    99540
gcaggttgcc gcgcggcatc cagatgacct ccgccgggt cgagctgctg ccgttcgcgc     99600
gcaacatcat cacgctcacc gacaaggccc gcaaggcgat caccatgaac ggggagccgc    99660
acgggcacct cgtgataggc agcgcccaga gcctcaccga ctaccggctc ttaccccctga   99720 tcgagtacat gtgctggcgc tacccgagcg tccagatctc gctgcactcg cgaacaaccc    99780
ggtcgaacct ggccgccgtg cgcgaggggca ggttggactg cgcgttcttc atcggccgg    99840 tcgagcagcg ggacggtctg gagacgacgg tgctgtgccc cgaaccgctg gtgatggtcg    99900
cgggccccgg ccacgcgctg gcgcggtcgg gcgcggtcac cgaggcggac ctgcgggca     99960 gcacgctggt cagggccgag aacgggcga gctaccacga gcagttcgag cgggcgctcg   100020
ggctgcacga ggccgagtcg cgatcgccgg tgctggccct ggactcggtc gacgcggcca   100080
agcgggcggt cgcctcgggg ctgggcatct cgctggtgcc ggaggtcacg gtcgccgcgg   100140
```

```
agctggcgga cggcaggctc agccgcatcg gctggacccc gccgttccgg gtgttcaccc    100200
agttcgcgtg gcgccaggac aactcggcga accgtcggt gaccgcgctg gtctcggcgg    100260
cggcgcaggt ggtgagcgag caggtggccg cgacacccgc gtagggcgtc gacgtgcagg    100320
gtcgtggatg cggagcggcc ccctcgtgct gcgcagaggg ggccgagacc gtcggggcga    100380
caggatttga acctgcgacc ccccgctccc aaagcgggtg cgctaccaaa ctgcgccacg    100440
ccccggtcac caggagctta gcgcgacgcg ctaagctgtt ttcagcaccc accggtggg    100500 cgctgcgcgg gtgtagctca atggtagagc cccagccttc caagctggtc atgcgggttc    100560
gattcccgtc acccgctcca ccagatcc                                      100588
```

<210> SEQ ID NO 12
<211> LENGTH: 38
<212> TYPE: DNA
<213> ORGANISM: Artificial sequence
<220> FEATURE:
<223> OTHER INFORMATION: Primer

<400> SEQUENCE: 12
ttaagcttgg accggcgcga actcgcggac acccacct                            38

<210> SEQ ID NO 13
<211> LENGTH: 38
<212> TYPE: DNA
<213> ORGANISM: Artificial sequence
<220> FEATURE:
<223> OTHER INFORMATION: Primer

<400> SEQUENCE: 13
tttctagagg tcatgcgccc gccaggatca ggtcgacc                            38

<210> SEQ ID NO 14
<211> LENGTH: 38
<212> TYPE: DNA
<213> ORGANISM: Artificial sequence
<220> FEATURE:
<223> OTHER INFORMATION: Primer

<400> SEQUENCE: 14
tttctagacc ttcgtaaggc tccctgcct gggcatgg                             38

<210> SEQ ID NO 15
<211> LENGTH: 38
<212> TYPE: DNA
<213> ORGANISM: Artificial sequence
<220> FEATURE:
<223> OTHER INFORMATION: Primer

<400> SEQUENCE: 15
ttgaattctc tgctcggcta cggcttcggc gacgagta                            38

<210> SEQ ID NO 16
<211> LENGTH: 33
<212> TYPE: DNA
<213> ORGANISM: Artificial sequence
<220> FEATURE:
<223> OTHER INFORMATION: Primer

<400> SEQUENCE: 16
cgcaagctta gacctcgacc accggtgtct gga                                 33

<210> SEQ ID NO 17
<211> LENGTH: 32
<212> TYPE: DNA

```
<213> ORGANISM: Artificial sequence
<220> FEATURE:
<223> OTHER INFORMATION: Primer

<400> SEQUENCE: 17
ccgtctagac acgatttcca gcgcatggcc ca                        32

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
tgctctagac tcacccgctc gccttcgtca                           30

<210> SEQ ID NO 19
<211> LENGTH: 31
<212> TYPE: DNA
<213> ORGANISM: Artificial sequence
<220> FEATURE:
<223> OTHER INFORMATION: Primer

<400> SEQUENCE: 19
tgcgaattct gagccaccac ggcgtgtgac a                         31
```